United States Patent
Ichikawa et al.

(10) Patent No.: US 11,629,341 B2
(45) Date of Patent: *Apr. 18, 2023

(54) METHOD FOR PRODUCING SELENONEINE

(71) Applicant: KIKKOMAN CORPORATION, Noda (JP)

(72) Inventors: Keiichi Ichikawa, Noda (JP); Yasutomo Shinohara, Noda (JP); Seiichi Hara, Noda (JP); Keiko Kurosawa, Noda (JP); Yumiko Yamashita, Yokohama (JP); Michiaki Yamashita, Yokohama (JP)

(73) Assignee: KIKKOMAN CORPORATION, Noda (JP)

( * ) Notice: Subject to any disclaimer, the term of this patent is extended or adjusted under 35 U.S.C. 154(b) by 2 days.

This patent is subject to a terminal disclaimer.

(21) Appl. No.: 17/319,362

(22) Filed: May 13, 2021

(65) Prior Publication Data

US 2021/0317463 A1 Oct. 14, 2021

Related U.S. Application Data

(62) Division of application No. 15/750,792, filed as application No. PCT/JP2016/068128 on Jun. 17, 2016, now Pat. No. 11,028,400.

(30) Foreign Application Priority Data

Aug. 7, 2015 (JP) .................................. 2015-157443

(51) Int. Cl.
| | | |
|---|---|---|
| *C12N 9/88* | (2006.01) | |
| *C12N 9/02* | (2006.01) | |
| *C12P 17/10* | (2006.01) | |
| *C12N 1/14* | (2006.01) | |
| *C12N 15/09* | (2006.01) | |
| *C12N 15/63* | (2006.01) | |
| *C12R 1/69* | (2006.01) | |
| *C12R 1/66* | (2006.01) | |

(52) U.S. Cl.
CPC .............. *C12N 9/0071* (2013.01); *C12N 1/14* (2013.01); *C12N 9/88* (2013.01); *C12N 15/09* (2013.01); *C12N 15/63* (2013.01); *C12P 17/10* (2013.01); *C12R 2001/66* (2021.05); *C12R 2001/69* (2021.05)

(58) Field of Classification Search
CPC .......... C12N 9/0071; C12N 9/88; C12P 17/10
See application file for complete search history.

(56) References Cited

U.S. PATENT DOCUMENTS

2017/0321235 A1 11/2017 Hara et al.

FOREIGN PATENT DOCUMENTS

| JP | 2005-176602 A | 7/2005 |
|---|---|---|
| JP | 5669056 B2 | 2/2015 |
| WO | WO 2014/100752 A1 | 6/2014 |
| WO | WO 2016/121285 A1 | 8/2016 |

OTHER PUBLICATIONS

MP Biomedicals, LLC. Sodium Selenite, cell culture reagent. Jun. 200.*
"The standard for ingestion of selenium in meals", Report on the Study Group on Formulation of Dietary Intake Standards for Japanese (2015 edition), Mar. 28, 2014, p. 340.
Ayotte et al., "Seleoneine content of traditional marin foods consumed by the Inuit in Nunavik, Northern Canada", Oct. 5, 2015 (Oct. 5, 2015), Global Advances in Selenium Research From Theory to Application, pp. 173-174, XP009509438, ISBN: 978-1-138-02731-2.
Bello et al., "The Neurospora crassa mutant NcΔEgt-1 identifies an ergothioneine biosynthetic gene and demonstrates that ergothioneine enhances conidial survival and protects against peroxide toxicity during conidial germination", Fungal Genetics and Biology, 2012, vol. 49, ISSN 1087-1845, pp. 160-172.
Chinese Office Action and Search Report for Chinese Application No. 201680044520.X, dated Sep. 28, 2020, with English translation of the Office Action.
European Office Action issued in Application No. 16834870.4 dated Oct. 26, 2020.
Extended European Search Report dated Dec. 17, 2018, in European Patent Application No. 16834870.4.
Genghof, "Biosynthesis of Ergothioneine and Hercynine by Fungi and Actinomycetales", vol. 103, No. 2, Journal of Bacteriology, Aug. 1970, pp. 475-478.
International Preliminary Report on Patentability and Written Opinion and English translation dated Feb. 22, 2018, in PCT International Application No. PCT/JP2016/068128.
International Search Report for PCT/JP2016/068128 (PCT/ISA/210) dated Sep. 20, 2016.
Japanese Office Action for Japanese Application No. 2017-534126, dated Apr. 21, 2020, with an English translation.
Machida et al., "Unnamed protein product [Aspergillus oryzae RIB40]", GenBank: BAE60470.1 Jun. 4, 2011, total of 2 pages.
Machine English translation of claims and description of JP 2005-176602 A (Jul. 7, 2005).

(Continued)

*Primary Examiner* — Yong D Pak
(74) *Attorney, Agent, or Firm* — Birch, Stewart, Kolasch & Birch, LLP

(57) ABSTRACT

The purpose of the present invention is to provide a method for producing selenoneine that allows production of selenoneine at higher yields as compared with a conventional technology, and, therefore, enables selenoneine production on an industrial scale. This purpose can be achieved by a method for producing selenoneine, comprising the step of applying histidine and a selenium compound to a transformant that has a gene encoding an enzyme of (1) below introduced therein and that can overexpress the introduced gene, to obtain selenoneine.
(1) An enzyme that catalyzes a reaction in which hercynylselenocysteine is produced from histidine and selenocysteine in the presence of S-adenosylmethionine and iron (II).

12 Claims, 9 Drawing Sheets

Specification includes a Sequence Listing.

(56) References Cited

OTHER PUBLICATIONS

Melville et al., "Ergothioneine in Microorganisms", J. Biol. Chem., 1956, vol. 223, pp. 9-17.
Mora-Lugo, "Development of a transformation system for Aspergillus sojae based on Agrobacterium ftumefaciens-mediated approach," BMC Microbiology (2014), vol. 14, No. 247, 7 pages.
Office Action dated Dec. 8, 2020, in Japanese Patent Application No. 2017-534126.
Office Action issued in European Patent Application No. 16834870.4 dated Jan. 15, 2020.
Office Action dated Mar. 16, 2021, in Chinese Patent Application No. 201680044520X.
Pluskal et al., "Genetic and Metabolomic Dissection of the Ergothioneine and Selenoneine Biosynthetic Pathway in the Fission Yeast, S. pombe, and Construction of an Overproduction System". PLOS One, 2014, vol. 9, No. 5, e97774, pp. 1-12.
Sawano, T et al., "N-methyltransferase[Aspergillus oryzae RIB40]", GenBank, Accession No. XP_001727309.1, Sep. 18, 2020 (1 page total).
Studer, "Residue mutations and their impact on protein structure and function: detecting beneficial and pathogenic changes," Biochem. J. (2013), vol. 449, pp. 581-594.
Vit et al., "Ergothioneine Biosynthetic Methyltransferase EgtD Reveals the Structural Basis of Aromatic Amino Acid Betaine Biosynthesis", ChemBioChem 2015, vol. 16, pp. 119-125.
Written Opinion of the International Searching Authority for PCT/JP2016/068128 (PCT/ISA/237) dated Sep. 20, 2016.
Yamashita et al., "Identification of a Novel Selenium-containing Compound, Selenoneine, as the Predominant Chemical Form of Organic Selenium in the Blood of Bluefin Tuna", vol. 285, No. 24, Jun. 11, 2010, Journal of Biological Chemistry, pp. 18134-18138.
Zhao et al., "Cysteine desulfurase NFS1 [Aspergillus oryzae 3.042]", GenBank: EIT79021.1, Jun. 18, 2012, total of 2 pages.
Zhao et al., "Cysteine desulfurase NFS1 [Aspergillus oryzae100-8]", GenBank: KDE85407.1, May 16, 2014, total of 2 pages.
Chinese Office Action and Search Report for Chinese Application No. 201680044520.X, dated Sep. 1, 2021, with an English translation.
Communication Pursuant to Article 94(3) EPC dated Apr. 1, 2022, in European Patent Application No. 16 834 870.4.

* cited by examiner

[FIG.1]
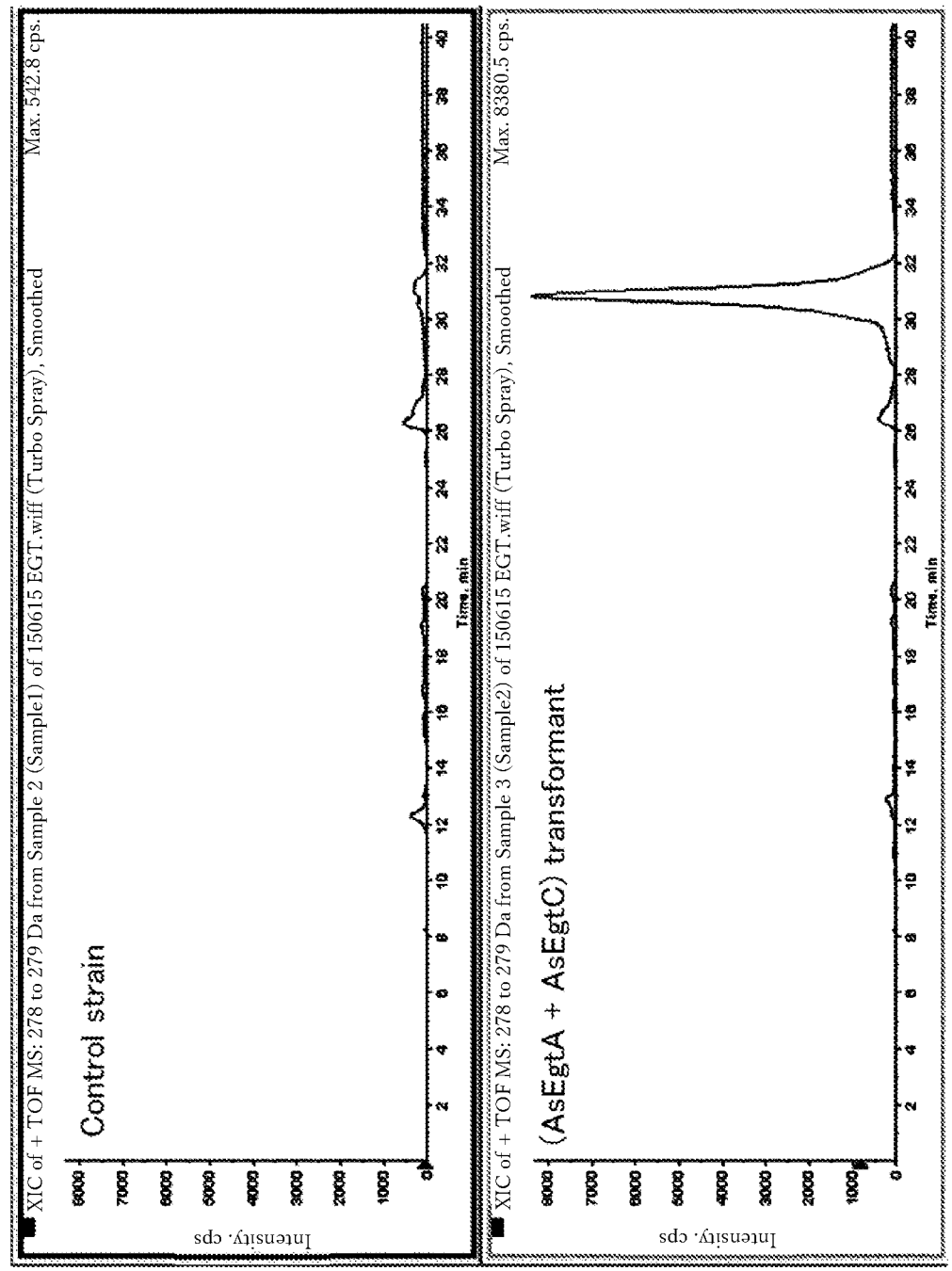

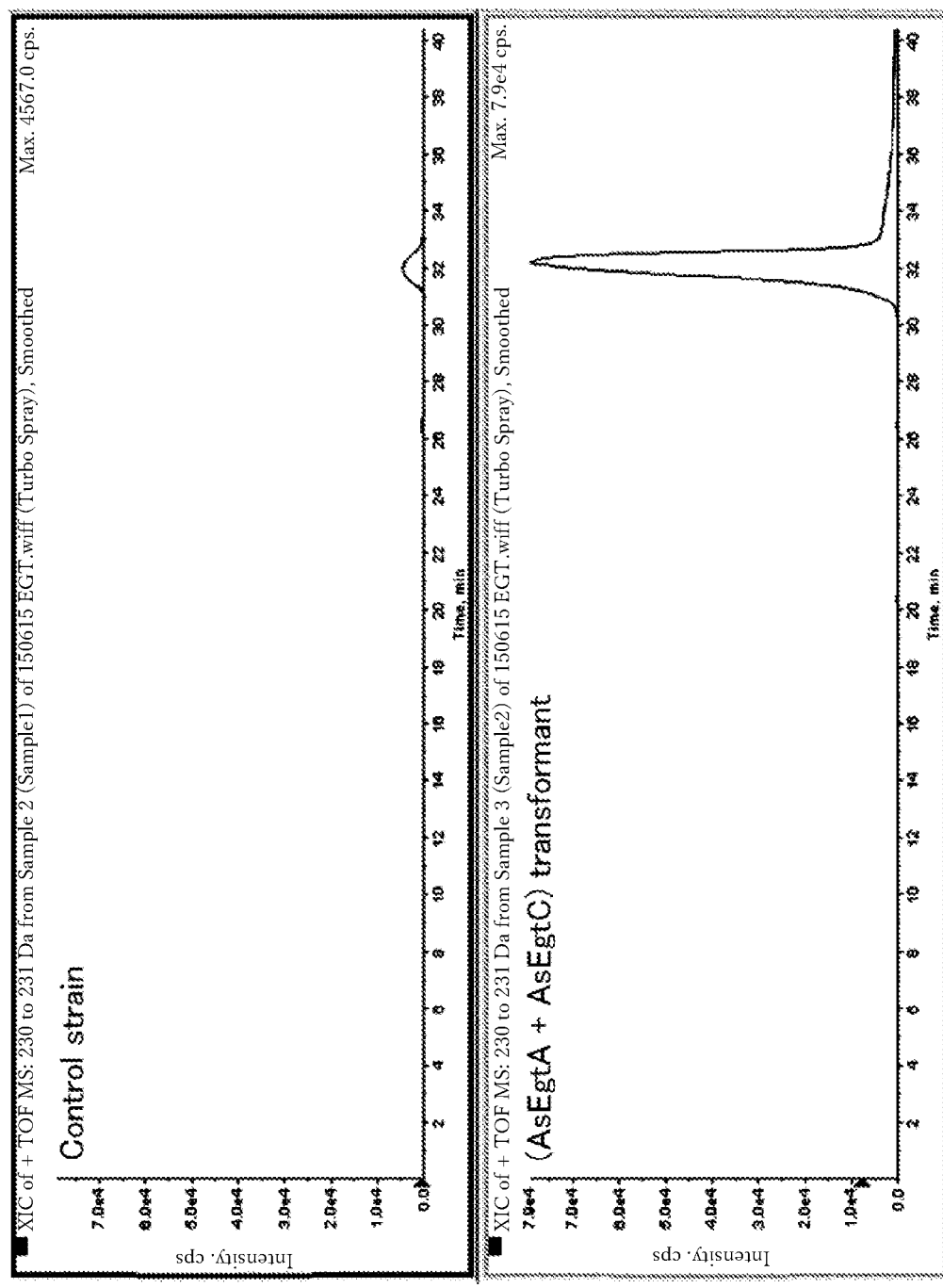

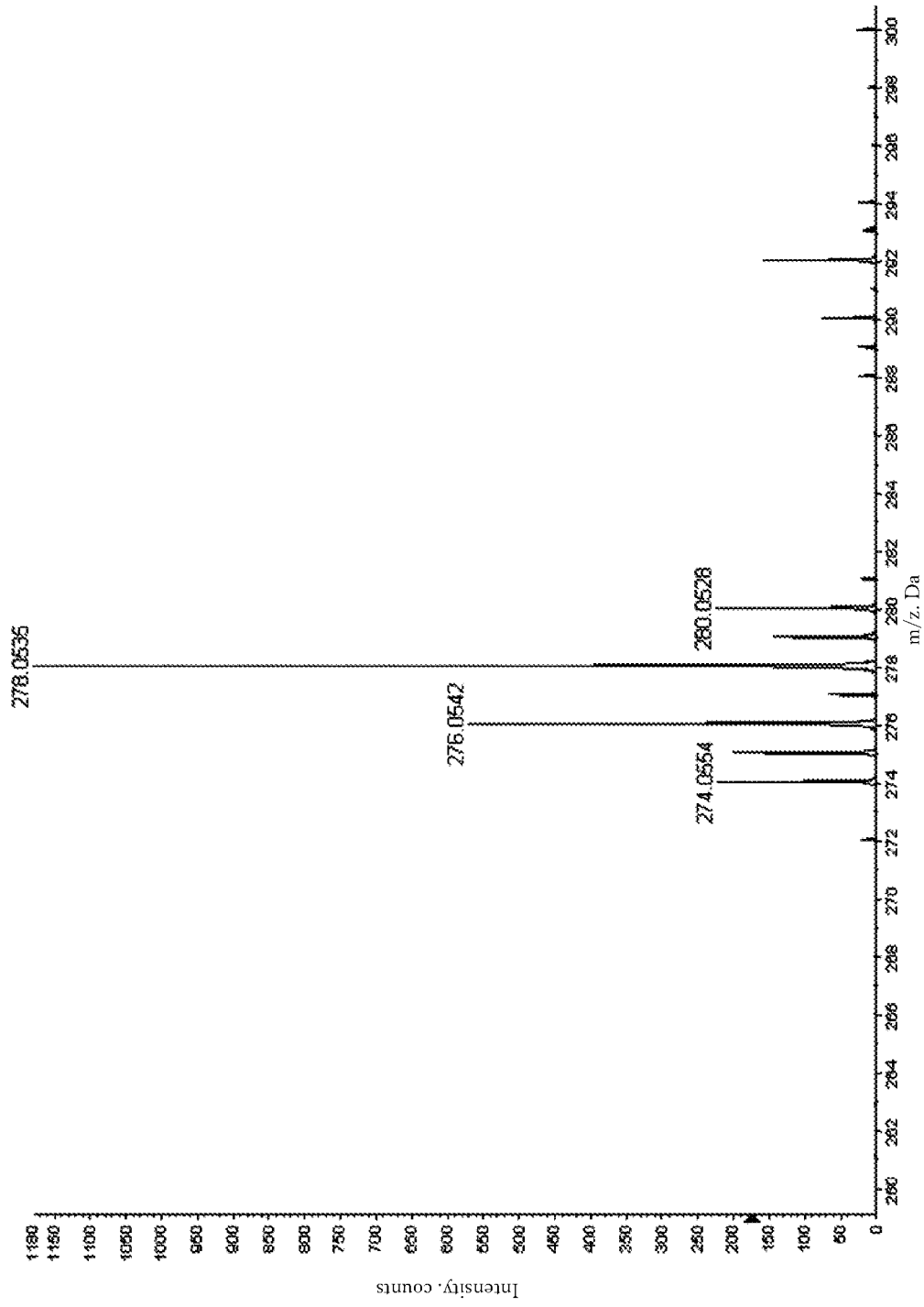
[FIG. 3]

[FIG. 4]
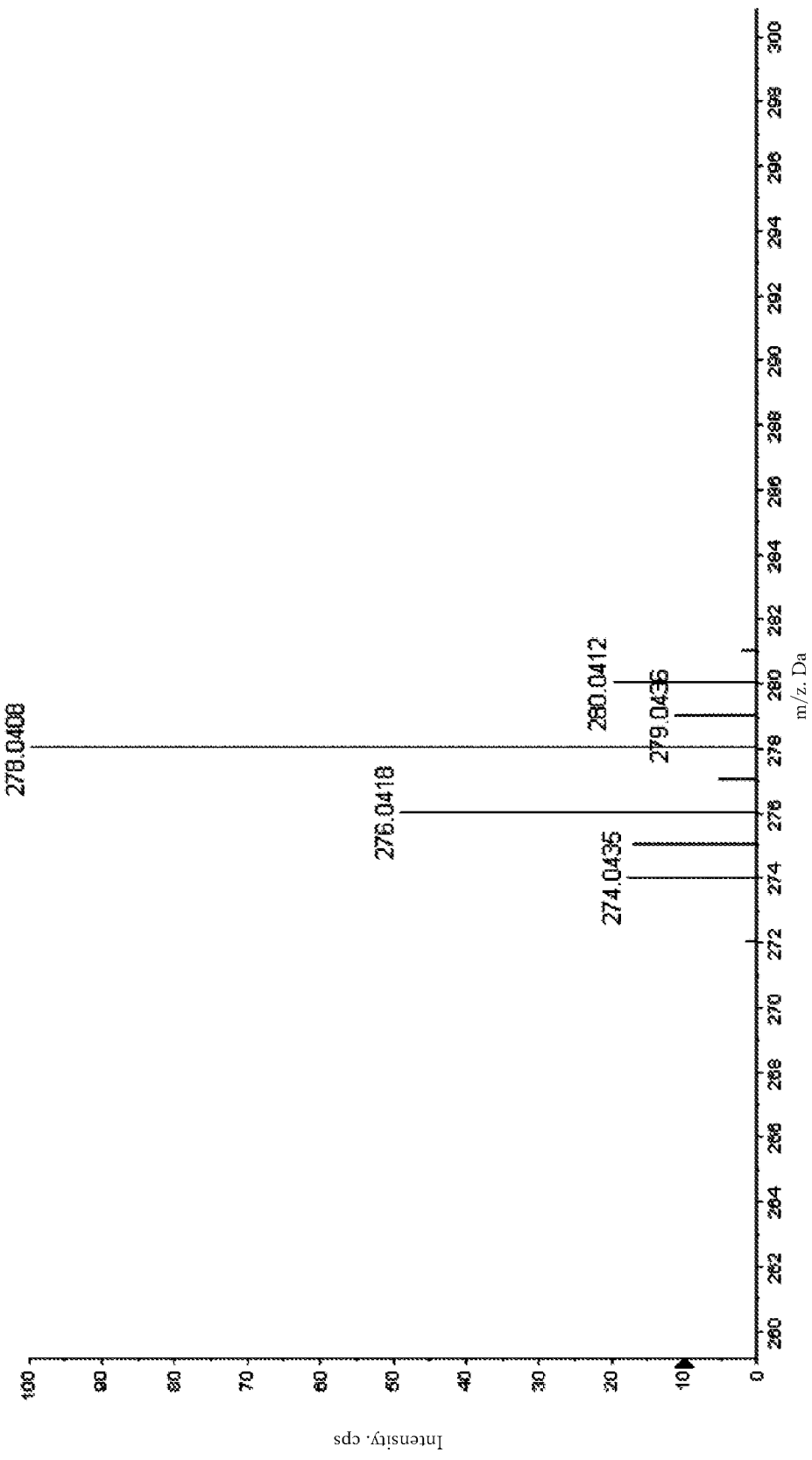

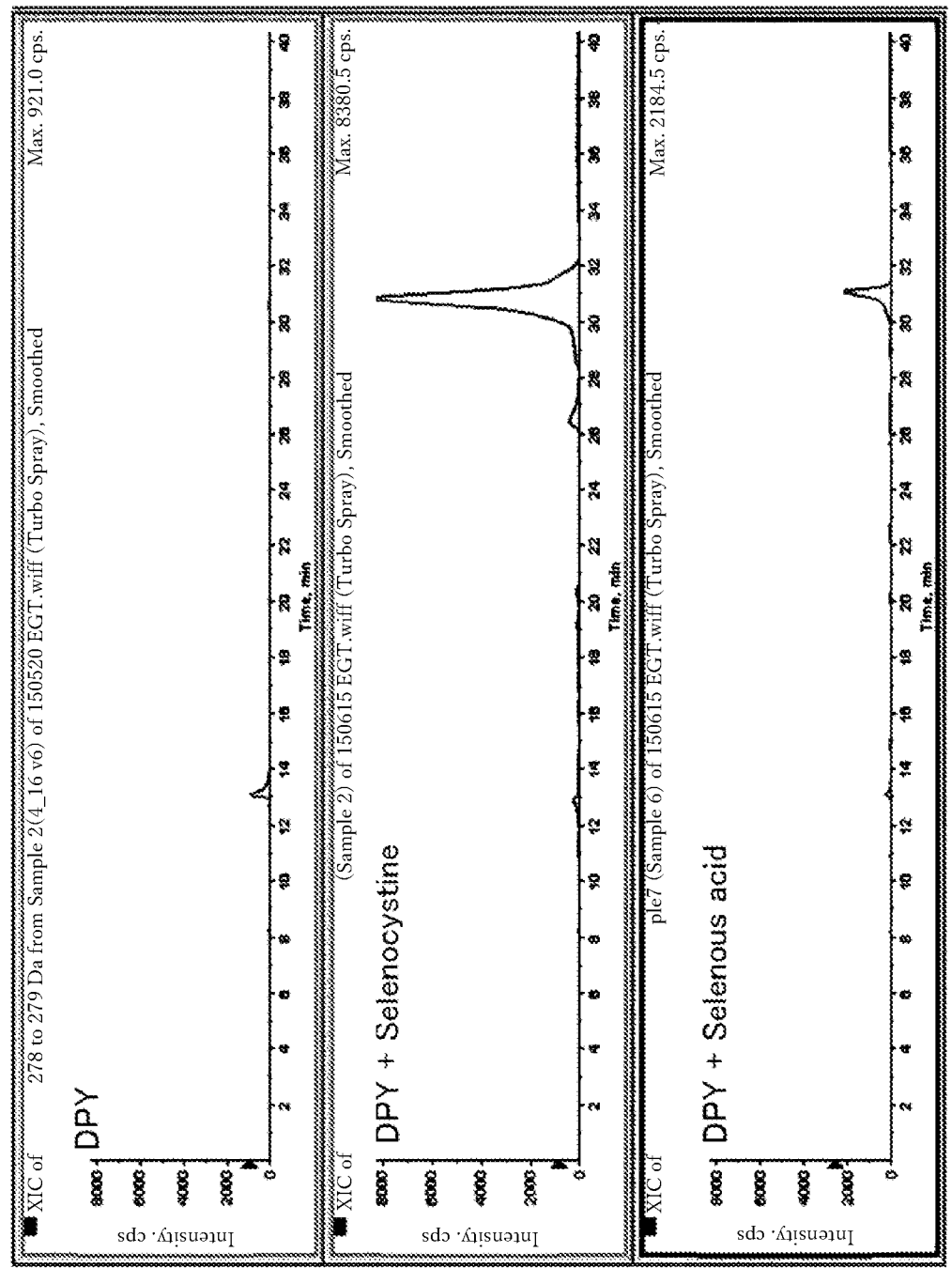
[FIG. 5]

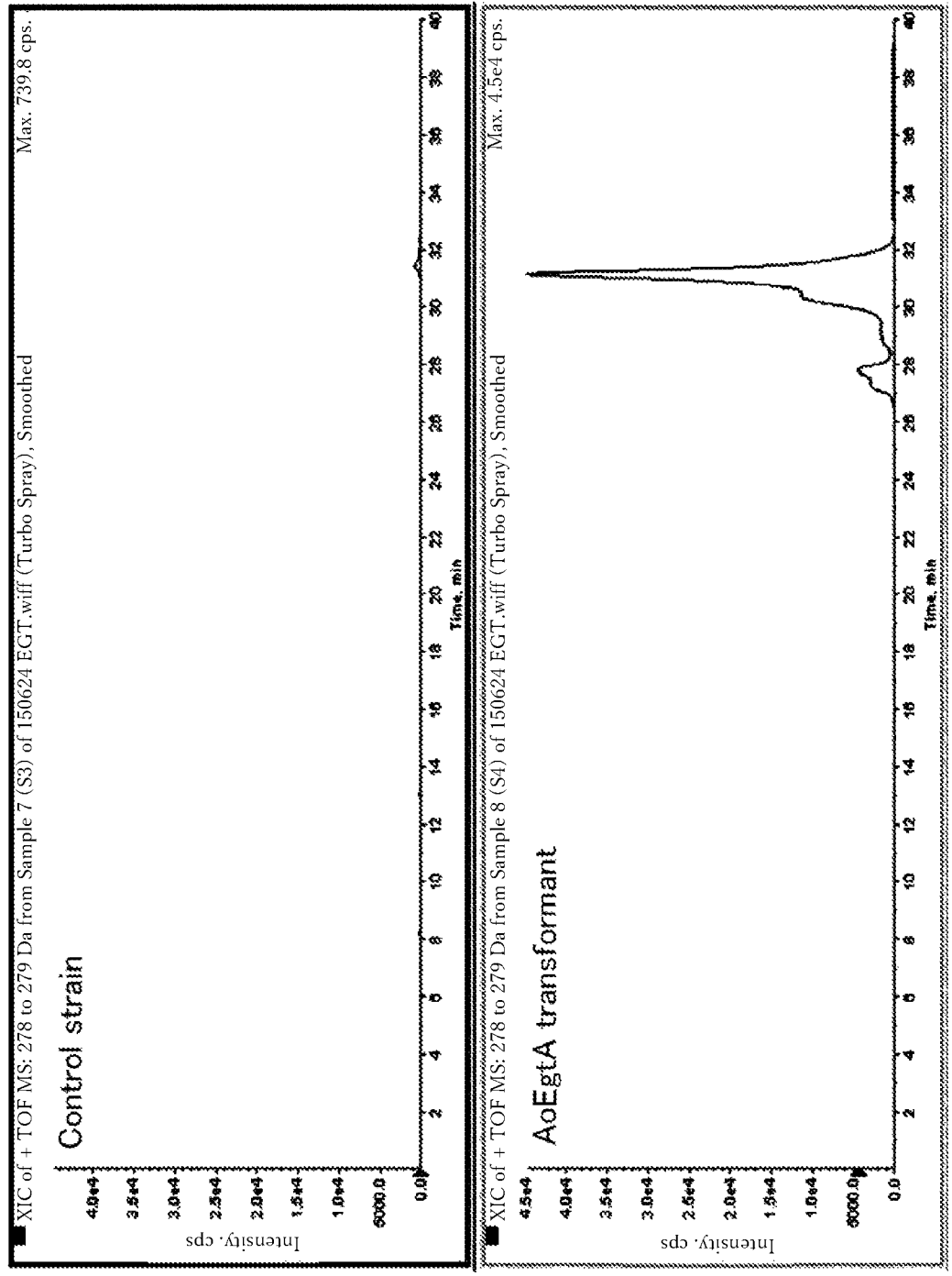
[FIG. 6]

[FIG. 7]
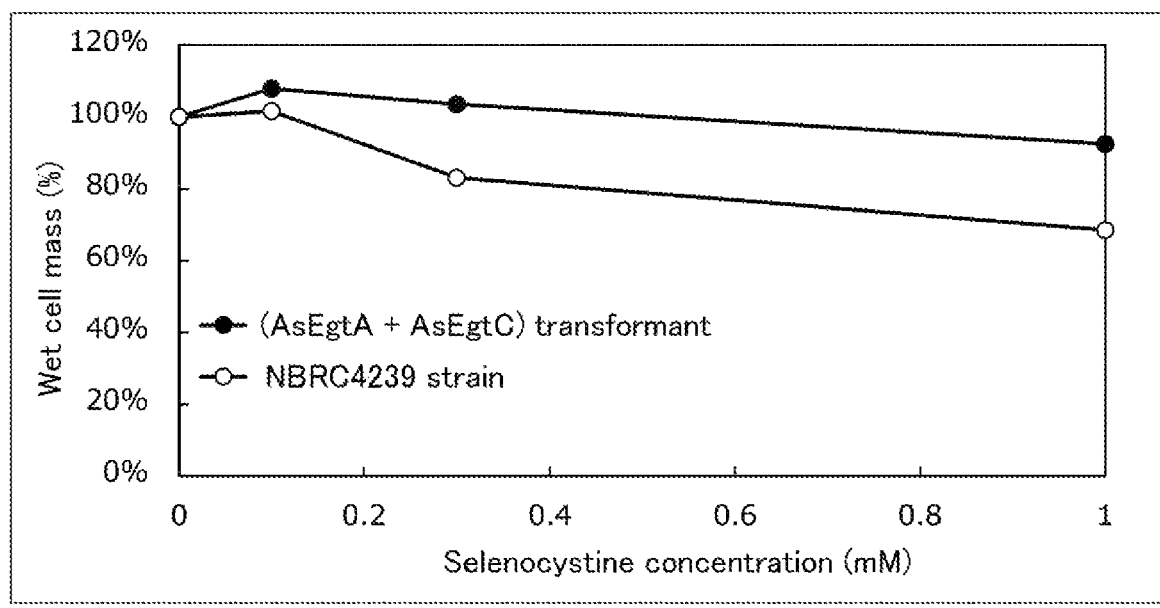

[FIG.8]
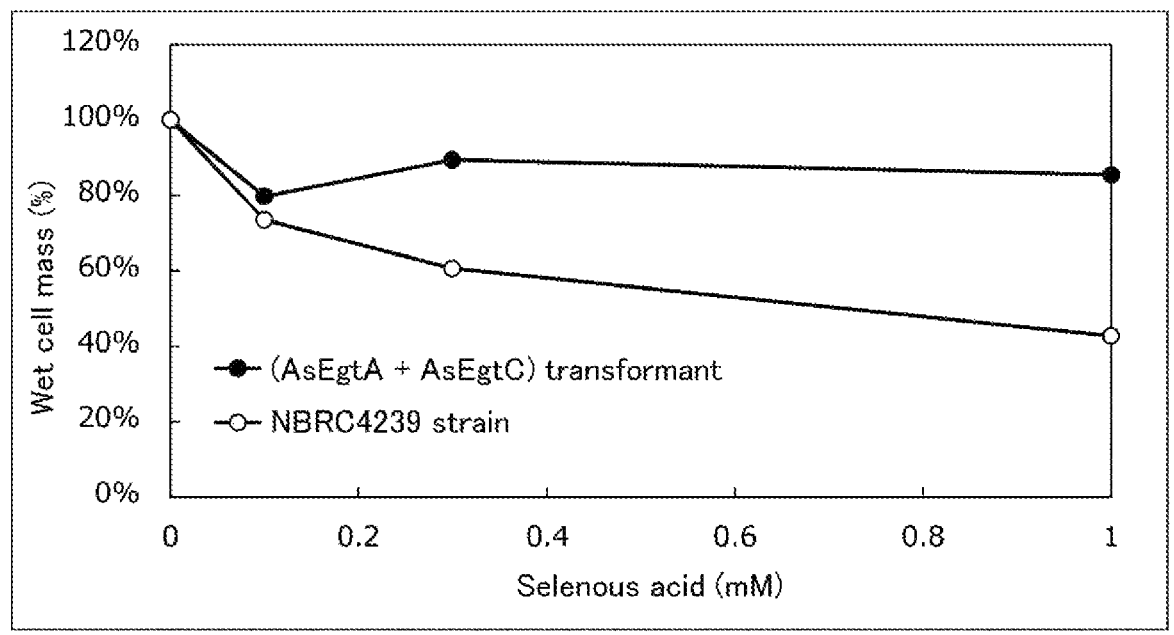

[FIG.9]
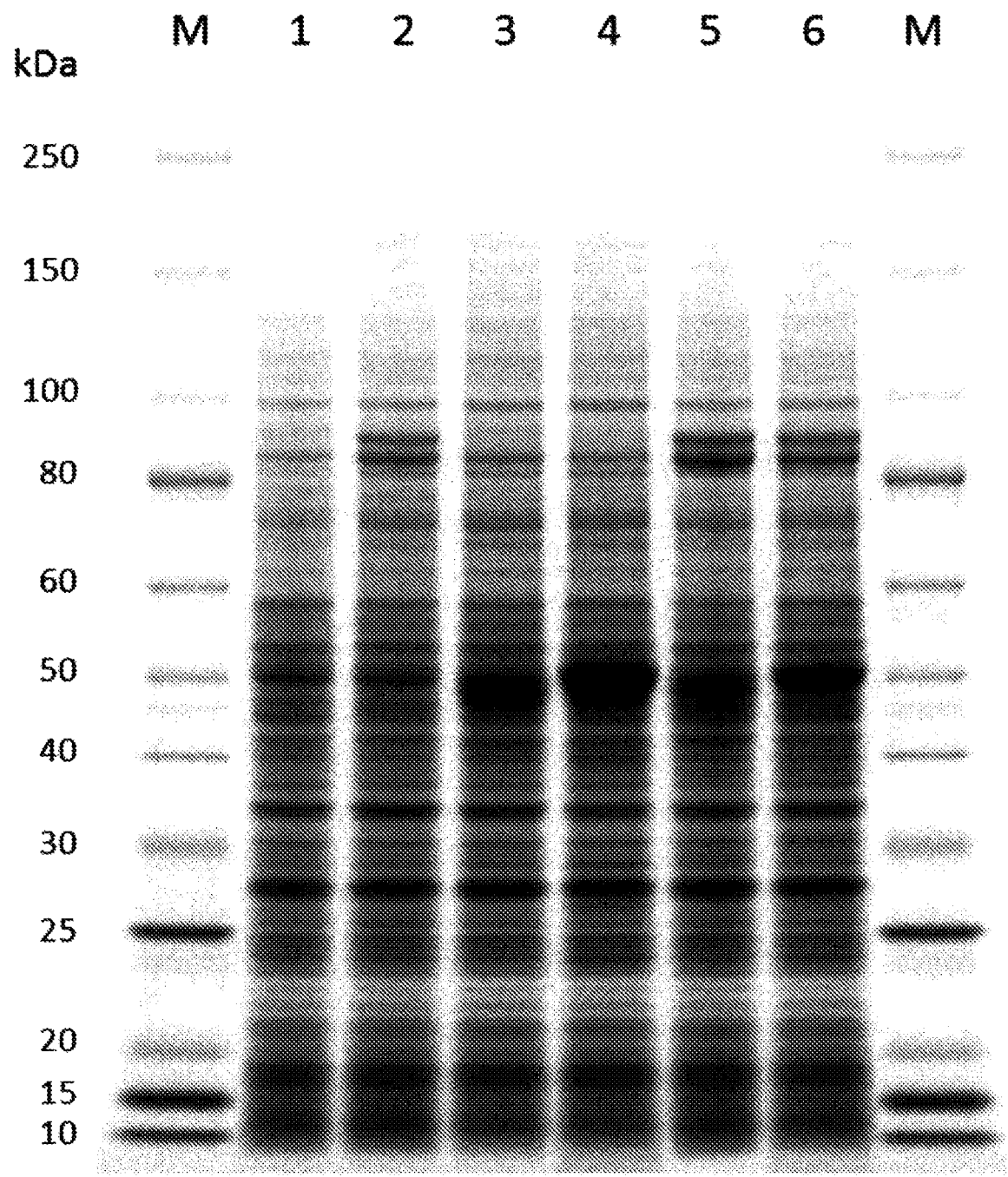

```
                            SEQUENCE LISTING

<160> NUMBER OF SEQ ID NOS: 32

<210> SEQ ID NO 1
<211> LENGTH: 2925
<212> TYPE: DNA
<213> ORGANISM: Aspergillus sojae

<400> SEQUENCE: 1
atgtcacctt tggctctctc tcctaagacc gttgacattg tcaacatctt tcagaatgat      60
gtggagttct ccctcgtaaa tgagatccat aagggtatta gtcctcccgc tggcgttagg     120
aagtcaatgc caacgatgct tctttacgat gccaatggcc tcaagctttt tgagaacatc     180
acctatgtga aggagtatta tctaacaaat gcggaaattg aggtcttgga gacaaattcc     240
aggaggatag ttgaacggat tccagacaat gcgcaactgc ttgaattagg tagcgggtgc     300
gtcatccttc caaatcaaat cgtaaccttt caggctgcgt agcgtatcat taccgttctc     360
cggttttaac cgccttttag gaatcttcgg aaaattgaga ttctgctacg ggagtttgag     420
cgcgtgggaa agcgcgtgga ttattatgcc ctggacctgt ctctatcaga actgcagcgc     480
acattcgcag aggtgtccat tgatgattac acacacgttg gcctccatgg tctccatgga     540
acctacgatg atgccgtcac ttggcttaac agccccgaaa acaggaagcg cccacggtg      600 atcatgtcta tggttcctc tttagggaac tttgaccgtc ccggcgcagc aaagtttctc     660
tcgcagtatg ctagccttct tggtccatcc gatatgatga tcattggtct ggatggctgc     720
aaggacccgg gcaaagtata cagggcatac aatgattcag aaggtgttac acggcagttc     780
tacgagaacg gactagtgca tgcaaatgtt gttcttggat acgaagcctt caaatctgat     840
gagtgggaag tagtgactga ctacgatacc gtggagggac gacactgggc agcctactca     900
cccaagaagg acgtcactat caacgggtc cttcttaaga agggtgagaa actttctctt     960
gaagaggcgt acaagtacgg accagaggaa cgcgatcaac tgtggcgtga tgccaagtta    1020
attcagtcta cggaaatggg caatgggtct gacgattacc gtgagtagca aatggctgcc    1080
tcatttcaat agacgtgtat gctgactctg gcttttcgca aaatagatct ccatcttctg    1140
acatcggcta ccctcaacct ccccacgtct ccctctcaat atgcagctca tcctataccc    1200
agctttgaag aatggcagtc cctgtggaca gcatgggata atgctacaaa ggctatggtc    1260
cctcgcgagg agcttctgtc aaagccgatc aagctacgga actctttgat cttctatctg    1320
ggacacattc ctacattctt gggttagtct acatggctta ctattcccaa cacatagctt    1380
gatgctaatt atgcaaacag acatccatct gacccgagcc ctgcgcggaa aattaacaga    1440
gccaaagtct tataaactaa ttttcgaacg tgggattgat cctgatgtag atgacccga     1500 gaagtgccac tcccatagcg agatcccaga cgagtggcca gctcttgatg acattctaga    1560
ctaccaagag cgagtcagaa gcagagttag atccatctac caaatcgagg gccttgcaga    1620
gaacagaatc ctgggtgagg cgctttggat tggatttgag cacgaagtga tgcacctcga    1680
gacattcctg tacatgttga tccagagcga aaggatactt cccccgcccg ccactgagcg    1740
gccggacttc aaaaaactgt atcaagaagc tcggagaagc atgaaagcaa atgagtggtt    1800
ctctgttcct gaacagacac ttactattgg ccttgatggt gctgatacca acgacgtacc    1860
cccaacgacc tatgggtggg acaatgagaa acctgcgaga acagtcacgg ttccagcatt    1920
tgaggcgcag ggcaggccca tcaccaatgg tgagtacgcc aagtacttgc aagcgaatca    1980
gtcgcgcaga aggccagcat catgggtcct gacccattcg gatgaagact acgccatacc    2040
```

-continued

| | |
|---|---|
| tatggcggtc aacggaagca gtgtcggggc tacgcaggac tttatgtcca actttgctgt | 2100 |
| ccgtacggtc ttcggcccag ttccacttga atttgctcag gactggcctg tgatggcgtc | 2160 |
| atatgatgaa ttagctgaat acgccgaatg ggtgggttgc aggatcccaa ccttcgaaga | 2220 |
| gacaaggagt atctatctgc actcagcgct attgaaggaa agaggtggcg tgaatcataa | 2280 |
| tggggagccc aacggccata ggttagtgca gcctcattat aacaccacat tcgggattaa | 2340 |
| gctgagctaa cggctgtcag tttgaacggc gatctgaatg gggtgaatgg aaatggttac | 2400 |
| tcgaagatca acccaggcaa acctcgtaag ccggatcacc agcctgtaca atatccttcc | 2460 |
| cgagacgccc tgccagtgtt ccttgatctg cacggtctca acgtcgggtt caagcactgg | 2520 |
| caccccaccc cagttatcca aacggcgat cgactcgccg gtcagggtga actgggaggc | 2580 |
| gcatgggagt ggactagcac gccattagcg ccacacgatg gctttaaagc catggagatc | 2640 |
| tacccgggat acacctgtaa gtaccagtcc cgttatcggg taccctctaa aagtctatca | 2700 |
| ttacatacta attccgcaca gccgatttct tcgacggtaa acataatatc atcctgggtg | 2760 |
| gttcttgggc tactcatccc cgcgtcgctg ggcgtaccac tttgtaagtt taccggtata | 2820 |
| gaactcgggg cactataaga tgctgacatc acctctagcg tcaattggta ccagcacaac | 2880 |
| tatccttaca cctgggcagg agcacgcctg gtgcgggatc tttag | 2925 |

<210> SEQ ID NO 2
<211> LENGTH: 1770
<212> TYPE: DNA
<213> ORGANISM: Aspergillus sojae

<400> SEQUENCE: 2

| | |
|---|---|
| atgtctaatg ttacccaatc agccttgaga caggcaactc gcgcctacgc tcgccgactg | 60 |
| ccatcgacgc agcatggctc cttcgcttcc gcccttccca gacgggcgct cgccactcca | 120 |
| tacagacggt tctatgtctc cgaaactaag gctggaaatg ctcaggtttc ggtagatacc | 180 |
| gctatgaagc aggagcagaa ggaattcatg aaacaaactg gggtgcagcc gcagaaggtg | 240 |
| gagctcccta gttctggtgt ttccggcgat gcctcgatga gccgtctgc cggcatcctc | 300 |
| aagcaggcca ctgtcatgga ccaaggaacg cgaccgatct atctcgatat gcaggccaca | 360 |
| accccaacgg atccccgtgt tctcgacgcc atgctcccct tcttgaccgg aatttacggc | 420 |
| aaccctcatt cgagaaccca tgcatacggt tgggagtcag aaaaggcagt cgagcaatcc | 480 |
| cgagagcata tcgccaagct gatcggcgcg gacccgaaag agatcatctt cactagcggt | 540 |
| gctactgaga gtaacaacat gagcattaag ggtgtggcga ggttttttgg gcgctccggc | 600 |
| aaaaaaaacc acatcatcac aacgcagacc gagcacaagt gtgttcttga cagctgtcgg | 660 |
| catcttcagg atgagggcta cgaggttacg tatctccccg tgcagaacaa cggcttgatt | 720 |
| cggatggaag acctcgaggc cgccattcgc cctgaaacgg ccctggtcag catcatggcc | 780 |
| gtcaacaatg agatcggtgt tatccagccc ctggaacaga ttggaaagtt gtgccgctcc | 840 |
| aagaagattt tcttccacac ggacgctgca caggccgtgg gaaagatccc gttggatgtg | 900 |
| aataaattga atattgattt gatgtctatt tcgagccaca agatttacgg ccccaagggt | 960 |
| attggagctt gctatgtcag acgtcgtccc agggttcgcc ttgaccctct cattactgga | 1020 |
| ggtggacagg agcgaggcct gcgcagtggt actcttgctc ctcatctggt cgttgggttc | 1080 |
| ggtgaggcct gccggatcgc cgcccaagat atggaggtac gttctatttt tcttttgttt | 1140 |
| ctgcttactt gcaatcccctt ttctattttc cgatgattat atactgcaaa tatggatttc | 1200 |

-continued

```
cgagaccggt gggggtagct gcacgcctaa cgcgtgaccc atgggcctat gacgtctcag    1260 cagggggtgat gagttgacta ttgctttgtt tgccttgttt gcctcatgcg gctatgcgtc    1320
agtggacatc gctaatcgag ttggcagtat gacaccaagc acattgatcg tttgtccaag    1380
cgcctgaccg acgggctcct atccatggag cacacacacc tcaacggaga ccctgaacat    1440
cactacccgg gatgtgtcaa tgtctccttt gcctacatcg aaggagagtc tctcctgatg    1500
gccttgaaag acattgctct gtcgtcgggt agtgcctgta cctctgcgtc attggagccc    1560
agctacgtcc ttcgtgcctt gggtagcagt gacgagagcg cccatagcag tatccggttt    1620
ggaattggac gattcacttc ggatagcgaa attgactacg tgctgaaggc ggtacaggac    1680
cgcgttcatt tcctacgcga gctgagcccc ttgtgggaat tggtgcagga aggtatcgac    1740
ctgaacacga tcgaatggag tcaacattaa                                      1770
```

<210> SEQ ID NO 3
<211> LENGTH: 1529
<212> TYPE: DNA
<213> ORGANISM: Aspergillus sojae

<400> SEQUENCE: 3

```
atgaccactc ccttcggagc tcccatgaga gagcacttcc tctttgacac caacttcaaa     60
aacctcaacc atggtatagt atcctactcc agtaacaagt accaacatta gctaactata    120
aaccaggctc cttcggcaca taccccgtg ccgtccagac agtcctccgc caacaccaac    180
actccgccga ggcccgtcca gacctcttct accgcatcac ccgcggccaa ggcatcgacg    240
gatcgcgccg catcgtagcc aacctgctca acatccccgt caacgaatgt gtcttcgtca    300
agaacgcaac cacggggtc gccaccgtgc tccgtaatct agtcttccag aagggagacg    360
cagtcgtgta cttcgacact atctatggcg ctgtggagaa gaatgtacac tctattatgg    420
aggctagtcc tgtgactact cgaaaggttg agtgtgcgtt acccgttagc catgaggacc    480
tggtgaaacg gttcagggat gtcgtgagtc gtgcaagagg ggaagggctg catgtgaaag    540
ttgcggtgtt tgacaccatc gtcagtgtgc ctggggtcag gttcccgttc agaccttgg    600 taggggtctg tcgggaggag ggtatactca gtcttatcga tggggcgcat ggtattggac    660
atataccgtt ggatttgggg actttgaggc cggatttctt tactagtaac ctgcataagt    720
atgttccttt ccccttttctt tctttctttc gtttgattac tgtgtgagga tcttgtatgc    780
tgatatagag caaaaaaaaa agatggctat tcgtcccccg cggctgcgca gttctccacg    840
tcccactccg caaccaacat ctcatccgca ccacattccc aacctcatgg ggatacatcc    900
ccctcccctc atccggggag ataaccccca ccgccacgca gggtaaatcc gccttcgaat    960
atctcttcga acacatctcc acaaccgacg acacgccctg ctatgcgtc cccgccgcca    1020 tgaaattccg aactgaagtc tgcggcggcg aagaccgcat ctacgcttac ctggagaccc    1080
tagcccgcga ggccggggat atcgttgccc gcgcccctgg gacggaagtc atgcaggagc    1140
ccgggttgaa ggagggagag gtgagtcagc ttaggaggtg tgggatggct actgtgcggt    1200
tgccgattgc tgtgacttct tcttcttctt ctgattctgg gtctggtaat ggtggggtg    1260 ctgttatgag ggtgcaggt gaggatggga gttcgtattt gcgaatccag acgtctttgg    1320
tggggactgt gagtaattgg tttcgggata cgttgtttga taagtacgag acgtttgtgc    1380
cggtgttcca gcatgggggg tggttgtgga cgagactcag tgcgcaggtt tatttggaga    1440
agggggattt tgagtggttg gggggtgttt tgagggagtg ttgtgagagg gttgagaggg    1500
aggttggggt ttcttctgcg aagctttga                                       1529
```

<210> SEQ ID NO 4
<211> LENGTH: 845
<212> TYPE: PRT
<213> ORGANISM: Aspergillus sojae

<400> SEQUENCE: 4

```
Met Ser Pro Leu Ala Leu Ser Pro Lys Thr Val Asp Ile Val Asn Ile
1               5                   10                  15

Phe Gln Asn Asp Val Glu Phe Ser Leu Val Asn Glu Ile His Lys Gly
            20                  25                  30

Ile Ser Pro Pro Ala Gly Val Arg Lys Ser Met Pro Thr Met Leu Leu
        35                  40                  45

Tyr Asp Ala Asn Gly Leu Lys Leu Phe Glu Asn Ile Thr Tyr Val Lys
    50                  55                  60

Glu Tyr Tyr Leu Thr Asn Ala Glu Ile Glu Val Leu Glu Thr Asn Ser
65                  70                  75                  80

Arg Arg Ile Val Glu Arg Ile Pro Asp Asn Ala Gln Leu Leu Glu Leu
                85                  90                  95

Gly Ser Gly Asn Leu Arg Lys Ile Glu Ile Leu Leu Arg Glu Phe Glu
            100                 105                 110

Arg Val Gly Lys Arg Val Asp Tyr Tyr Ala Leu Asp Leu Ser Leu Ser
        115                 120                 125

Glu Leu Gln Arg Thr Phe Ala Glu Val Ser Ile Asp Asp Tyr Thr His
    130                 135                 140

Val Gly Leu His Gly Leu His Gly Thr Tyr Asp Asp Ala Val Thr Trp
145                 150                 155                 160

Leu Asn Ser Pro Glu Asn Arg Lys Arg Pro Thr Val Ile Met Ser Met
                165                 170                 175

Gly Ser Ser Leu Gly Asn Phe Asp Arg Pro Gly Ala Ala Lys Phe Leu
            180                 185                 190

Ser Gln Tyr Ala Ser Leu Leu Gly Pro Ser Asp Met Met Ile Ile Gly
        195                 200                 205

Leu Asp Gly Cys Lys Asp Pro Gly Lys Val Tyr Arg Ala Tyr Asn Asp
    210                 215                 220

Ser Glu Gly Val Thr Arg Gln Phe Tyr Glu Asn Gly Leu Val His Ala
225                 230                 235                 240

Asn Val Val Leu Gly Tyr Glu Ala Phe Lys Ser Asp Glu Trp Glu Val
                245                 250                 255

Val Thr Asp Tyr Asp Thr Val Glu Gly Arg His Trp Ala Ala Tyr Ser
            260                 265                 270

Pro Lys Lys Asp Val Thr Ile Asn Gly Val Leu Leu Lys Lys Gly Glu
        275                 280                 285

Lys Leu Phe Phe Glu Glu Ala Tyr Lys Tyr Gly Pro Glu Glu Arg Asp
    290                 295                 300

Gln Leu Trp Arg Asp Ala Lys Leu Ile Gln Ser Thr Glu Met Gly Asn
305                 310                 315                 320

Gly Ser Asp Asp Tyr His Leu His Leu Leu Thr Ser Ala Thr Leu Asn
                325                 330                 335

Leu Pro Thr Ser Pro Ser Gln Tyr Ala Ala His Pro Ile Pro Ser Phe
            340                 345                 350

Glu Glu Trp Gln Ser Leu Trp Thr Ala Trp Asp Asn Ala Thr Lys Ala
        355                 360                 365
```

```
Met Val Pro Arg Glu Glu Leu Leu Ser Lys Pro Ile Lys Leu Arg Asn
    370                 375                 380

Ser Leu Ile Phe Tyr Leu Gly His Ile Pro Thr Phe Leu Asp Ile His
385                 390                 395                 400

Leu Thr Arg Ala Leu Arg Gly Lys Leu Thr Glu Pro Lys Ser Tyr Lys
                405                 410                 415

Leu Ile Phe Glu Arg Gly Ile Asp Pro Asp Val Asp Asp Pro Glu Lys
                420                 425                 430

Cys His Ser His Ser Glu Ile Pro Asp Glu Trp Pro Ala Leu Asp Asp
                435                 440                 445

Ile Leu Asp Tyr Gln Glu Arg Val Arg Ser Arg Val Arg Ser Ile Tyr
    450                 455                 460

Gln Ile Glu Gly Leu Ala Glu Asn Arg Ile Leu Gly Glu Ala Leu Trp
465                 470                 475                 480

Ile Gly Phe Glu His Glu Val Met His Leu Glu Thr Phe Leu Tyr Met
                485                 490                 495

Leu Ile Gln Ser Glu Arg Ile Leu Pro Pro Ala Thr Glu Arg Pro
                500                 505                 510

Asp Phe Lys Lys Leu Tyr Gln Glu Ala Arg Arg Ser Met Lys Ala Asn
                515                 520                 525

Glu Trp Phe Ser Val Pro Glu Gln Thr Leu Thr Ile Gly Leu Asp Gly
    530                 535                 540

Ala Asp Thr Asn Asp Val Pro Pro Thr Thr Tyr Gly Trp Asp Asn Glu
545                 550                 555                 560

Lys Pro Ala Arg Thr Val Thr Val Pro Ala Phe Glu Ala Gln Gly Arg
                565                 570                 575

Pro Ile Thr Asn Gly Glu Tyr Ala Lys Tyr Leu Gln Ala Asn Gln Ser
                580                 585                 590

Arg Arg Arg Pro Ala Ser Trp Val Leu Thr His Ser Asp Glu Asp Tyr
    595                 600                 605

Ala Ile Pro Met Ala Val Asn Gly Ser Ser Val Gly Ala Thr Gln Asp
    610                 615                 620

Phe Met Ser Asn Phe Ala Val Arg Thr Val Phe Gly Pro Val Pro Leu
625                 630                 635                 640

Glu Phe Ala Gln Asp Trp Pro Val Met Ala Ser Tyr Asp Glu Leu Ala
                645                 650                 655

Glu Tyr Ala Glu Trp Val Gly Cys Arg Ile Pro Thr Phe Glu Glu Thr
                660                 665                 670

Arg Ser Ile Tyr Leu His Ser Ala Leu Leu Lys Glu Arg Gly Gly Val
    675                 680                 685

Asn His Asn Gly Glu Pro Asn Gly His Ser Leu Asn Gly Asp Leu Asn
    690                 695                 700

Gly Val Asn Gly Asn Gly Tyr Ser Lys Ile Asn Pro Gly Lys Pro Arg
705                 710                 715                 720

Lys Pro Asp His Gln Pro Val Gln Tyr Pro Ser Arg Asp Ala Leu Pro
                725                 730                 735

Val Phe Leu Asp Leu His Gly Leu Asn Val Gly Phe Lys His Trp His
                740                 745                 750

Pro Thr Pro Val Ile Gln Asn Gly Asp Arg Leu Ala Gly Gln Gly Glu
    755                 760                 765

Leu Gly Gly Ala Trp Glu Trp Thr Ser Thr Pro Leu Ala Pro His Asp
    770                 775                 780
```

```
Gly Phe Lys Ala Met Glu Ile Tyr Pro Gly Tyr Thr Ser Asp Phe Phe
785                 790                 795                 800

Asp Gly Lys His Asn Ile Ile Leu Gly Gly Ser Trp Ala Thr His Pro
                805                 810                 815

Arg Val Ala Gly Arg Thr Thr Phe Val Asn Trp Tyr Gln His Asn Tyr
            820                 825                 830

Pro Tyr Thr Trp Ala Gly Ala Arg Leu Val Arg Asp Leu
        835                 840                 845

<210> SEQ ID NO 5
<211> LENGTH: 512
<212> TYPE: PRT
<213> ORGANISM: Aspergillus sojae

<400> SEQUENCE: 5

Met Ser Asn Val Thr Gln Ser Ala Leu Arg Gln Ala Thr Arg Ala Tyr
1               5                   10                  15

Ala Arg Arg Leu Pro Ser Thr Gln His Gly Ser Phe Ala Ser Ala Leu
            20                  25                  30

Pro Arg Arg Ala Leu Ala Thr Pro Tyr Arg Arg Phe Tyr Val Ser Glu
        35                  40                  45

Thr Lys Ala Gly Asn Ala Gln Val Ser Val Asp Thr Ala Met Lys Gln
    50                  55                  60

Glu Gln Lys Glu Phe Met Lys Gln Thr Gly Val Gln Pro Gln Lys Val
65                  70                  75                  80

Glu Leu Pro Ser Ser Gly Val Ser Gly Asp Ala Ser Met Ser Pro Ser
                85                  90                  95

Ala Gly Ile Leu Lys Gln Ala Thr Val Met Asp Gln Gly Thr Arg Pro
            100                 105                 110

Ile Tyr Leu Asp Met Gln Ala Thr Thr Pro Thr Asp Pro Arg Val Leu
        115                 120                 125

Asp Ala Met Leu Pro Phe Leu Thr Gly Ile Tyr Gly Asn Pro His Ser
    130                 135                 140

Arg Thr His Ala Tyr Gly Trp Glu Ser Glu Lys Ala Val Glu Gln Ser
145                 150                 155                 160

Arg Glu His Ile Ala Lys Leu Ile Gly Ala Asp Pro Lys Glu Ile Ile
                165                 170                 175

Phe Thr Ser Gly Ala Thr Glu Ser Asn Asn Met Ser Ile Lys Gly Val
            180                 185                 190

Ala Arg Phe Phe Gly Arg Ser Gly Lys Lys Asn His Ile Ile Thr Thr
        195                 200                 205

Gln Thr Glu His Lys Cys Val Leu Asp Ser Cys Arg His Leu Gln Asp
    210                 215                 220

Glu Gly Tyr Glu Val Thr Tyr Leu Pro Val Gln Asn Asn Gly Leu Ile
225                 230                 235                 240

Arg Met Glu Asp Leu Glu Ala Ala Ile Arg Pro Glu Thr Ala Leu Val
                245                 250                 255

Ser Ile Met Ala Val Asn Asn Glu Ile Gly Val Ile Gln Pro Leu Glu
            260                 265                 270

Gln Ile Gly Lys Leu Cys Arg Ser Lys Lys Ile Phe Phe His Thr Asp
        275                 280                 285

Ala Ala Gln Ala Val Gly Lys Ile Pro Leu Asp Val Asn Lys Leu Asn
    290                 295                 300

Ile Asp Leu Met Ser Ile Ser Ser His Lys Ile Tyr Gly Pro Lys Gly
305                 310                 315                 320
```

```
Ile Gly Ala Cys Tyr Val Arg Arg Pro Arg Val Arg Leu Asp Pro
                325                 330                 335

Leu Ile Thr Gly Gly Gln Glu Arg Gly Leu Arg Ser Gly Thr Leu
            340                 345                 350

Ala Pro His Leu Val Gly Phe Gly Glu Ala Cys Arg Ile Ala Ala
        355                 360                 365

Gln Asp Met Glu Tyr Asp Thr Lys His Ile Asp Arg Leu Ser Lys Arg
    370                 375                 380

Leu Thr Asp Gly Leu Leu Ser Met Glu His Thr His Leu Asn Gly Asp
385                 390                 395                 400

Pro Glu His His Tyr Pro Gly Cys Val Asn Val Ser Phe Ala Tyr Ile
                405                 410                 415

Glu Gly Glu Ser Leu Leu Met Ala Leu Lys Asp Ile Ala Leu Ser Ser
            420                 425                 430

Gly Ser Ala Cys Thr Ser Ala Ser Leu Glu Pro Ser Tyr Val Leu Arg
        435                 440                 445

Ala Leu Gly Ser Ser Asp Glu Ser Ala His Ser Ser Ile Arg Phe Gly
    450                 455                 460

Ile Gly Arg Phe Thr Ser Asp Ser Glu Ile Asp Tyr Val Leu Lys Ala
465                 470                 475                 480

Val Gln Asp Arg Val His Phe Leu Arg Glu Leu Ser Pro Leu Trp Glu
                485                 490                 495

Leu Val Gln Glu Gly Ile Asp Leu Asn Thr Ile Glu Trp Ser Gln His
            500                 505                 510

<210> SEQ ID NO 6
<211> LENGTH: 463
<212> TYPE: PRT
<213> ORGANISM: Aspergillus sojae

<400> SEQUENCE: 6

Met Thr Thr Pro Phe Gly Ala Pro Met Arg Glu His Phe Leu Phe Asp
1               5                   10                  15

Thr Asn Phe Lys Asn Leu Asn His Gly Ser Phe Gly Thr Tyr Pro Arg
            20                  25                  30

Ala Val Gln Thr Val Leu Arg Gln His Gln His Ser Ala Glu Ala Arg
        35                  40                  45

Pro Asp Leu Phe Tyr Arg Ile Thr Arg Gly Gln Gly Ile Asp Gly Ser
    50                  55                  60

Arg Arg Ile Val Ala Asn Leu Leu Asn Ile Pro Val Asn Glu Cys Val
65                  70                  75                  80

Phe Val Lys Asn Ala Thr Thr Gly Val Ala Thr Val Leu Arg Asn Leu
                85                  90                  95

Val Phe Gln Lys Gly Asp Ala Val Val Tyr Phe Asp Thr Ile Tyr Gly
            100                 105                 110

Ala Val Glu Lys Asn Val His Ser Ile Met Glu Ala Ser Pro Val Thr
        115                 120                 125

Thr Arg Lys Val Glu Cys Ala Leu Pro Val Ser His Glu Asp Leu Val
    130                 135                 140

Lys Arg Phe Arg Asp Val Val Ser Arg Ala Arg Gly Glu Gly Leu His
145                 150                 155                 160

Val Lys Val Ala Val Phe Asp Thr Ile Val Ser Val Pro Gly Val Arg
                165                 170                 175
```

```
Phe Pro Phe Glu Thr Leu Val Gly Val Cys Arg Glu Gly Ile Leu
            180                 185                 190

Ser Leu Ile Asp Gly Ala His Gly Ile Gly His Ile Pro Leu Asp Leu
        195                 200                 205

Gly Thr Leu Arg Pro Asp Phe Phe Thr Ser Asn Leu His Lys Trp Leu
    210                 215                 220

Phe Val Pro Arg Gly Cys Ala Val Leu His Val Pro Leu Arg Asn Gln
225                 230                 235                 240

His Leu Ile Arg Thr Thr Phe Pro Thr Ser Trp Gly Tyr Ile Pro Pro
                245                 250                 255

Pro Ser Ser Gly Glu Ile Thr Pro Thr Ala Thr Gln Gly Lys Ser Ala
            260                 265                 270

Phe Glu Tyr Leu Phe Glu His Ile Ser Thr Thr Asp Asp Thr Pro Trp
        275                 280                 285

Leu Cys Val Pro Ala Ala Met Lys Phe Arg Thr Glu Val Cys Gly Gly
    290                 295                 300

Glu Asp Arg Ile Tyr Ala Tyr Leu Glu Thr Leu Ala Arg Glu Ala Gly
305                 310                 315                 320

Asp Ile Val Ala Arg Ala Leu Gly Thr Glu Val Met Gln Glu Pro Gly
                325                 330                 335

Leu Lys Glu Gly Glu Val Ser Gln Leu Arg Arg Cys Gly Met Ala Thr
            340                 345                 350

Val Arg Leu Pro Ile Ala Val Thr Ser Ser Ser Ser Asp Ser Gly
        355                 360                 365

Ser Gly Asn Gly Gly Gly Ala Val Met Arg Val Gln Gly Glu Asp Gly
    370                 375                 380

Ser Ser Tyr Leu Arg Ile Gln Thr Ser Leu Val Gly Thr Val Ser Asn
385                 390                 395                 400

Trp Phe Arg Asp Thr Leu Phe Asp Lys Tyr Glu Thr Phe Val Pro Val
                405                 410                 415

Phe Gln His Gly Gly Trp Leu Trp Thr Arg Leu Ser Ala Gln Val Tyr
            420                 425                 430

Leu Glu Lys Gly Asp Phe Glu Trp Leu Gly Gly Val Leu Arg Glu Cys
        435                 440                 445

Cys Glu Arg Val Glu Arg Glu Val Gly Val Ser Ser Ala Lys Leu
    450                 455                 460

<210> SEQ ID NO 7
<211> LENGTH: 748
<212> TYPE: DNA
<213> ORGANISM: Aspergillus sojae

<400> SEQUENCE: 7
tgtggaccag acaggcgcca ctcggccggg ccacaactgc ttgggttttg accgggagcg     60
gaccaattaa ggactcgaac gaccgcgggg ttcaaatgca acaagtaca acacgcagca    120 aacgaagcag cccaccactg cgttgatgcc cagtttgtct gtccgaaatc caccggaaag    180
gtggaaacat actatgtaac aatcagaggg aagaaaaatt ttttatcgac gaggcaggat    240
agtgactgat ggtggggtca tggtcgggtc tccgagcgaa agagaaccaa ggaaacaaga    300
tcaacgaggt tggtgtaccc aaaaggccgc agcaacaaga gtcatcgccc aaaagtcaac    360
agtctggaag agactccgcc gtgcagattc tgcgtcggtc ccgcacatgc gtggtggggg    420
cattacccct ccatgtccaa tgataagggc ggcggtcgag ggcttaagcc cgcccactaa    480
```

| | |
|---|---:|
| ttcgccttct cgcttgcccc tccatataag gattcccctc cttcccctcc cacaactttt | 540 |
| ttcctctttc tctcttcgtc cgcatcagta cgtatatctt tcccccctac ctctttctca | 600 |
| ctcttcctcg attcattcca ctcttctcct tactgacatc tgttttgctc agtacctcta | 660 |
| cgcgatcagc cgtagtatct gagcaagctt ttttacagaa tctttctagt atcttacaaa | 720 |
| gaactacaaa gttcgcacca ccttcaaa | 748 |

<210> SEQ ID NO 8
<211> LENGTH: 800
<212> TYPE: DNA
<213> ORGANISM: Aspergillus sojae

<400> SEQUENCE: 8

| | |
|---|---:|
| gtaccaggag tacattggag agttctacca ttgttgctgg aatacaatga tgattagaaa | 60 |
| ccgaagagtg ttatgattcg gacggatata cgcatggcac gcatacagcg tgatacatag | 120 |
| gctgtttgct caagaattag gattttatct gaatccatgt acagagttta cttatgttag | 180 |
| tagtcaatga aatcttggct ttctaatttt gtccgatcta caaggggtag tcgatcacag | 240 |
| aacgaactag atgtgcaggg aacgatgatc acccgctctt agcaagacct ctagtagttt | 300 |
| tcgaccatag ctttaacgcg aatcatgacc ctactatttt ctagattgca gaccaagtca | 360 |
| catgacaatg tcctctttga gtaggatca gtagctgatt agattccggg aaatgaatta | 420 |
| gggctggcgt tccaactact ggggagtgcc gatgttgctg tatgaaagat gtaagatta | 480 |
| ctagtgcaca gctgtagtaa ttatttactc tagattatat attccaaata ataagtaatc | 540 |
| taagatagta gacagtccta tgatatagct ccgggttcga agtcggcaaa agatatgcaa | 600 |
| tcacctgtcg ggatgatata tgtatatctg aaataccgac atcaaccatc cagtcggatc | 660 |
| agctaaacga agtatcactt ctttcgccac tgccaatcac tacttctatt aaagttcatg | 720 |
| ttacagtata agccacaaga cttatctcca gaactaactt gtgcatagga gctctgccga | 780 |
| tagccgggtg gttggatcgg | 800 |

<210> SEQ ID NO 9
<211> LENGTH: 1838
<212> TYPE: DNA
<213> ORGANISM: Aspergillus sojae

<400> SEQUENCE: 9

| | |
|---|---:|
| ttgggcttat tgctatgtcc ctgaaaggat atcaaaagca ggcaaaaagc caggcataac | 60 |
| cccgcgcgga tggtacccta aggataagcc ctaatcttat ctacatgtga ctgcgtcgat | 120 |
| gtgtttggtc caaatgaggc atgtggctca ccccacaggc ggagaaacgt gtggctagtg | 180 |
| catgacggtc ccctccatag attcaattta atttttcgcg gcaattgtcg tgcagtttgt | 240 |
| atctaccgtt cattctacat attaagggtt agtaattgga catcctgatt actttgtcta | 300 |
| attactgaaa actcgaagta ctaacctact aaataagtca gtttcaacca ctaagtactc | 360 |
| atttatacaa tagttgcaga accccgcgct acccctccat tgccaacatg tcttccaagt | 420 |
| cgcaattgac ctacagcgca cgcgctagca agcaccccaa tgcgctcgtg aagaagctct | 480 |
| tcgaggttgc cgaggccaag aaaaccaatg tcaccgtttc cgccgacgtg acaaccacca | 540 |
| aagagctgct ggatttggct gaccgtatgc gcaccgggga tgccacttac atatgatcta | 600 |
| gtaatggtta atggtggaat atataacagg actcggtccg tacattgccg tgatcaaaac | 660 |
| tcacatcgat atcctctccg atttcagcga agagaccatc atcggtctga aggcccttgc | 720 |
| agagaagcac aatttcctca tcttcgaaga tcgcaagttc atcgatatcg gaaacacagt | 780 |

```
ccaaaagcag taccatggcg gcactctgcg catctctgag tgggcccaca tcatcaactg    840
cagtattctg cccggtgagg gtatcgtcga ggctctggcc cagactgctt cggccgagga    900
cttcccctat ggctctgaga ggggccttt gatccttgcg gagatgacat ccaagggatc    960
tttggctacc ggtcaatata ctacttcttc tgttgactat gcccggaagt ataagaagtt    1020
tgtgatggga ttcgtctcga cgcgtcacct gggcgaggtt cagtctgaag ttagctcgcc    1080
ttcggaggag gaggatttcg tcgtcttcac gacaggtgtc aacctctcct cgaagggaga    1140
caaactggga cagcaatacc agactcctga gtctgctgtt ggacgcggtg ccgactttat    1200
cattgctggt cgtggaattt atgctgctcc tgatcccgtg gaggcagcga agcggtacca    1260
gaaagaggga tgggatgcat accagaagcg tgttggtgcg caataagtag tggtgaatac    1320
gtgctctttt tatggcagta tatcgcaagt atgatgcgat tcataaattc agcagtcgaa    1380
ttctacgaga gaacgatgct aagagatacc ctctctatat gaataatatg cctgcctcga    1440
gatatggaca tattcaagat cagagttaag ggtcatgttt caaaatcaca ccaatctcca    1500
acatagacga gaattttttac cggattgtct gaaggtgcag ctggagattg gtctattttc    1560
taagagtggg gtatcactaa tgtacagtcg gtcactatcg tacaaacaat cacaattata    1620
tacaagattt cccatcaccc cttactctaa catggcactt ttatccatcg agtccgagcc    1680
tagccaccat ttggtgcttt cgtagagacc aaagtataac cctgatccga cagcggccat    1740
aaacgtgttg atagcacacc ctcggaatag tcctctcggg ccatctgttc gtataatctc    1800
ccgtacggta ttgatcatcc ttttcttctg aggtgcgg                           1838

<210> SEQ ID NO 10
<211> LENGTH: 38
<212> TYPE: DNA
<213> ORGANISM: Artificial sequence
<220> FEATURE:
<223> OTHER INFORMATION: Primer

<400> SEQUENCE: 10
cggtacccgg ggatctgtgg accagacagg cgccactc                            38

<210> SEQ ID NO 11
<211> LENGTH: 40
<212> TYPE: DNA
<213> ORGANISM: Artificial sequence
<220> FEATURE:
<223> OTHER INFORMATION: Primer

<400> SEQUENCE: 11
atgtactcct ggtactttga aggtggtgcg aactttgtag                          40

<210> SEQ ID NO 12
<211> LENGTH: 28
<212> TYPE: DNA
<213> ORGANISM: Artificial sequence
<220> FEATURE:
<223> OTHER INFORMATION: Primer

<400> SEQUENCE: 12
gtaccaggag tacattggag agttctac                                       28

<210> SEQ ID NO 13
<211> LENGTH: 23
<212> TYPE: DNA
<213> ORGANISM: Artificial sequence
<220> FEATURE:
```

<223> OTHER INFORMATION: Primer

<400> SEQUENCE: 13
ccgatccaac cacccggcta tcg                                                    23

<210> SEQ ID NO 14
<211> LENGTH: 43
<212> TYPE: DNA
<213> ORGANISM: Artificial sequence
<220> FEATURE:
<223> OTHER INFORMATION: Primer

<400> SEQUENCE: 14
gggtggttgg atcggttggg cttattgcta tgtccctgaa agg                              43

<210> SEQ ID NO 15
<211> LENGTH: 39
<212> TYPE: DNA
<213> ORGANISM: Artificial sequence
<220> FEATURE:
<223> OTHER INFORMATION: Primer

<400> SEQUENCE: 15
cgactctaga ggatcccgca cctcagaaga aaaggatga                                   39

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
tttgaaggtg gtgcgaactt tgtag                                                  25

<210> SEQ ID NO 17
<211> LENGTH: 38
<212> TYPE: DNA
<213> ORGANISM: Artificial sequence
<220> FEATURE:
<223> OTHER INFORMATION: Primer

<400> SEQUENCE: 17
cgcaccacct tcaaaatgtc acctttggct ctctctcc                                    38

<210> SEQ ID NO 18
<211> LENGTH: 37
<212> TYPE: DNA
<213> ORGANISM: Artificial sequence
<220> FEATURE:
<223> OTHER INFORMATION: Primer

<400> SEQUENCE: 18
atgtactcct ggtacctaaa gatcccgcac caggcgt                                     37

<210> SEQ ID NO 19
<211> LENGTH: 44
<212> TYPE: DNA
<213> ORGANISM: Artificial sequence
<220> FEATURE:
<223> OTHER INFORMATION: Primer

<400> SEQUENCE: 19
cgcaccacct tcaaaatgtc taatgttacc caatcagcct tgag                             44

<210> SEQ ID NO 20
<211> LENGTH: 45
<212> TYPE: DNA
<213> ORGANISM: Artificial sequence
<220> FEATURE:
<223> OTHER INFORMATION: Primer

<400> SEQUENCE: 20

```
atgtactcct ggtacttaat gttgactcca ttcgatcgtg ttcag           45
```

<210> SEQ ID NO 21
<211> LENGTH: 36
<212> TYPE: DNA
<213> ORGANISM: Artificial sequence
<220> FEATURE:
<223> OTHER INFORMATION: Primer

<400> SEQUENCE: 21

```
cgcaccacct tcaaaatgac cactcccttc ggagct                     36
```

<210> SEQ ID NO 22
<211> LENGTH: 43
<212> TYPE: DNA
<213> ORGANISM: Artificial sequence
<220> FEATURE:
<223> OTHER INFORMATION: Primer

<400> SEQUENCE: 22

```
atgtactcct ggtactcaaa gcttcgcaga agaaacccca acc             43
```

<210> SEQ ID NO 23
<211> LENGTH: 2917
<212> TYPE: DNA
<213> ORGANISM: Aspergillus oryzae

<400> SEQUENCE: 23

```
atgtcaccgt tggctctttc tcctaagacc gttgacattg tcaacatctt tcagaatgac    60
gtggagttct ccctcgtaaa tgagatccat aagggcatta gtcctcccgc tggcgttagg   120
aagtcaatgc caacgatgct tctttacgat gccaatggcc tcaagctttt tgagaaaatc   180
acctatgtga aggagtatta tctaacaaat gcggaaatcg aggtcttgga cacaaattcc   240
aggaggatag ttgaacggat tccagacaat gcgcaactgc ttgaattagg tagcgggtgc   300
gtcatccttc caaatcaaat cgtaaccttt caggctgcgt agcgtatcat taccgttctc   360
cggttttaac cgccttttag gaatcttcgg aaaattgaga ttctgctacg ggagtttgag   420
cgcgtgggaa agcgcgtgga ttattatgcc cttgacctgt ctctatcaga actgcagcgc   480
acattcgcag aggtgtccat tgatgattac acacacgttg gcctccatgg tctccatgga   540
acctacgacg atgccgtcac ttggcttaac agccccgaaa acaggaagcg gcccacggtg   600
atcatgtcta tgggttcctc tttagggaac tttgaccgtc ctggcgcagc aaagtttctc   660
tcgcagtatg ctagccttct tggtccatcc gatatgatga tcattggtct ggatggctgc   720
aaggacccgg gcaaagtata cagggcatac aatgattcag aaggtgttac acggcagttc   780
tatgagaacg gactagtgca tgcaaatgtt gttcttggat acgaagcctt caaacctgat   840
gagtgggaag tagtgactga ctacgatgcc gtggaggac  gacactgggc agcctactca   900
cccaggaggg acgtcactat caacggggtc cttcttaaga aggggagaa  actcttcttt   960
gaagaggcgt acaagtacgg accagaggaa cgcgatcaac tgtggcgtga tgccaagtta  1020
ctccagtcta cggaagtggg caatgggtct gacgattacc gtgagtagca aatggctgcc  1080
```

-continued

```
tcatttcagt agacgtgtat gctaaatctg gcttttcgca aaatagatct ccatcttctg    1140
acatccgctg ccctcaacct ccccacgtct ccctctcaat atgcagctca tcctataccc    1200
agctttgaag aatggcagtc cctgtggaca gcatgggata atgctacaaa ggctatggtc    1260
cctcgcgagg agcttctgtc aaagccgatc aagctacgga actctttaat cttctatctg    1320
gggcacattc ctacattctt gggttagtct acatggctta ctattcccaa cacataactt    1380
gatgctaatt atgcaaacag acatccatct gacccgagcc ctgcgcggaa aactgacaga    1440
gccaaagtct tataaactaa ttttcgaacg tgggattgat cctgatgtag atgaccccca    1500
gaagtgccac tcccatagcg agatcccaga cgagtggcca gctcttgatg acattctaga    1560
ctaccaagag cgagtcagaa gcagagttag atccatctac cagatcgagg gccttgcaga    1620
aaacagaatc ctgggtgagg cgctttggat tggatttgag cacgaagtga tgcacctcga    1680
gacattcctg tacatgttga tccagagcga aaggatactt ccccgcccg ccactgaacg     1740 gccggacttc aaaaaactgt accaagacgc tcggagaagc atgaaaacaa atgagtggtt    1800
ctccgttcct gaacagacac ttactattgg ccttgatggt gctgatacca acgacgtacc    1860
cccaacgacc tatgggtggg acaatgagaa acctgcgaga acagtgacgg ttccagcatt    1920
tgaggcgcag ggcaggccca tcaccaatgg tgagtacgcc aagtacttgc aagcgaatca    1980
gtcgcgcaga aggccagcat catgggtcct gacccattcg gatgaaaact accccatacc    2040 tatgccgtc aacggaagca gtgtcggggc tacgcaggac tttatgtcca actttgctgt    2100
ccgtactgtc ttcggcccag ttccacttga atttgctcag gactggcctg tgatggcgtc    2160
atatgatgaa ttagccgaat atgccgaatg ggtgggttgc agaatcccaa ccttcgaaga    2220
gacaaggagt atctatctgc actcagcgct actgaaggaa agaggtggcg taaatcataa    2280
tggggagccc aatggccata ggttagtgca gcctcattat aacgccacat tccgggggatt   2340 gagctgagct aacggctttc agtgtgaacg gctatctgaa cgggatgaat ggaaatagct    2400
actcgaagat caacccaggc aaacctcgta cgccggacca ccagcctgta caatatcctt    2460
cccgggacgc cttgccagtg ttccttgatc tggacggtct caacgtcggg ttcaagcact    2520 ggcacccca cccagttatc cagaacggcg atcgactcgc cggtcagggt gaactgggag     2580
gcgcatggga gtggactagc acgccattag cgccacacga tggctttaaa gccatggaga    2640
tctacccggg atacacctgt aagtaccagt cccgttatcg ggtaccctct cattacatac    2700
taattccgca cagccgattt cttcgacggt aaacataaca tcatcctggg tggttcttgg    2760
gctactcatc cccgcgttgc tgggcgtacc actttgtaag tttaccggta tagaacccgg    2820
ggcactataa gatgctgaca cacctctag cgtcaattgg taccagcaca actatcctta    2880
cacctgggca ggagcacgcc tagtgcggga tctttag                             2917
```

<210> SEQ ID NO 24
<211> LENGTH: 845
<212> TYPE: PRT
<213> ORGANISM: Aspergillus oryzae

<400> SEQUENCE: 24

```
Met Ser Pro Leu Ala Leu Ser Pro Lys Thr Val Asp Ile Val Asn Ile
1               5                   10                  15

Phe Gln Asn Asp Val Glu Phe Ser Leu Val Asn Glu Ile His Lys Gly
            20                  25                  30

Ile Ser Pro Pro Ala Gly Val Arg Lys Ser Met Pro Thr Met Leu Leu
        35                  40                  45
```

```
Tyr Asp Ala Asn Gly Leu Lys Leu Phe Glu Lys Ile Thr Tyr Val Lys
        50                  55                  60

Glu Tyr Tyr Leu Thr Asn Ala Glu Ile Glu Val Leu Glu Thr Asn Ser
 65                  70                  75                  80

Arg Arg Ile Val Glu Arg Ile Pro Asp Asn Ala Gln Leu Leu Glu Leu
                85                  90                  95

Gly Ser Gly Asn Leu Arg Lys Ile Glu Ile Leu Leu Arg Glu Phe Glu
                100                 105                 110

Arg Val Gly Lys Arg Val Asp Tyr Tyr Ala Leu Asp Leu Ser Leu Ser
                115                 120                 125

Glu Leu Gln Arg Thr Phe Ala Glu Val Ser Ile Asp Asp Tyr Thr His
    130                 135                 140

Val Gly Leu His Gly Leu His Gly Thr Tyr Asp Asp Ala Val Thr Trp
145                 150                 155                 160

Leu Asn Ser Pro Glu Asn Arg Lys Arg Pro Thr Val Ile Met Ser Met
                165                 170                 175

Gly Ser Ser Leu Gly Asn Phe Asp Arg Pro Gly Ala Ala Lys Phe Leu
                180                 185                 190

Ser Gln Tyr Ala Ser Leu Leu Gly Pro Ser Asp Met Met Ile Ile Gly
    195                 200                 205

Leu Asp Gly Cys Lys Asp Pro Gly Lys Val Tyr Arg Ala Tyr Asn Asp
    210                 215                 220

Ser Glu Gly Val Thr Arg Gln Phe Tyr Glu Asn Gly Leu Val His Ala
225                 230                 235                 240

Asn Val Val Leu Gly Tyr Glu Ala Phe Lys Pro Asp Glu Trp Glu Val
                245                 250                 255

Val Thr Asp Tyr Asp Ala Val Glu Gly Arg His Trp Ala Ala Tyr Ser
                260                 265                 270

Pro Arg Arg Asp Val Thr Ile Asn Gly Val Leu Leu Lys Lys Gly Glu
                275                 280                 285

Lys Leu Phe Phe Glu Glu Ala Tyr Lys Tyr Gly Pro Glu Glu Arg Asp
    290                 295                 300

Gln Leu Trp Arg Asp Ala Lys Leu Leu Gln Ser Thr Glu Val Gly Asn
305                 310                 315                 320

Gly Ser Asp Asp Tyr His Leu His Leu Leu Thr Ser Ala Ala Leu Asn
                325                 330                 335

Leu Pro Thr Ser Pro Ser Gln Tyr Ala Ala His Pro Ile Pro Ser Phe
                340                 345                 350

Glu Glu Trp Gln Ser Leu Trp Thr Ala Trp Asp Asn Ala Thr Lys Ala
                355                 360                 365

Met Val Pro Arg Glu Glu Leu Leu Ser Lys Pro Ile Lys Leu Arg Asn
    370                 375                 380

Ser Leu Ile Phe Tyr Leu Gly His Ile Pro Thr Phe Leu Asp Ile His
385                 390                 395                 400

Leu Thr Arg Ala Leu Arg Gly Lys Leu Thr Glu Pro Lys Ser Tyr Lys
                405                 410                 415

Leu Ile Phe Glu Arg Gly Ile Asp Pro Asp Val Asp Pro Gln Lys
                420                 425                 430

Cys His Ser His Ser Glu Ile Pro Asp Glu Trp Pro Ala Leu Asp Asp
                435                 440                 445

Ile Leu Asp Tyr Gln Glu Arg Val Arg Ser Arg Val Ser Ile Tyr
450                 455                 460
```

Gln Ile Glu Gly Leu Ala Glu Asn Arg Ile Leu Gly Glu Ala Leu Trp
465                 470                 475                 480

Ile Gly Phe Glu His Glu Val Met His Leu Glu Thr Phe Leu Tyr Met
            485                 490                 495

Leu Ile Gln Ser Glu Arg Ile Leu Pro Pro Ala Thr Glu Arg Pro
        500                 505                 510

Asp Phe Lys Lys Leu Tyr Gln Asp Ala Arg Arg Ser Met Lys Thr Asn
            515                 520                 525

Glu Trp Phe Ser Val Pro Glu Gln Thr Leu Thr Ile Gly Leu Asp Gly
530                 535                 540

Ala Asp Thr Asn Asp Val Pro Pro Thr Thr Tyr Gly Trp Asp Asn Glu
545                 550                 555                 560

Lys Pro Ala Arg Thr Val Thr Val Pro Ala Phe Glu Ala Gln Gly Arg
                565                 570                 575

Pro Ile Thr Asn Gly Glu Tyr Ala Lys Tyr Leu Gln Ala Asn Gln Ser
                580                 585                 590

Arg Arg Arg Pro Ala Ser Trp Val Leu Thr His Ser Asp Glu Asn Tyr
                595                 600                 605

Pro Ile Pro Met Ala Val Asn Gly Ser Ser Val Gly Ala Thr Gln Asp
610                 615                 620

Phe Met Ser Asn Phe Ala Val Arg Thr Val Phe Gly Pro Val Pro Leu
625                 630                 635                 640

Glu Phe Ala Gln Asp Trp Pro Val Met Ala Ser Tyr Asp Glu Leu Ala
                645                 650                 655

Glu Tyr Ala Glu Trp Val Gly Cys Arg Ile Pro Thr Phe Glu Glu Thr
                660                 665                 670

Arg Ser Ile Tyr Leu His Ser Ala Leu Leu Lys Glu Arg Gly Gly Val
                675                 680                 685

Asn His Asn Gly Glu Pro Asn Gly His Ser Val Asn Gly Tyr Leu Asn
690                 695                 700

Gly Met Asn Gly Asn Ser Tyr Ser Lys Ile Asn Pro Gly Lys Pro Arg
705                 710                 715                 720

Thr Pro Asp His Gln Pro Val Gln Tyr Pro Ser Arg Asp Ala Leu Pro
                725                 730                 735

Val Phe Leu Asp Leu Asp Gly Leu Asn Val Gly Phe Lys His Trp His
                740                 745                 750

Pro Thr Pro Val Ile Gln Asn Gly Asp Arg Leu Ala Gly Gln Gly Glu
                755                 760                 765

Leu Gly Gly Ala Trp Glu Trp Thr Ser Thr Pro Leu Ala Pro His Asp
                770                 775                 780

Gly Phe Lys Ala Met Glu Ile Tyr Pro Gly Tyr Thr Ser Asp Phe Phe
785                 790                 795                 800

Asp Gly Lys His Asn Ile Ile Leu Gly Gly Ser Trp Ala Thr His Pro
                805                 810                 815

Arg Val Ala Gly Arg Thr Thr Phe Val Asn Trp Tyr Gln His Asn Tyr
                820                 825                 830

Pro Tyr Thr Trp Ala Gly Ala Arg Leu Val Arg Asp Leu
                835                 840                 845

<210> SEQ ID NO 25
<211> LENGTH: 38
<212> TYPE: DNA
<213> ORGANISM: Artificial sequence
<220> FEATURE:

<223> OTHER INFORMATION: Primer

<400> SEQUENCE: 25
cgcaccacct tcaaaatgtc accgttggct ctttctcc                                38

<210> SEQ ID NO 26
<211> LENGTH: 38
<212> TYPE: DNA
<213> ORGANISM: Artificial sequence
<220> FEATURE:
<223> OTHER INFORMATION: Primer

<400> SEQUENCE: 26
atgtactcct ggtacctaaa gatcccgcac taggcgtg                                 38

<210> SEQ ID NO 27
<211> LENGTH: 2550
<212> TYPE: DNA
<213> ORGANISM: Artificial sequence
<220> FEATURE:
<223> OTHER INFORMATION: Synthesized gene

<400> SEQUENCE: 27

| | |
|---|---|
| gatatcatga gcccgctggc gctgagcccg aagaccgtgg acattgtgaa catttttcag | 60 |
| aacgacgtgg agtttagcct ggtgaacgag attcataaag gcatcagccc gccggcgggt | 120 |
| gttcgtaaaa gcatgccgac catgctgctg tacgatgcga acggtctgaa gctgttcgaa | 180 |
| aacattacct atgtgaaaga gtactatctg accaacgcgg agatcgaagt gctggaaacc | 240 |
| aacagccgtc gtatcgttga gcgtattccg gacaacgcgc agctgctgga actgggtagc | 300 |
| ggcaacctgc gtaagatcga gattctgctg cgtgagttcg aacgtgtggg caaacgtgtt | 360 |
| gattactatg cgctggacct gagcctgagc gaactgcaac gtacctttgc ggaagtgagc | 420 |
| attgacgatt acacccacgt tggtctgcac ggcctgcacg gtacctatga cgatgcggtt | 480 |
| acctggctga acagcccgga aaaccgtaag cgtccgaccg tgatcatgag catgggcagc | 540 |
| agcctgggta acttcgatcg tccgggtgcg gcgaaatttc tgagccaata tgcgagcctg | 600 |
| ctgggtccga gcgacatgat gatcattggc ctggatggtt gcaaggaccc gggtaaagtg | 660 |
| taccgtgcgt ataacgacag cgaaggcgtt acccgtcaat tctacgagaa cggtctggtg | 720 |
| cacgcgaacg tggttctggg ctatgaagcg tttaagagcg atgagtggga agtggttacc | 780 |
| gactacgata ccgttgaggg tcgtcactgg gcggcgtata gcccgaagaa agacgtgacc | 840 |
| attaacggcg ttctgctgaa gaaaggtgaa aagctgttct ttgaggaagc gtacaaatat | 900 |
| ggcccggagg aacgtgatca gctgtggcgt gacgcgaagc tgatccaaag caccgagatg | 960 |
| ggtaacggca cgacgatta ccacctgcac ctgctgacca cgcgaccct gaacctgccg | 1020 |
| accagcccga gccagtatgc ggcgcacccg attccgagct cgaggaatg gcaaagcctg | 1080 |
| tggaccgcgt gggataacgc gaccaaagcg atggttccgc gtgaggaact gctgagcaag | 1140 |
| ccgatcaaac tgcgtaacag cctgatcttc tacctgggtc acattccgac ctttctggac | 1200 |
| atccacctga cccgtgcgct gcgtggcaag ctgaccgaac cgaagagcta taactgatc | 1260 |
| tttgagcgtg gcattgaccc ggatgtggac gatccggaaa atgccacag ccacagcgaa | 1320 |
| attccggatg agtggccggc gctggacgac atcctggact accaggagcg tgtgcgtagc | 1380 |
| cgtgttcgta gcatctatca aattgaaggt ctggcggaga accgtattct gggcgaagcg | 1440 |
| ctgtggatcg gtttcgagca cgaagtgatg cacctggaga cctttctgta catgctgatt | 1500 |
| caaagcgaac gtatcctgcc gccgccggcg accgagcgtc cggatttcaa gaaactgtat | 1560 |

| | |
|---|---|
| caggaagcgc gtcgtagcat gaaggcgaac gaatggttta gcgttccgga gcaaaccctg | 1620 |
| accatcggcc tggacggtgc ggataccaac gacgtgccgc cgaccaccta cggttgggac | 1680 |
| aacgaaaaac cggcgcgtac cgttaccgtt ccggcgtttg aagcgcaggg tcgtccgatt | 1740 |
| accaacggcg agtacgcgaa atatctgcag gcgaaccaaa gccgtcgtcg tccggcgagc | 1800 |
| tgggttctga cccacagcga cgaagattac gcgatcccga tggcggtgaa cggcagcagc | 1860 |
| gttggtgcga cccaggactt catgagcaac tttgcggtgc gtaccgtttt cggtccggtt | 1920 |
| ccgctggagt ttgcgcaaga ttggccggtg atggcgagct acgacgagct ggcggaatat | 1980 |
| gcggagtggg tgggctgccg tattccgacc ttcgaggaaa cccgtagcat ctacctgcac | 2040 |
| agcgcgctgc tgaaggaacg tggtggcgtt aaccacaacg gcgagccgaa cggtcacagc | 2100 |
| ctgaacggcg atctgaacgg tgtgaacggt aacggctaca gcaaaatcaa cccgggcaag | 2160 |
| ccgcgtaaac cggaccacca gccggttcaa tatccgagcc gtgatgcgct gccggtgttc | 2220 |
| ctggacctgc acggtctgaa cgttggtttt aaacactggc acccgacccc ggtgattcag | 2280 |
| aacggtgatc gtctggcggg tcaaggtgaa ctgggtggcg cgtgggagtg gaccagcacc | 2340 |
| ccgctggcgc cgcacgacgg cttcaaggcg atggagatct acccgggcta taccagcgat | 2400 |
| ttctttgacg gtaaacacaa catcattctg ggtggcagct gggcgaccca cccgcgtgtg | 2460 |
| gcgggtcgta ccacctttgt taactggtat caacacaatt atccgtacac ctgggcgggt | 2520 |
| gcgcgtctgg ttcgtgacct gtaaactagt | 2550 |

<210> SEQ ID NO 28
<211> LENGTH: 1404
<212> TYPE: DNA
<213> ORGANISM: Artificial sequence
<220> FEATURE:
<223> OTHER INFORMATION: Synthesized gene

<400> SEQUENCE: 28

| | |
|---|---|
| gatatcatga ccacgccgtt tggtgcgccg atgcgtgaac attttctgtt cgataccaac | 60 |
| ttcaaaaacc tgaatcacgg ttccttcggc acgtatccgc gtgcggtcca gaccgtgctg | 120 |
| cgtcagcatc aacactcagc agaagctcgc ccggacctgt tttatcgtat tacccgcggt | 180 |
| caaggcatcg acggttctcg tcgcattgtc gcgaacctgc tgaatatccc ggtgaacgaa | 240 |
| tgcgttttcg tcaaaaatgc caccacgggc gttgcaaccg tcctgcgtaa cctggtgttt | 300 |
| cagaaaggtg atgcagtggt ttatttcgac accatctacg gcgctgtgga gaaaaacgtt | 360 |
| cattctatta tggaagcaag tccggtcacc acgcgcaaag tggaatgtgc tctgccggtt | 420 |
| tctcatgaag atctggtcaa acgttttcgc gacgtcgtga gtcgtgcgcg cggtgaaggc | 480 |
| ctgcacgtga aagttgccgt cttcgatacg attgtgtcgg ttccgggcgt tcgtttttccg | 540 |
| ttcgaaaccc tggtcggtgt gtgccgcgaa gaaggcattc tgagcctgat cgatggtgcg | 600 |
| catggtattg ccacattcc gctggatctg ggtaccctgc gtccggactt tttcacctct | 660 |
| aacctgcata atggctgtt tgtgccgcgc ggttgtgccg tgctgcatgt tccgctgcgt | 720 |
| aatcagcacc tgatccgcac cacgttcccg accagttggg gttatattcc gccgccgagc | 780 |
| tctggcgaaa ttaccccgac ggcaacccag ggcaaatcgg cttttgaata cctgttcgaa | 840 |
| cacattagca ccacggatga tacgccgtgg ctgtgtgttc cggccgcaat gaaatttcgt | 900 |
| accgaagtgt gtgcggtgga agatcgcatc tatgcatacc tggaaacgct ggcacgtgaa | 960 |
| gctggtgaca ttgttgcccg tgcactgggt accgaagtga tgcaggaacc gggtctgaaa | 1020 |

| | |
|---|---|
| gaaggcgaag ttagccaact gcgtcgctgc ggtatggcca ccgtgcgtct gccgatcgcc | 1080 |
| gttaccagtt cctcatcgag cgatagcggt agcggtaatg gcggtggcgc cgtcatgcgt | 1140 |
| gtgcagggtg aagacggctc tagttatctg cgcattcaaa cgtccctggt tggcaccgtc | 1200 |
| tcaaattggt ttcgcgatac gctgttcgac aaatatgaaa cctttgttcc ggtcttccag | 1260 |
| catggtggct ggctgtggac ccgtctgtcc gcacaagtgt acctggaaaa gggtgatttt | 1320 |
| gaatggctgg gtggcgttct gcgcgaatgc tgtgaacgtg tggaacgcga agtgggcgtt | 1380 |
| tcctcagcta aactgtaaac tagt | 1404 |

<210> SEQ ID NO 29
<211> LENGTH: 2890
<212> TYPE: DNA
<213> ORGANISM: Aspergillus niger

<400> SEQUENCE: 29

| | |
|---|---|
| atgtcaccct tatgtccggt cgtcaagggc gttgacatcg tcgatatccg tcaaaatgac | 60 |
| gtggagtttt ccctggtaaa tgatatccag cgaggtatag atcctccggc aggaacttgc | 120 |
| cgatccatgc ccacaatgct tctttacgat gctcaggggc tcaagctgtt cgaggacatt | 180 |
| acgtacctgg aggaatacta tctcacaaat gcggagatta cgttctacg acacatgcg | 240 |
| aagaggattg ttgaacgcat cccggacaat gcgcaattac tggaactagg cagtgggtgc | 300 |
| gtcttccttc cgcttggagc atgtatagag tatagggtac agacacggga ttctaacata | 360 |
| cggtagcaat ctgcgcaaga ttgagatcct tctccaggaa ttcgaagcag cgagcaaaaa | 420 |
| agtggactac tatgccttgg atctgtcgct ctcagagttg gagcgcacat tctcggaagt | 480 |
| gtccctcgat caatatcaat atgtcaagct ccacggcctg catggcacgt acgacgacgc | 540 |
| cctcacctgg ctagaaaacc ccgcgaatcg aaaggtccca acggtgatca tgtcaatggg | 600 |
| ctcgtcgata ggaaattttg atcgtcctgc agcggcaaaa ttcttgtcgc aatttgccag | 660 |
| gctcttaggg ccgtcggatt tgatggtgct cggtttggat agttgcacgg actcggataa | 720 |
| agtgtacaag gcatacaatg attccaaggg tatcacacgg cagttctacg agaacgggtt | 780 |
| gttgcatgcg aacgctgtgc ttggatacga agcattcaaa ctcgatgaat gggatatcgt | 840 |
| gacggagtac gataacgtcg aagggcggca ccaggcgttc tacgcgccaa accgggacgt | 900 |
| gactataaac ggggtactac ttcagaaagg cgagaagcta ttttttgagg aggcattcaa | 960 |
| atatgatccc gagcagtgcg atcagctctg gcatgatgcg ggtttaattg aggacgctga | 1020 |
| gtttggcaat gagtctgggg attaccgtat gtcatccttt ggcaatgtgc tactctgcat | 1080 |
| gtcatgttgc actgcattgt gtaaaaacat gttacaccag ttgagaccat catactaaca | 1140 |
| taatctgtcg agcagttatc cacgtgctct cttcggcttc tctcaacttt tcaacgagac | 1200 |
| catcacagta tgcggctcaa tctattccga gctttgagga attccagtca ctgtggacag | 1260 |
| catgggacat tgtcaccaag gccatggttc ctagagagga acttctttcg aagccaatca | 1320 |
| aattgcgcaa tgcattaatc ttctacctcg gtcacatacc tacgtttctc ggtcagtgtt | 1380 |
| ctgcttggct atttgtggag tgcaagtata ggggtcagca tattgacaag cgcagatgtt | 1440 |
| catttgaccc gagcattggg cgaaaagcca acgcacccca gtcatatcg actcattttc | 1500 |
| gaacgcggaa tcgaccccga tgtggatgac cccgaaaagt gccattctca cagcgagatt | 1560 |
| ccagacgaat ggcctgccct tggagacatc ttggactacc aagtgcgggt tcgaagtagg | 1620 |
| gtgaggtcca ttttcagaa gcataatgtg gctgagaata gggtgcttgg tgaagcactc | 1680 |
| tggatcgggt ttgagcatga agccatgcat ctggaaacgt tcctttacat gcttatccag | 1740 |

-continued

```
agtgaaagaa cacttccgcc ccccgccgtt ccgcgccccg attttaggaa gttttttccac   1800
gatgcccggc aagagtcaag accaaacgag tggttttcga ttcccgagaa gacgctttcg   1860
gttggattac atgatgatgg acattcagtt cctcgtgact cttttggctg ggacaacgaa   1920
aagccccaga gaaagataac cgttaaagca ttcgaagctc aagcgcgacc aataacaaat   1980
ggagagtacg cgaagtatct acaggcgaat cagctgcccc agaagccaga gtcctgggtc   2040
ttgatcaagc ccgagacgta cccgacttgc aatggtgtca gtcaagacgg tagctacgct   2100
acgaatgaat tcatggcaca ctttgccgtt cgcactgtgt ttggctccgt cccgctcgag   2160
ctagcccagg actggccggt tatcgcgtcg tacgatgaat tggccaagta tgccaagtgg   2220
gtggactgca ggataccaac cttcgaagag gcaaagagta tctacgcgca tgcagctcgg   2280
ctgaaggaaa ctagccacgg cctgaacggt cacaggtaag cataccgctt ccactagatg   2340
cacaggactt actgtcatag tgaaacgaac ggagtcaacg ggcacgaaca tagcgagacc   2400
aaccccctac ggcctcgcac cccggaccac caaccggtac agcacccttc gcaagaatct   2460
ctgccggtgt ttgttgagct cgacaattgc aacgtcggct tcaaacactg gcaccctacc   2520
ccggtcatcc agaacggcga ccgactcgcc ggtcatggag agctgggagg cgtctgggag   2580
tggacgagca cggaacttgc accccacgaa gggttcgagg ccatgcaaat ctaccccgga   2640
tatacatgta agcttgctgt gtgagatata tgaacacaag ctaactgaga acagccgact   2700
tcttcgacgg aaaacacaat atcatcctcg gagggtcatg ggcgacgcat ccacggatcg   2760
ccggccgcac taccttgtaa gtccgtatgc aagactagcg ggttcatgag ctaatctgtt   2820
cagtgtcaat tggtaccagc ggaactaccc ataccctgg gctggtgccc ggctggtgcg   2880
ggatgtctga                                                          2890
```

<210> SEQ ID NO 30
<211> LENGTH: 835
<212> TYPE: PRT
<213> ORGANISM: Aspergillus niger

<400> SEQUENCE: 30

```
Met Ser Pro Leu Cys Pro Val Val Lys Gly Val Asp Ile Val Asp Ile
1               5                   10                  15

Arg Gln Asn Asp Val Glu Phe Ser Leu Val Asn Asp Ile Gln Arg Gly
            20                  25                  30

Ile Asp Pro Pro Ala Gly Thr Cys Arg Ser Met Pro Thr Met Leu Leu
        35                  40                  45

Tyr Asp Ala Gln Gly Leu Lys Leu Phe Glu Asp Ile Thr Tyr Leu Glu
    50                  55                  60

Glu Tyr Tyr Leu Thr Asn Ala Glu Ile Asp Val Leu Arg Thr His Ala
65                  70                  75                  80

Lys Arg Ile Val Glu Arg Ile Pro Asp Asn Ala Gln Leu Leu Glu Leu
                85                  90                  95

Gly Ser Gly Asn Leu Arg Lys Ile Glu Ile Leu Leu Gln Glu Phe Glu
            100                 105                 110

Ala Ala Ser Lys Lys Val Asp Tyr Tyr Ala Leu Asp Leu Ser Leu Ser
        115                 120                 125

Glu Leu Glu Arg Thr Phe Ser Glu Val Ser Leu Asp Gln Tyr Gln Tyr
    130                 135                 140

Val Lys Leu His Gly Leu His Gly Thr Tyr Asp Asp Ala Leu Thr Trp
145                 150                 155                 160
```

```
Leu Glu Asn Pro Ala Asn Arg Lys Val Pro Thr Val Ile Met Ser Met
                165                 170                 175
Gly Ser Ser Ile Gly Asn Phe Asp Arg Pro Ala Ala Lys Phe Leu
            180                 185                 190
Ser Gln Phe Ala Arg Leu Leu Gly Pro Ser Asp Leu Met Val Leu Gly
        195                 200                 205
Leu Asp Ser Cys Thr Asp Ser Asp Lys Val Tyr Lys Ala Tyr Asn Asp
210                 215                 220
Ser Lys Gly Ile Thr Arg Gln Phe Tyr Glu Asn Gly Leu Leu His Ala
225                 230                 235                 240
Asn Ala Val Leu Gly Tyr Glu Ala Phe Lys Leu Asp Glu Trp Asp Ile
                245                 250                 255
Val Thr Glu Tyr Asp Asn Val Glu Gly Arg His Gln Ala Phe Tyr Ala
            260                 265                 270
Pro Asn Arg Asp Val Thr Ile Asn Gly Val Leu Leu Gln Lys Gly Glu
        275                 280                 285
Lys Leu Ile Phe Glu Glu Ala Phe Lys Tyr Asp Pro Glu Gln Cys Asp
        290                 295                 300
Gln Leu Trp His Asp Ala Gly Leu Ile Glu Asp Ala Glu Phe Gly Asn
305                 310                 315                 320
Glu Ser Gly Asp Tyr Leu Ile His Val Leu Ser Ala Ser Leu Asn
                325                 330                 335
Phe Ser Thr Arg Pro Ser Gln Tyr Ala Ala Gln Ser Ile Pro Ser Phe
            340                 345                 350
Glu Glu Phe Gln Ser Leu Trp Thr Ala Trp Asp Ile Val Thr Lys Ala
        355                 360                 365
Met Val Pro Arg Glu Glu Leu Leu Ser Lys Pro Ile Lys Leu Arg Asn
        370                 375                 380
Ala Leu Ile Phe Tyr Leu Gly His Ile Pro Thr Phe Leu Asp Val His
385                 390                 395                 400
Leu Thr Arg Ala Leu Gly Glu Lys Pro Thr His Pro Lys Ser Tyr Arg
                405                 410                 415
Leu Ile Phe Glu Arg Gly Ile Asp Pro Asp Val Asp Asp Pro Glu Lys
            420                 425                 430
Cys His Ser His Ser Glu Ile Pro Asp Glu Trp Pro Ala Leu Gly Asp
        435                 440                 445
Ile Leu Asp Tyr Gln Val Arg Val Arg Ser Arg Val Arg Ser Ile Phe
        450                 455                 460
Gln Lys His Asn Val Ala Glu Asn Arg Val Leu Gly Glu Ala Leu Trp
465                 470                 475                 480
Ile Gly Phe Glu His Glu Ala Met His Leu Glu Thr Phe Leu Tyr Met
                485                 490                 495
Leu Ile Gln Ser Glu Arg Thr Leu Pro Pro Ala Val Pro Arg Pro
            500                 505                 510
Asp Phe Arg Lys Phe Phe His Asp Ala Arg Gln Glu Ser Arg Pro Asn
        515                 520                 525
Glu Trp Phe Ser Ile Pro Glu Lys Thr Leu Ser Val Gly Leu His Asp
        530                 535                 540
Asp Gly His Ser Val Pro Arg Asp Ser Phe Gly Trp Asp Asn Glu Lys
545                 550                 555                 560
Pro Gln Arg Lys Ile Thr Val Lys Ala Phe Glu Ala Gln Ala Arg Pro
                565                 570                 575
```

```
Ile Thr Asn Gly Glu Tyr Ala Lys Tyr Leu Gln Ala Asn Gln Leu Pro
            580                 585                 590

Gln Lys Pro Glu Ser Trp Val Leu Ile Lys Pro Glu Thr Tyr Pro Thr
        595                 600                 605

Cys Asn Gly Val Ser Gln Asp Gly Ser Tyr Ala Thr Asn Glu Phe Met
610                 615                 620

Ala His Phe Ala Val Arg Thr Val Phe Gly Ser Val Pro Leu Glu Leu
625                 630                 635                 640

Ala Gln Asp Trp Pro Val Ile Ala Ser Tyr Asp Glu Leu Ala Lys Tyr
            645                 650                 655

Ala Lys Trp Val Asp Cys Arg Ile Pro Thr Phe Glu Glu Ala Lys Ser
            660                 665                 670

Ile Tyr Ala His Ala Ala Arg Leu Lys Glu Thr Ser His Gly Leu Asn
            675                 680                 685

Gly His Ser Glu Thr Asn Gly Val Asn Gly His Glu His Ser Glu Thr
        690                 695                 700

Asn Pro Leu Arg Pro Arg Thr Pro Asp His Gln Pro Val Gln His Pro
705                 710                 715                 720

Ser Gln Glu Ser Leu Pro Val Phe Val Glu Leu Asp Asn Cys Asn Val
                725                 730                 735

Gly Phe Lys His Trp His Pro Thr Pro Val Ile Gln Asn Gly Asp Arg
            740                 745                 750

Leu Ala Gly His Gly Glu Leu Gly Gly Val Trp Glu Trp Thr Ser Thr
            755                 760                 765

Glu Leu Ala Pro His Glu Gly Phe Glu Ala Met Gln Ile Tyr Pro Gly
770                 775                 780

Tyr Thr Ser Asp Phe Phe Asp Gly Lys His Asn Ile Ile Leu Gly Gly
785                 790                 795                 800

Ser Trp Ala Thr His Pro Arg Ile Ala Gly Arg Thr Thr Phe Val Asn
                805                 810                 815

Trp Tyr Gln Arg Asn Tyr Pro Tyr Pro Trp Ala Gly Ala Arg Leu Val
            820                 825                 830

Arg Asp Val
        835

<210> SEQ ID NO 31
<211> LENGTH: 42
<212> TYPE: DNA
<213> ORGANISM: Artificial sequence
<220> FEATURE:
<223> OTHER INFORMATION: Primer

<400> SEQUENCE: 31
cgcaccacct tcaaaatgtc acccttatgt ccggtcgtca ag                42

<210> SEQ ID NO 32
<211> LENGTH: 35
<212> TYPE: DNA
<213> ORGANISM: Artificial sequence
<220> FEATURE:
<223> OTHER INFORMATION: Primer

<400> SEQUENCE: 32
atgtactcct ggtactcaga catcccgcac cagcc                       35
```

METHOD FOR PRODUCING SELENONEINE

CROSS REFERENCE TO RELATED APPLICATIONS

The present application is a divisional of U.S. application Ser. No. 15/750,792 filed Feb. 6, 2018, which is the national phase of PCT International Application PCT/JP2016/068128 filed on Jun. 17, 2016, which claims the benefit of priority to Japanese Patent Application No. 2015-157443 filed on Aug. 7, 2015, the disclosure of each of which (including Sequence Listings) is incorporated herein by reference in its entirety.

SEQUENCE LISTING

The instant application contains a Sequence Listing submitted in ASCII format via EFS-Web on May 13, 2021, and is hereby incorporated by reference in its entirety. Said ASCII copy is named 2018-02-06_SequenceListing_6134-0124PUS1.txt, and is 59,784 bytes in size.

TECHNICAL FIELD

The present invention relates to a method for producing selenoneine. In particular, the present invention relates to a method for producing selenoneine using a microorganism having the ability to produce selenoneine.

BACKGROUND ART

Selenium (Se) is an element belonging to the group 16 of the periodic table. In other words, it is one of the elements of the oxygen family (chalcogen elements). Selenium is a trace element essential to humans. Selenium forms part of enzymes and proteins in living bodies and plays an important role in antioxidant responses. Since selenium is abundant in algae, fish and shellfish, meat, egg yolk and the like, it can be ingested through food products containing these selenium sources.

In animal species, for example, glutathione peroxidase and other selenium-containing enzymes that contain selenocysteine and selenomethionine as constituent amino acids are known. The presence of selenoproteins is also reported in many algae and plant species.

Selenium deficiency can cause cell damage due to peroxides that can result in the onset of various diseases, including cardiomyopathy (Keshan disease), Kashin-Beck disease (osteochondroarthrosis deformans), coronary artery diseases such as angina pectoris and myocardial infarction, and cardiovascular diseases. In addition, selenium deficiency has been reported to induce muscle pain, dry skin, hepatic necrosis, as well as increased risk of cancers, including lung cancer, bowel cancer, prosthetic cancer, rectal cancer, breast cancer and leukemia.

On the other hand, selenium has toxicity and is harmful. For example, selenium exhibits increased toxicity in the form of selenium oxyanion. When ingested in excessive amounts, selenium is known to induce deformed nails and alopecia, gastrointestinal injury, neurological disorders, myocardial infarction, acute dyspnea, renal failure and other disorders. Ministry of Health, Labour and Welfare of Japan provides the standard for ingestion of selenium in meals, which defines, for example, the estimated average required amount of 25 (20) µg/day, the recommended amount of 30 (25) µg/day, and the maximum amount of 460 (350) µg/day for males (females) aged 30 to 49 (See, Non-Patent Document 1, which is incorporated herein by reference in its entirety).

Currently, supplements containing an inorganic selenium such as selenous acid (inorganic selenium compound) or an organic selenium such as selenomethionine (organic selenium compound) are used in the prevention or treatment of diseases associated with selenium deficiency. Selenium-rich yeast obtained by culturing yeast in a medium containing an inorganic selenium compound is also used as a type of organic selenium compounds.

Another type of organic selenium compounds is selenoneine, a compound known to have antioxidant activity in living bodies and the ability to promote cell growth (See, Patent Document 1, which is incorporated herein by reference in its entirety). Selenoneine is a selenium analog obtained by replacing the SH group of ergothioneine with SeH group and has an antioxidant activity 1,000 times higher than ergothioneine (See, Non-Patent Document 3, which is incorporated herein by reference in its entirety).

Known methods for producing selenoneine include extraction of selenoneine from organs or blood of animals (See, Patent Document 1 below, which is incorporated herein by reference in its entirety), and use of fission yeast *Schizosaccharomyces pombe* transfected with genes involved in ergothioneine biosynthesis (See, Non-Patent Document 2, which is incorporated herein by reference in its entirety).

CITATION LIST

Patent Document

Patent Document 1: JP5669056

Non-Patent Document

Non-Patent Document 1: 2015 edition of Report of Committee for Determining Standard for Ingestion in Meals for Japanese; Ministry of Health, Labour and Welfare of Japan; Mar. 28, 2014 (mhlw.go.jp/file/05-Shingikai-10901000-Kenkoukyoku-Soumuka/0000042638.pdf).

Non-Patent Document 2: PLoS One 2014 May 14; 9(5): e97774

Non-Patent Document 3: J. Biol. Chem.; 2010 18134-8

SUMMARY OF INVENTION

Technical Problem

According to the method described in Patent Document 1, selenoneine is extracted from the guts or blood of fish. However, since selenoneine is scarce in fish guts or blood, large amounts of fish are required to obtain large amounts of selenoneine.

On the other hand, Non-Patent Document 2 describes in vivo synthesis of selenoneine using *Schizosaccharomyces pombe* transformant transformed to overexpress gene SPBC1604.01 encoding an enzyme known as Egt1 that catalyzes a reaction in which hercynyl-selenocysteine is produced from histidine and selenocysteine. However, only very small amounts of selenoneine can be obtained using the *Schizosaccharomyces pombe* transformant as described in Non-Patent Document 2.

Accordingly, it is an objective of the present invention to provide a method for producing selenoneine that allows production of selenoneine at higher yields as compared to the method using the *Schizosaccharomyces pombe* transformant as described in Non-Patent Document 2 in order to enable industrial-scale production of selenoneine.

Solution to Problem

In the course of extensive studies to find solutions to the above-described problems, the present inventors have succeeded in identifying, from the fungus *Aspergillus sojae*, a gene AsEgtA encoding an enzyme that catalyzes a reaction in which selenoneine is produced from histidine and a selenium compound.

The present inventors have also constructed a DNA construct for overexpressing AsEgtA protein and used it to transform *Aspergillus sojae* to successfully produce *Aspergillus sojae* transformant that can overexpress the AsEgtA protein. Similarly, the present inventors have identified the gene AoEgtA from *Aspergillus oryzae* that has a high homology with the gene AsEgtA and used it to successfully produce *Aspergillus oryzae* transformant capable of overexpressing the AoEgtA protein.

Surprisingly, the resulting transformant was capable of producing selenoneine not only from organic selenium compounds such as selenocystine, but also from inorganic selenium compounds such as selenous acid. Moreover, the amount of selenoneine produced by the *Aspergillus oryzae* transformant was significantly greater than the amount produced by *Schizosaccharomyces pombe* transformant as described in Non-Patent Document 2.

More surprisingly, the present inventors have found out that the above-described transformant explicitly exhibits higher resistance to selenium compounds as compared to the wild-type strain even in the presence of a toxic concentration of selenium compound. Also, the above-described transformant can be cultured using the standard technique and their growth rate is comparable to that of the wild-type strain. These observations suggest that the above-described transformant may be used to produce selenoneine at large scale. It is these successful examples and findings that ultimately led to the completion of the present invention.

According to one embodiment of the present invention, there is provided a method for producing selenoneine, the method comprising the step of applying histidine and a selenium compound to a transformant that has a gene encoding an enzyme of (1) below introduced therein and that can overexpress the introduced gene, to obtain selenoneine.
(1) An enzyme that catalyzes a reaction in which hercynylselenocysteine shown in the formula [I] below is produced from histidine and selenocysteine in the presence of S-adenosylmethionine and iron (II):

(Chemical formula 1)

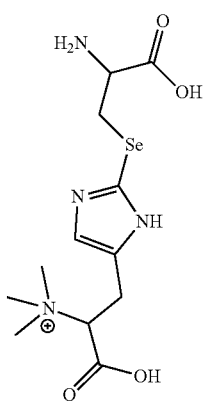

Preferably, the selenium compound is at least one selenium compound selected from the group consisting of organic selenium compounds and inorganic selenium compounds, and salts thereof.

Preferably, the organic selenium compounds and salts thereof comprise at least one selenium compound selected from the group consisting of selenocysteine, selenocystine, selenomethionine, Se-(methyl)seleno-L-cysteine, selenopeptides, selenoproteins and salts thereof and selenium yeast, and the inorganic selenium compound and salts thereof comprise at least one selenium compound selected from the group consisting of selenic acid, selenous acid, selenium chloride, selenium, selenium sulfide, dimethylselenium, selenophosphate, selenium dioxide and salts thereof.

Preferably, the transformant is a transformant that further has a gene encoding an enzyme of (2) below introduced therein and that can overexpress the introduced gene.
(2) An enzyme that catalyzes a reaction in which selenoneine is produced from hercynylselenocysteine shown in the formula [I] below using pyridoxal 5'-phosphate as a coenzyme:

(Chemical formula 2)

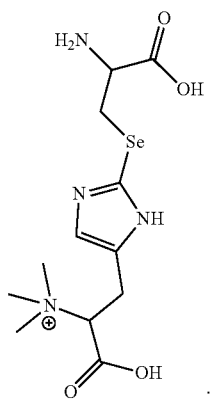

Preferably, the transformant is produced by using as a host organism a microorganism that expresses at least one enzyme selected from the group consisting of selenic acid reductase, selenocysteine lyase, and serine dehydratase.

Preferably, the transformant is produced by using as a host organism at least one microorganism selected from the group consisting of microorganisms of genus *Aspergillus*, genus *Escherichia*, genus *Trichoderma*, genus *Fusarium*, genus *Penicillium*, genus *Rhizopus*, and genus *Neurospora*.

Preferably, the microorganism of the genus *Aspergillus* is a microorganism selected from the group consisting of *Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi*.

Preferably, the transformant is produced by using *E. coli* as a host organism.

Preferably, the transformant is a transformant in which the expression of the gene encoding the enzyme of (1) is enhanced to increase the amount of selenoneine as compared to the host organism.

Preferably, the transformant is a transformant in which the expression of the gene encoding the enzyme of (1) is enhanced so that the amount of selenoneine produced when the transformant is cultured in a selenocystine-containing medium suitable for the growth of the host organism at 30° C. for 5 days is preferably not less than 10 μg per gram of wet cell mass, more preferably not less than 20 μg per gram of wet cell mass, even more preferably not less than 40 μg per gram of wet cell mass, and still more preferably not less than 100 μg per gram of wet cell mass.

Preferably, the gene encoding the enzyme of (1) is a gene selected from the group consisting of a gene having a base sequence of SEQ ID NO: 1, and a gene having a base sequence of SEQ ID NO: 23 in the sequence listing, or the enzyme (1) is an enzyme selected from the group consisting of an enzyme having an amino acid sequence of SEQ ID NO: 4, and an enzyme having an amino acid sequence of SEQ ID NO: 24 in the sequence listing.

Preferably, the gene encoding the enzyme of (2) is a gene selected from the group consisting of a gene having a base sequence of SEQ ID NO: 2, and a gene having a base sequence of SEQ ID NO: 3 in the sequence listing, or the enzyme (2) is an enzyme selected from the group consisting of an enzyme having an amino acid sequence of SEQ ID NO: 5, and an enzyme having an amino acid sequence of SEQ ID NO: 6 in the sequence listing.

As a further embodiment of the present invention, it has been found that certain fungi, including those of genus Aspergillus, such as Aspergillus sojae, can be used to produce selenoneine from organic selenium compounds such as selenocystine and inorganic selenium compounds such as selenous acid while the amount of selenoneine produced is less than the amount produced by the production method using the above-described transformant. Specifically, according to another embodiment of the present invention, there is provided a method for producing selenoneine, the method comprising the step of applying histidine and a selenium compound to a fungus, including those of genus Aspergillus, such as Aspergillus sojae, having a gene encoding the enzyme of (1) on its genome DNA in order to obtain selenoneine.

Advantageous Effects of Invention

According to the production method or the transformant, which serves as one embodiment of the present invention, selenoneine can be produced at high yields under conditions for culturing standard host organisms. As a consequence, the production method or the transformant serving as one embodiment of the present invention allows industrial-scale production of selenoneine.

BRIEF DESCRIPTION OF DRAWINGS

FIG. 1 shows the results of LC-MS analysis showing the peaks corresponding to selenoneine for selenium extracts prepared from cultures obtained by culturing a control strain and a transformed Aspergillus sojae ("(AsEgtA+AsEgtC) transformant") in a selenocystine-supplemented DPY liquid medium as described in Examples.

FIG. 2 shows the results of LC-MS analysis showing the peaks corresponding to ergothioneine for selenium extracts prepared from cultures obtained by culturing a control strain and a transformed Aspergillus sojae ("(AsEgtA+AsEgtC) transformant") in a selenocystine-supplemented DPY liquid medium as described in Examples.

FIG. 3 is an enlarged MS spectrum showing the peaks of the results of LC-MS analysis in FIG. 1 near 31-min retention time.

FIG. 4 shows calculated values for the ion distribution of selenoneine estimated from the relative isotopic abundance.

FIG. 5 shows the results of LC-MS analysis showing the peaks corresponding to selenoneine for selenium extracts prepared from cultures obtained by culturing a transformed Aspergillus sojae in a DPY liquid medium ("DPY"), a selenocystine-supplemented DPY liquid medium ("DPY+ selenocystine"), or a selenous acid-supplemented DPY liquid medium ("DPY+selenous acid"), as described in Examples.

FIG. 6 shows the results of LC-MS analysis showing the peaks corresponding to selenoneine for selenium extracts prepared from cultures obtained by culturing a control strain and a transformed Aspergillus oryzae ("AoEgtA transformant") in a selenocystine-supplemented DPY liquid medium as described in Examples.

FIG. 7 shows the results of evaluation of toxicity of selenocystine against a control strain ("NBRC4239 strain") and a transformed Aspergillus sojae ("(AsEgtA+AsEgtC) transformant") as described in Examples.

FIG. 8 shows the results of evaluation of toxicity of selenous acid against a control strain ("NBRC4239 strain") and a transformed Aspergillus sojae ("(AsEgtA+AsEgtC) transformant") as described in Examples.

FIG. 9 is a photographic representation of SDS-PAGE performed with the total protein extracted from transformants and control strain as described in Examples. Lane 1 corresponds to the total protein derived from the control strain, Lane 2 corresponds to the total protein derived from the AsEgtA transformant, Lane 3 corresponds to the total protein derived from the AsEgtB transformant, Lane 4 corresponds to the total protein derived from the AsEgtC transformant, Lane 5 corresponds to the total protein derived from the (AsEgtA+AsEgtB) transformant, and Lane 6 corresponds to the total protein derived from the (AsEgtA+AsEgtC) transformant.

DESCRIPTION OF EMBODIMENTS

A production method and a transformant, which provides one embodiment of the present invention, will now be described in details.

(General Description of the Production Method)

One embodiment of the production method includes the step of applying histidine and a selenium compound to a transformant that has a gene encoding an enzyme of (1) below (referred to as enzyme (1), hereinafter) introduced therein and that can overexpress the introduced gene, to obtain selenoneine. As used herein, the selenium compound includes, in addition to selenium compounds themselves, salts, complexes, crosslinked products and derivatives of selenium compounds.

(1) An enzyme that catalyzes a reaction in which hercynylselenocysteine shown in the formula [I] below is produced from histidine and selenocysteine in the presence of S-adenosylmethionine and iron (II):

(Chemical formula 3)

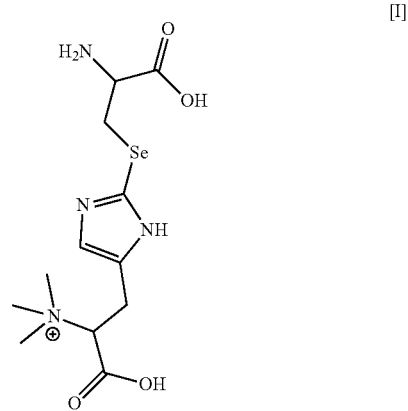

[I]

The transformant for use in one embodiment of the production method can overexpress the gene encoding the enzyme (1) introduced as a foreign gene to ultimately produce selenoneine from histidine and a selenium compound. The gene encoding the enzyme (1) to be overexpressed may be one or two or more genes.

Without wishing to be bound by any theory or presumption, the reaction in which hercynylselenocysteine is produced from histidine and selenocysteine, which is one proposed mechanism of the biosynthesis of selenoneine in fungi, can be schematically represented by the formula (II) below:

[Chemical formula 4)

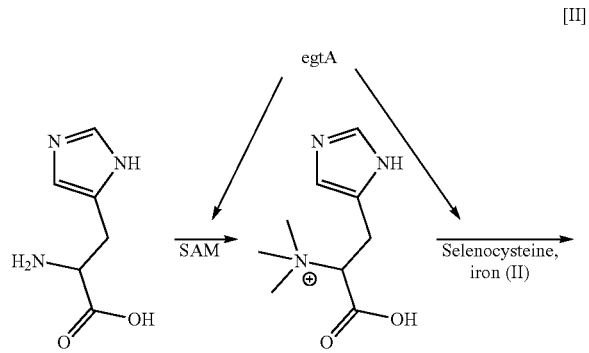

[II]

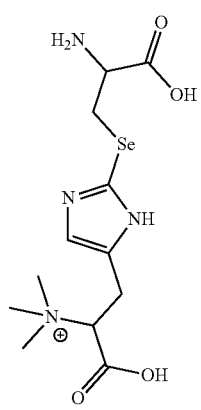

wherein SAM represents 5-adenosylmethionine.

The enzyme (1) corresponds to egtA in the formula (II).

The transformant for use in one embodiment of the production method is preferably a transformant that further has a gene encoding an enzyme of (2) below (referred to as enzyme (2), hereinafter) introduced therein and that can overexpress the introduced gene.

(2) An enzyme that catalyzes a reaction in which selenoneine is produced from hercynylselenocysteine shown in the formula [I] above using pyridoxal 5'-phosphate as a coenzyme.

It is believed that the transformant for use in one embodiment of the production method can overexpress the gene encoding the enzyme (2), which is introduced as a foreign gene, to effectively produce selenoneine from a selenoneine precursor such as hercynylselenocysteine. However, the gene encoding the enzyme (2) may not necessarily be introduced as long as the host organism expresses the enzyme (2) at sufficient levels. The gene encoding the enzyme (2) to be overexpressed may be one or two or more genes.

The transformants for use in one embodiment of the present invention are generally divided into two categories: those that overexpress the gene encoding the enzyme (1) but not the gene encoding the enzyme (2), and those that overexpress both the gene encoding the enzyme (1) and the gene encoding the enzyme (2).

(Enzymological Properties of Enzymes (1) and (2))

As shown in the formula [II] above, the enzyme (1) has an activity to catalyze the reaction in which histidine is converted to hercynine with a trimethylated $NH_2$ group in an S-adenosylmethionine (SAM)-dependent manner (which is referred to as "first activity," hereinafter). The enzyme (1) also has an activity to catalyze the reaction in which hercynylselenocysteine is produced from hercynine and selenocysteine in the presence of iron (II) (which is referred to as "second activity," hereinafter). As a result of the first and the second activities, the enzyme (1) can produce selenoneine from histidine and selenocysteine in the presence of S-adenosylmethionine and iron (II).

The enzyme (2) has an activity to catalyze the reaction in which selenoneine is produced from hercynylselenocysteine using pyridoxal 5'-phosphate (PLP) as a coenzyme (which is referred to as "third activity," hereinafter).

The transformant for use in one embodiment of the production method can express a gene or genes encoding the enzyme (1) or the enzymes (1) and (2) such that it can ultimately produce selenoneine from organic selenium compounds such as histidine and selenocysteine under conditions under which the respective enzymes are activated. More surprisingly, the transformant can produce selenoneine not only from organic selenium compounds, but also from inorganic selenium compounds such as selenous acid.

It should be noted that the enzyme (1) and the enzyme (2) may be used in the biosynthesis of ergothioneine. One proposed mechanism of the proposed biosynthesis of ergothioneine in fungi is represented by the formula [III] below:

[Chemical formula 5)

[III]

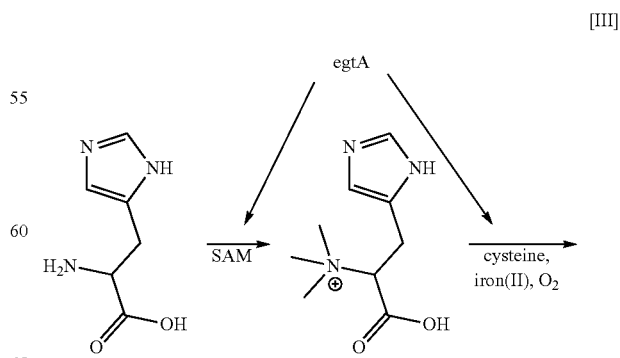

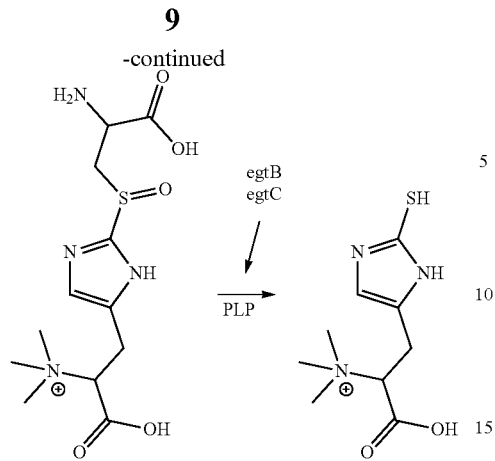

wherein SAM represents S-adenosylmethionine and PLP represents pyridoxal 5'-phosphate.

The enzyme (1) corresponds to egtA in the formula [III] while the enzyme (2) corresponds to egtB and/or egtC in the formula [III].

(The Structural Properties of Enzymes (1) and (2))

The enzyme (1) may be any enzyme that has the above-described enzymological properties; that is, any enzyme that has an activity to catalyze the reaction in which hercynylselenocysteine is produced from histidine and selenocysteine in the presence of S-adenosylmethionine and iron (II), and is not particularly limited by its structural properties, such as amino acid sequence, entire or partial conformation and molecular weight; biochemical properties, such as optimum pH, optimum temperature and deactivation conditions; the organisms from which it originates; or other conditions. However, the enzyme (1) preferably contains conserved domains well-conserved among enzymes with the first and/or second activities so that it exhibits the first and the second activities.

Examples of the conserved domain that has the first activity include conserved domains of SAM-dependent methyltransferase, specific examples of which are SAM-dependent methyltransferase domains containing the DUF2260 domain. Examples of the conserved domain that has the second activity include conserved domains of sulfatase, specific examples of which are formylglycine-generating enzyme (FGE)-sulfatase domains. In order for the enzyme to exhibit the first and the second activities, the above-described domains may not necessarily be connected in tandem; for example, nonconserved regions may be present within the domains. The enzyme (1) preferably contains a DinB_2 domain between the conserved domain of SAM-dependent methyltransferase and the conserved domain of sulfatase. If present, the DinB_2 domain preferably contains $HX_3HXE$, an iron-binding motif.

For example, one embodiment of the enzyme (I) has a structure that contains a conserved domain of SAM-dependent methyltransferase, a DinB_2 domain, and a conserved domain of sulfatase. Another embodiment of the enzyme (1) has a structure that contains a SAM-dependent methyltransferase domain containing DUF2260 domain, a DinB_2 domain containing $HX_3HXE$, and an FGE-sulfatase domain.

One preferred embodiment of the enzyme (1) is one that has 30% or higher, preferably 40% or higher, more preferably 45% or higher, further more preferably 60% or higher, in particular preferably 70% or higher sequence identity to NCU04343 described, in Non-Patent Document 2. As used herein, the term "sequence identity" refers to the identity between the two sequences aligned to each other and does not refer to the similarity between the two sequences. Specific examples of the enzyme (1) include, but are not limited to, proteins assigned the following accession numbers (the numbers in the parentheses indicate sequence identities obtained by Blastp using a AsEgtA protein of SEQ ID NO: 4 as a query sequence):

XP_00172739.1 (97%), XP_002375556.1 (97%), XP_001211614.1 (74%), GAA90479.1 (75%), XP_001261027.1 (72%), XP_001275843.1 (72%), EDP55069.1 (72%) XP_755900.1 (72%), EHA24811.1 (74%), XP_001397117.2 (73%), EYE96655.1 (72%), CAK42541.1 (71%), XP_680889.1 (69%), EPS32723.1 (66), GAD91762.1 (63%), EKV06018.1 (63%), XP_002487159.1 (61%), XP_002145387.1 (61%), CDM31097.1 (62%), XP_002623045.1 (57%), EQL36096.1 (57%), EEQ91012.1 (57%), XP_002794316.1 (57%), XP_002540839.1 (57%), XP_001246505.1 (57%), XP_003066681.1 (56%), EFW18329.1 (56%), EEH06820.1 (56%), XP_003172803.1 (55%), EGE82230.1 (56), EGD95426.1 (54%), EZF30391.1 (54%), EHY53149.1 (53%), XP_002844140.1 (54%), XP_003237555.1 (54%), EXJ78765.1 (52%), XP_001543980.1 (53%), EXJ84167.1 (53%), EXJ76804.1 (51%), ETI21425.1 (52%), EXJ55868.1 (52%), EKG13377.1 (51%), XP_003836988.1 (51%), EON60831.1 (50%), EGE08446.1 (52%), EMD86163.1 (51%), EUN21814.1 (51%) EMD69895.1 (50%), EME40669.1 (52%), EUC45427.1 (51%), EEH18365.1 (52%), XP_001939537.1 (51%), EUC28327.1 (50%), XP_003296645.1 (50%), EER38486.1 (54%), XP_007587632.1 (50%), EOA87110.1 (50%), EEH47303.1 (54%) EMC91772.1 (51%), EJT79063.1 (50%), XP_007289878.1 (51%) EMF09308.1 (50%), XP_007274188.1 (49%), XP_003849540.1 (51%), ENH83409.1 (50%), EQB47754.1 (48%), XP_006693510.1 (51%), ETN41916.1 (50%), XP_003711933.1 (49%), EWG46299.1 (50%), EGU87412.1 (49%), ESZ95365.1 (48%), EGC47631.1 (52%), EXM31381.1 (49%), eXL83373.1 (49%) XP_385823.1 (50%), EMT70054.1 (50%), EXK95313.1 (49%), CCT71860.1 (50%), EXM04867.1 (49%), EXA38531.1 (49%), EWZ34577.1 (49%), EWY87102.1 (49%), ENH70585.1 (49%), EYB29661.1 (50%), EXK37219.1 (49%), EWZ95323.1 (49%), EGY20613.1 (49%), EME78671.1 (50%), EKJ73623.1 (50%), EFQ30701.1 (48%), EPE09977.1 (48%), EXV06624.1 (49%), ERS99852.1 (49%), EGO59462.1 (49%), XP_003348780.1 (48%), EFY99927.1 (49%), XP_007594915.1 (47%), XP_003660752.1 (49%), EAA27088.3 (49%), ERF68279.1 (49%), EFX04429.1 (50%), ETR98676.1 (49%), EFY84340.1 (48%), XP_006968620.1 (48%), XP_00304884.1 (49%), EHK20832.1 (49%), EPE24413.1 (49%), EJP62962.1 (49%), ETS83740.1 (48%), EHK45989.1 (49%), ELQ64904.1 (47%), XP_006672555.1 (48%), ELQ40007.1 (46%), EXL83375.1 (50%), EXK95315.1 (50%), CCE33591.1 (48%), EXM04869.1 (51%), EXA38533.1 (50%), EWZ95325.1 (50%), EXK37221.1 (50%), EWZ34579.1 (50%), EWY87104.1 (50%), CCX31754.1 (47%), XP_956324.2 (46%), and XP_956324.2 (46%).

Of the above-listed proteins, the protein with accession number XP_001727309.1 (97%) is a protein having an amino acid sequence of SEQ ID NO: 24. Also, it is confirmed that the protein with accession number XP_001397117.2 (73%), is a protein that is expressed and that has the above-mentioned first and second activities in *Aspergillus sojae*, yet being derived from *Aspergillus niger*. These results suggest that methyltransferases (or putative methyltransferases or hypothetical proteins) having an amino acid sequence with 40% or higher, preferably 50% or higher, more preferably 70% or higher sequence identity to the amino acid sequence of the AsEgtA protein may be used as the enzyme (1).

The enzyme (2) may also be any enzyme that has the above-described enzymological properties; that is, any enzyme that has the PLP-binding cysteine desulfurase activity such that it can catalyze the reaction in which selenoneine is produced from hercynylselenocysteine, and is not particularly limited by its structural properties, biochemical properties, the organisms from which it originates, or other conditions. However, since the enzyme (2) has the third activity, it is preferred that the enzyme contains conserved domains well-conserved among enzymes with the third activity.

Examples of the conserved domain that has the third activity contain conserved domains of PLP-binding cysteine desulfurases. The enzyme (2) may include at least two types of structurally different enzymes: those containing a PLP-binding cysteine desulfurase domain with approximately 75% sequence identity to NCU04636 described in document by BELLO M H et al. (BELLO M H et al., Fungal Genet Biol. 2012 February; 49(2):160-72; the entire disclosure of which is incorporated herein by reference) and those containing a PLP-binding cysteine desulfurase domain with approximately 44% sequence identity to NCU11365 described in Non-Patent Document 2. The enzyme (2) may comprise one of the two types or both.

(Amino Acid Sequences of Enzymes (1) and (2))

The enzymes (1) and (2) may have any amino acid sequence as long as the resulting enzyme has the above-described enzymological properties, or preferably, the above-described enzymological properties and structural properties. For example, one embodiment of the enzyme (1) having the above-described enzymological and structural properties includes the amino acid sequence of SEQ ID NO: 4, and one embodiment of the enzyme (2) having the above-described enzymological and structural properties includes the amino acid sequences of SEQ ID NOs: 5 and 6. The enzymes having an amino acid sequence of SEQ ID NOs: 4 to 6 each originate from *Aspergillus sojae* and are named by the present inventors as AsEgtA, AsEgtB, and AsEgtC proteins, respectively. The base sequences of the genes encoding these enzymes are given in SEQ ID NOs: 1 to 3.

Likewise, one embodiment of the enzyme (1) having the above-described enzymological and structural properties includes the amino acid sequence of SEQ ID NO: 24, The enzyme having an amino acid sequence of SEQ ID NO: 24 originates from *Aspergillus oryzae* and is named by the present inventors as AoEgtA protein. The base sequence of the gene encoding the enzyme is given in SEQ ID NO: 23.

The AsEgtA, AsEgtB and AsEgtC proteins are encoded by genes encoding these enzymes present on the chromosomal DNA of *Aspergillus sojae*. The AoEgtA protein is encoded by gene encoding the enzyme present, on the chromosomal DNA of *Aspergillus oryzae*. The genes present on the chromosomal DNA of the organisms of origin and the proteins and the enzymes encoded by such genes may be referred to as "wild-type genes," "wild-type proteins" and "wild-type enzymes," herein.

The amino acid sequence of the enzymes (1) and (2) may be any amino acid sequence resulting from deletion, substitution, addition or other modification of one to several amino acids in the amino acid sequence of the wild type enzyme as long as the resulting enzyme, has the above-described enzymological properties. As used herein, the range specified by the phrase "one to several" as in "deletion, substitution or addition of one to several amino acids" in the amino acid sequence is not particularly limited but specifically refers to 1, 2, 3, 4, 5, 6, 7, 8, 9, 10, 11, 12, 13, 14, 15, 16, 17, 18, 19, or 20 amino acids, preferably 1, 2, 3, 4, 5, 6, 7, 8, 9, or 10 or so amino acids, more preferably 1, 2, 3, 4, or 5 or so amino acids. As used herein, the term "deletion of amino acids" means that amino acid residues are lost or eliminated from the sequence. The term "substitution of amino acids" means that amino acid residues are replaced with other amino acid residues. The term "addition of amino acids" means that new amino acid residues are added to the sequence by inserting them into the sequence.

Specific embodiments of "deletion, substitution or addition of one to several amino acids" include embodiments in which one to several amino acids are replaced with other chemically similar amino acids. For example, a hydrophobic amino acid may be substituted with another hydrophobic amino acid, or a polar amino acid may be substituted with another polar amino acid having the same charge. Such chemically similar amino acids are known in the art for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, aspargine, and cysteine. Examples of positively charged basic amino acids include arginine, histidine, and lysine. Examples of negatively charged acidic amino acids include asparatic acid, and glutamic acid.

Examples of the amino acid sequences resulting from deletion, substitution, addition or other modification of one to several amino acids in the amino acid sequence of the wild-type enzyme include amino acid sequences having a particular percentage or higher sequence identity to the amino acid sequence of the wild-type enzyme, such as amino acid sequences having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the amino acid sequence of the wild-type enzyme.

(Genes Encoding Enzymes (1) and (2))

The genes encoding the enzymes (1) and (2) may have any base sequence as long as such a base sequence encodes an amino acid sequence of an enzyme that has the above-described enzymological properties, or preferably, the above-described enzymological properties and structural properties. The genes encoding the enzymes (1) and (2) are overexpressed in the transformant to produce the enzyme (1) and (2). As used herein, the term "expression of a gene" means that the enzyme encoded by a gene is produced via transcription and translation in a form that exhibits its inherent catalytic activities. As used herein, the term "overexpression of a gene" means that the protein (enzyme) encoded by an inserted gene is produced at a level exceeding the normal expression level of the protein in the host organism.

The genes encoding the enzymes (1) and (2) may be a gene that can produce the enzymes (1) and (2) via splicing after the gene introduced into the host organism is transcribed, or alternatively, it may be a gene that can produce enzymes (1) and (2) without requiring splicing after the transcription of the gene.

The genes encoding the enzymes (1) and (2) may not be completely identical to the inherent gene (i.e., wild-type gene) of the organism of origin: it may be any DNA fragment with a base sequence that hybridizes to the base sequence complementary to the base sequence of the wild-type gene under stringent conditions as long as the gene encodes an enzyme having at least the above-described enzymological properties.

As used herein, "the base sequence that hybridizes under stringent conditions" refers to a DNA base sequence obtained by colony hybridization, plaque hybridization, southern blot hybridization and other suitable hybridization techniques using a DNA fragment having the base sequence of the wild-type gene as a probe.

As used herein, the term "stringent condition" refers to a condition under which the signals from specific hybrids can be clearly distinguished from the signals from non-specific hybrids and may vary depending on the hybridization system used, type of the probe, and the sequence and its length. Such conditions may be determined by varying the hybridization temperature or by varying the washing temperature and the salt concentration. For example, if even the signals from non-specific hybrids are strongly detected, the specificity can be increased by increasing the temperature for the hybridization and the washing temperature and if necessary, by decreasing the salt concentration for the washing. In contrast, if even the signals from specific hybrids are not detected, the hybrids may be stabilized by decreasing the temperature for the hybridization and the washing and if necessary, by increasing the salt concentration for the washing.

A specific example of the stringent condition involves using a DNA probe as a probe and carrying out the hybridization overnight (approximately 8 to 16 hours) using 5×SSC, 1.0(w/v) % blocking reagent for nucleic acid hybridization (Boehringer Mannheim), 0.1(w/v) % N-lauroylsarcosine, and 0.02(w/v) % SDS. The washing may be performed twice for 15 min each, using 0.1 to 0.5×SSC and 0.1(w/v) % SDS, preferably 0.1×SSC and 0.1(w/v) % SDS. The temperature to carry out the hybridization and the washing is 65° C. or higher, preferably 68° C. or higher.

Examples of the DNA having a base sequence that hybridizes under stringent conditions include DNA having the base sequence of the wild-type gene originating from a colony or plaque; DNA obtained by carrying out hybridization under stringent conditions using a filter on which fragments of the DNA are immobilized; and DNA identified by carrying out hybridization at 40 to 75° C. in the presence of 0.5 to 2.0 M NaCl, preferably at 65° C. in the presence of 0.7 to 1.0 M NaCl, and subsequently washing the filter at 65° C. using 0.1 to 1×SSC solution (a 1×SSC solution contains 150 mM sodium chloride and 15 mM sodium citrate). The preparation of the probe and the hybridization can be performed according to the procedures described in textbooks such as Molecular Cloning: A laboratory Manual, 2nd-Ed., Cold Spring Harbor Laboratory, Cold Spring Harbor, N.Y., 1989, Current Protocols in Molecular Biology, Supplement 1-38, John Wiley & Sons, 1987-1997 (These literature will be referred to as reference literature, hereinafter. The entire disclosure of reference literature is incorporated herein by reference). Those skilled in the art would adequately determine the conditions for obtaining DNA having a base sequence that hybridizes to the base sequence complementary to the base sequence of the wild-type gene under stringent conditions by considering, in addition to the above-mentioned conditions such as the salt concentration of buffers and the temperature, other conditions such as the probe concentrations, probe lengths, and the reaction time.

Examples of the DNA having a base sequence that hybridizes under stringent conditions include a DNA having a particular percentage or higher sequence identity to the base sequence of the DNA used as a probe having the base sequence of the wild-type gene, such as DNA having 80% or higher, preferably 85% or higher, more preferably 90% or higher, 91% or higher, 92% or higher, 93% or higher, 94% or higher, 95% or higher, 96% or higher, 97% or higher, 98% or higher, or 99% or higher, still more preferably 99.5% or higher sequence identity to the base sequence of the wild-type gene.

Examples of the base sequence that hybridizes to a base sequence complimentary to the base sequence of the wild-type gene under stringent conditions include base sequences resulting from deletion, substitution, addition or other modification of from 1 to several, preferably from 1 to 50, more preferably from 1 to 30, even more preferably from 1 to 20, still even more preferably 1, 2, 3, 4, 5, 6, 7, 8, 9 or 10 bases in the base sequence of the wild-type gene. As used herein, the term "deletion of a base" means that a base is lost or eliminated from the sequence. The term "substitution of a base" means that a base is replaced another base. The term "addition of a base" means that a new base is added to the sequence by inserting it into the sequence.

While the enzyme encoded by a base sequence that hybridizes to a base sequence complementary to the base sequence of the wild-type gene under stringent conditions should be an enzyme having an amino acid sequence resulting from deletion, substitution, addition or other modification of 1 to several amino acids in the amino acid sequence of the enzyme encoded by the base sequence of the wild-type gene, it has the same enzymatic activities as the enzyme encoded by the base sequence of the wild-type gene.

(Means for Calculating Sequence Identity)

While the sequence identity between base sequences or amino acid sequences may be determined by any method, it can be determined by using a commonly known method, whereby a wild-type gene or an amino acid sequence of an enzyme encoded by the wild-type gene is aligned with a base sequence or amino acid sequence of interest and the percent match between the two sequences is calculated using a program.

The algorithm of Karlin and Altschul is a known program for calculating the percent match between two amino acid sequences or base sequences (Proc Natl. Acad. Sci. USA 87: 2264-2268, 1990; Proc. Natl. Acad. Sci. USA 90: 5873-5877, 1993). Using this algorithm, Altschul et al. developed the BLAST program (J. Mol. Biol. 215: 403-410, 1990). The Gapped BLAST program, which can determine the sequence identity in a more sensitive way than the BLAST, is also known (Nucleic Acids Res. 25: 3389-3402, 1997). Using the above-described programs, one skilled in the art can search in a database for a sequence with a high sequence identity to a given sequence. These programs are available on the website of U.S. National Center for Biotechnology Information (blast.ncbi.nlm.nih.gov/Blast.cgi)

While the above-described methods are commonly used in the search of sequences with certain sequence identities from a database, Genetyx network model, version 12.0.1 (Genetyx corporation) may also be used in a homology analysis to determine the sequence identity of individual sequences. This method is based on the Lipman-Pearson method (Science 227:1435-1441, 1985). When analyzing the sequence identity of base sequences, regions encoding proteins (CDS or ORF) are used when possible.

(Origins of Genes Encoding Enzymes (1) and (2))

The genes encoding the enzymes (1) and (2) are, for example, derived from species having the ability to produce selenoneine or the ability to produce ergothioneine, or species expressing the enzymes (1) and (2). Examples of the organisms of origin from which the genes encoding the enzymes (1) and (2) are derived include microorganisms. Of various microorganisms, filamentous fungi are preferred since many of their species are known to have the ability to produce ergothioneine. Examples of the filamentous fungi include fungi of the genus *Aspergillus*. Specific examples include *Aspergillus sojae, Aspergillus oryzae, Aspergillus niger, Aspergillus tamarii, Aspergillus awamori, Aspergillus usamii, Aspergillus kawachii,* and *Aspergillus saitoi*.

*Aspergillus sojae, Aspergillus oryzae, Aspergillus niger, Aspergillus tamarii, Aspergillus awamori, Aspergillus usamii, Aspergillus kawachii,* and *Aspergillus saitoi* listed above as specific examples of the filamentous fungi of the genus *Aspergillus* have long been used in the production of miso paste, soy sauce, Japanese sake, shochu liquor and other fermented products, as well as in the production of citric acid and enzymes such as amylases. Their high enzyme productivity and high reliability for the safety, backed by long history of use, make these microorganisms useful in industrial applications.

As described above, while the organisms of origin from which the enzymes (1) and (2) are derived are not particularly limited, the enzymes (1) and (2) expressed in the transformant might not be deactivated by the growth conditions of the host organisms or the enzymes might show their respective activities. For this reason, it is preferred that the organism of origin from which the genes encoding the enzymes (1) and (2) are derived be a microorganism that grows under conditions similar to the growth conditions of a host organism to be transformed by the insertion of the genes encoding the enzymes (1) and (2).

(Cloning of Genes Encoding Enzymes (1) and (2) Lasing Genetic Engineering Technique)

The genes encoding the enzymes (1) and (2) can be inserted into various suitable known vectors. The resulting vector can then be introduced into a suitable known host organism to create a transformant in which the recombinant vector (recombinant DNA) containing the genes encoding enzymes (1) and (2) has been introduced. A person skilled in the art can appropriately select a suitable method for obtaining the genes encoding the enzymes (1) and (2), a method for obtaining the gene sequence encoding the enzymes (1) and (2) and the amino acid sequence information of the enzymes (1) and (2), as well as a method for creating different vectors and a method for creating transformants. The terms "transformation" and "transformant" as used herein encompass transduction and transductants, respectively. One non-limiting example of cloning of the genes encoding the enzymes (1) and (2) will be described below.

Cloning of the genes encoding the enzymes (1) and (2) may suitably use commonly used gene cloning techniques. For example, using a standard technique such as the technique described in the reference literature, the chromosomal DNA and mRNA can be extracted from microorganisms and various cells capable of producing the enzymes (1) and (2). The extracted mRNA can be used as a template to synthesize cDNA. The resulting chromosomal DNA and cDNA may be used to construct a library of chromosomal DNA or cDNA.

For example, genes encoding the enzymes (1) and (2) can be obtained by cloning from the chromosomal DNA or cDNA derived from microorganisms having the genes, which serves as a template. The organisms of origin from which the genes encoding the enzymes (1) and (2) are derived are as described above; specific examples include *Aspergillus sojae* NBRC4239 strain and *Aspergillus oryzae* RIB40 strain. For example, the *Aspergillus sojae* NBRC4239 strain is cultured and the resulting cells are dehydrated and physically triturated using a mortar while chilled in liquid nitrogen to form fine powder-like cell debris, from which a fraction containing chromosomal DNA is extracted using a standard technique. A commercially available DNA extraction kit such as DNeasy Plant Mini Kit (Qiagen) can be used to extract the chromosomal DNA.

Subsequently, a polymerase chain reaction (referred to as PCR, hereinafter) was conducted using the chromosomal DNA as a template along with synthetic primers complementary to the sequences at the 5' and 3' ends. The primers are not particularly limited as long as they can amplify DNA fragments containing the gene. Examples of the primers include primers shown in SEQ ID NOs: 17 to 22 designed based on the genome sequence of *Aspergillus sojae*. These primers can amplify the full length of the target gene and can therefore eliminate the need for RACE. Alternatively, DNA sequences containing fragments of the target gene may be amplified using suitable PCR techniques such as 5' RACE and 3' RACE and these sequences are subsequently ligated to obtain a DNA segment containing the full length target gene.

The method for obtaining the genes encoding the enzymes (1) and (2) is not particularly limited; for example, rather than using genetic engineering techniques, the genes encoding the enzymes) and (2) may be constructed by chemical synthesis.

For example, the base sequences of the amplification products amplified by PCR and the chemically synthesized genes may be determined as follows. First, the DNA segment to be sequenced is inserted into a suitable vector according to the standard technique to prepare a recombinant DNA. For cloning into a vector, a commercially available kit, such as TA Cloning Kit (Invitrogen); commercially available plasmid vector DNA, such as pUC119 (Takara Bio), pUC18 (Takara Bio), pBR322 (Takara Bio), pBluescript SK+(Stratagene), and pYES2/CT (Invitrogen); and commercially available bacteriophage vector DNA, such as λEMBL3 (Stratagene), may be used. The recombinant DNA is then used to transform host organisms, such as *Escherichia coli*, preferably *E. coli* JM109 strain (Takara Bio) and *E. coli* DH5α strain (Takara Bio). The recombinant DNA present in the transformant is then purified using a purification kit such as QIAGEN Plasmid Mini Kit (Qiagen).

The base sequences of genes inserted in the recombinant DNA are then determined by the dideoxy sequencing technique (Methods in Enzymology, 101, 20-78, 1983). The sequence analyzer used to determine the base sequence is not particularly limited; for example. Li-COR MODEL 4200L sequencer (Aloka), 370DNA sequencing system (Perkin Elmer), CEQ2000XL DNA analysis system (Beckman) may be used. The determined base sequences may then be used estimate the amino acid sequence of the translated proteins, thus, the enzymes (1), and (2).

(Construction of a Recombinant Vector Containing Genes Encoding Enzymes (1) and (2))

Recombinant vectors containing the genes encoding the enzymes (1) and (2) (recombinant DNA) can be constructed by connecting a PCR, amplification product containing any of the genes encoding the enzymes (1) and (2) with any of various vectors in such a manner that the recombinant vector can express the genes encoding the enzymes (1) and (2). For example, such a recombinant vector may be constructed by excising a DNA fragment containing any of the genes encoding the enzymes (1) and (2) with appropriate restriction enzyme and ligating the DNA fragment into a plasmid cut with appropriate restriction enzyme. The recombinant vector may also be obtained by connecting a DNA fragment containing the gene and having sequences homologous to a plasmid attached to the both ends with a DNA fragment derived from the plasmid amplified by inverse PCR using a commercially available recombinant vector preparation kit such as In-Fusion HD Cloning Kit (Clontech).

(Method for Creating a Transformant)

The method for creating a transformant for use in one embodiment of the production method is not particularly limited; for example, a gene(s) encoding the enzyme (1) or the enzymes (1) and (2) may be inserted in the host organisms according to a standard method in such a manner that the enzymes are expressed in the host organisms. Specifically, a DNA construct in which any of the genes encoding the enzymes (1) and (2) has been inserted between an expression-inducing promoter and a terminator is constructed. Subsequently, a host organism is transformed with only the DNA construct containing the gene encoding the enzyme (1) or with both the DNA construct containing the gene encoding the enzyme (1) and the DNA construct containing the gene encoding the enzyme (2) to obtain a transformant that overexpresses only the gene encoding the enzyme (1) or both the gene encoding the enzyme (1) and the gene encoding the enzyme (2). In the present specification, DNA fragments comprising an expression-inducing promoter—a gene encoding the enzyme (1) or (2)—a terminator and recombinant vectors containing the DNA fragment that are prepared to transform the host organism are collectively referred to as "DNA constructs."

The method for introducing the gene encoding the enzyme (1) or the enzymes (1) and (2) in a host organism in such a manner that the enzymes are expressed in the host organism is not particularly limited; for example, the gene may be directly introduced into the chromosome of the host organism by making use of homologous recombination, or the gene may be connected to a plasmid vector, which in turn is introduced into the host organism.

In the method that makes use of homologous recombination, a DNA construct may be connected between sequences homologous to the upstream region and the downstream region of a recombination site on a chromosome and inserted into the genome of the host organism. As a result of this self-cloning, a transformant can be obtained in which the gene is overexpressed under control of a high expression promoter in the DNA construct. The high expression promoter may be any high expression promoter, including, for example, a promoter region of translation elongation factor TEF1 gene (tef1), a promoter region of α-amylase gene (amy), a promoter region of alkaline protease gene (alp), and other suitable promoters.

In the method that makes use of a vector, a DNA construct is integrated into a plasmid vector used to transform host microorganisms using a standard method and a corresponding host organism can be transformed with the plasmid vector according to a standard method.

A suitable vector—host system may be any system that allows the production of the enzyme (1) or the enzymes (1) and (2) in the host organisms, including, for example, a system based on pUC19 and a filamentous fungus, and a system based on pSTA14 (Mol. Gen. Genet. 218, 99-104, 1989) and a filamentous fungus.

While the DNA construct is preferably introduced into the chromosome of the host organisms, it may be used without introducing into the chromosome by integrating into a self-replicating vector (Ozeki et al. Biosci. Biotechnol. Biochem. 59, 1133 (1995)).

The DNA construct may contain a marker gene that allows the selection of transformed cells. Examples of the marker gene include, but are not limited to, genes compensating for the nutritional requirements of the host organisms, such as pyrG, niaD and adeA; and drug-resistant genes such as those against pyrithiamine, hygromycin B and oligomycin. Also, the DNA construct preferably contains a promoter, a terminator and other regulatory sequences (such as enhancer and polyadenylated sequences) that enable the overexpression of the genes encoding the enzyme (1) or the enzymes (1) and (2) in the host organisms. The promoter may be any suitable expression-inducing promoter or constitutive promoter, including, for example, tef1 promoter, alp promoter, and amy promoter. The terminator may also be any terminator, including, for example, alp terminator, amy terminator, and tef1 terminator.

The regulatory sequences for the genes encoding the enzymes (1) or (2) in the DNA construct are not necessarily required if the DNA fragments containing the genes encoding the enzymes (1) or (2) contain sequences having expression regulatory functions. Also, when transformation is performed by the cotransformation method, the DNA construct may not contain any marker genes.

Purification tags may be added to the DNA construct. For example, a suitable linker sequence may be added to the upstream or downstream of the gene encoding the enzymes (1) or (2) and six or more codons of histidine-encoding base sequences may be added to the linker to enable the purification on a nickel column.

One embodiment of the DNA construct is, for example, a DNA construct in which a tef1 gene promoter, a gene encoding the enzymes (1) or (2), an alp gene terminator and a pyrG marker gene are connected to the In-Fusion cloning Site located in the multiple cloning site of pUC19.

Any properly selected method known to those skilled in the art may be used for transformation into filamentous fungi; for example, the protoplast PEG technique in which protoplasts of a host organism are prepared and polyethylene glycol and calcium chloride are added may be used (See, for example, Mol. Gen. Genet. 218, 99-104, 1989, Japanese Unexamined Patent Application Publication No. 2007-222055). The culture medium to regenerate the transformant is properly selected depending on the host organism and the transformation marker gene used. For example, when *Aspergillus sojae* is used as the host organism and pyrG gene is used as the transformation marker gene, the transformant can be regenerated in a Czapek-Dox minimal medium (Difco) containing 0.5% agar and 1.2M sorbitol.

Alternatively, in order to obtain the transformant for use in one embodiment of the production method, the endogenous promoter for the gene(s) encoding the enzyme (1) or the enzymes (1) and (2) present on the chromosome of the host organism may be substituted with a high expression promoter such as tef1 by homologous recombination. Again, a transformation marker gene such as pyrG is preferably inserted in addition to the high expression promoter. For example, a transformation cassette consisting of the upstream region of the gene encoding the enzyme (1) or (2)—a transformation marker gene—a high expression promoter—all or a part of the gene encoding the enzyme (1) or (2) described in Example 1 and FIG. 1 of Japanese Unexamined Patent Application Publication No. 2011-239681 may be used for this purpose. In this case, the upstream region of the gene encoding the enzyme (1) or (2) and all or a part of the gene encoding the enzyme (1) or (2) are used in homologous recombination. The all or a part of the gene encoding the enzyme (1) or (2) may include a region of the gene extending from the start codon to somewhere down the length of the gene. A suitable length of the region is preferably 0.5 kb or longer for homologous recombination.

In order to confirm that the transformant has successfully been created, the transformant may be cultured under a condition that induces the enzymatic activities of the enzyme (1) or the enzymes (1) and (2) and subsequently the resulting culture may be examined for the presence of selenoneine or alternatively, a comparison may be made to determine if the amount of selenoneine present in the resulting culture is greater than the amount of selenoneine present in a culture of the host organism cultured under the same condition.

Alternatively, the confirmation of successful creation of the transformant for use in one embodiment of the production method may be achieved by extracting the chromosomal DNA from the transformant, and performing a PCR using the chromosomal DNA as a template to detect the presence of any PCR product that can be amplified if the transformation has occurred.

For example, a PCR can be performed using a combination of a forward primer for the base sequence of the promoter used and a reverse primer for the base sequence of the transformation marker gene and whether the product having an expected length is produced is determined.

When the transformation is carried out by homologous recombination, it is preferred to perform a PCR using a forward primer located upstream of the upstream homologous region used and a reverse primer located downstream of the downstream homologous region used and then determine whether the product having a length expected when the homologous recombination has occurred is produced.

(Host Organism)

The host organism may be any microorganism that can produce the enzyme (1) or the enzymes (1) and (2) when transformed by a DNA construct containing the gene encoding the enzyme (1) or DNA constructs containing the genes encoding the enzymes (1) and (2), respectively. Examples include, but are not limited to, microorganisms in which selenium can be metabolized in view of the toxicity of the selenium compound, preferably microorganisms that can express selenic acid reductase (EC1.97.1.9), selenocysteine lyase (EC4.4.1.16), serine dehydratase (EC4.3.1.17) or two or more of those enzymes, more preferably filamentous fungi such as the genus *Aspergillus*, the genus *Escherichia*, the genus *Trichoderma*, the genus *Fusarium*, the genus *Penicillium*, the genus *Rhizopus*, and the genus *Neurospora*, photosynthetic microorganism and probiotic microorganism.

For example, it is known that microorganisms such as the genus *Acinetobacter*, the genus *Aeromonas*, the genus *Arthrobacter*, the genus *Bacillus*, the genus *Candida*, the genus *Cephalosporium*, the genus *Citrobacter*, the genus *Corynebacterium*, the genus *Flavobacterium*, the genus *Fusarium*, the genus *Micrococcus*, the genus *Neurospora*, the genus *Penicillium*, the genus *Pseudomonas*, the genus *Salmonella*, the genus *Scopulariopsis*, the genus *Selenomonas* have an oxidation or reducing ability for selenium compound (refer to D. T. Maiers et al., APPLIED AND ENVIRONMENTAL MICROBIOLOGY, October 1988, p. 2591-2593). Especially, selenate reductase or the gene, encoding the enzyme is found from *Thauera selenatis*, *Escherichia coli*, *Enterobacter cloacae* and *Bacillus selenatarsenatis* (refer to SAKAGUCHI Toshifumi, "selenium oxyanion reductase and its gene", Biomedlca, 2012. Vol. 3, p. 133). Also, it is known that *Alcaligenes viscolactis*, *Escherichia freundii*, *Corynebacterium pseuclocliphtheriticum*, *Pseudomonas alkanolytica*, *Brevibacterium leucinophagum*, *Escherichia coli*, *Erwinia carotovora*, *Serratia marcescens*, *Alcaligenes bookeri*, *Aspergillus ficuum*, *Aspergillus sojae*, *Absidia corymbifera*, *Neurospora crassa*, *Penicillium expansum*, *Saccharomyces cerevisiae*, *Kluyveromyces fragilis*, *Candida albicans*, *Hansenula beckii* and *Schwanniomyces occidentalis* have a selenocysteine lyase activity or a possibility of said activity (refer to PATRICK CHOCAT et al., JOURNAL OF BACTERIOLOGY, October 1983, p. 455-457). Thus, those microorganisms can be used as host organisms. Also, beyond those microorganisms, any other microorganisms having the reinforced selenium metabolism gene or the expression of the heterologous gene can be used as host organisms. Further, it may be possible that the microorganism can be used as the organism of origin from which the gene encoding the enzymes (1) or (2) are derived.

Among them, the host organism is more preferably any of the microorganisms of filamentous fungi in which the production of ergothioneine is detected and filamentous fungi that have genes encoding the enzymes (1) and (2) on their genomic DNA. Specific examples of the filamentous fungi include filamentous fungi described in Donald et al. document (Donald B. Melville et al, J. Biol. Chem. 1956, 223:9-17, the entire disclosure of which is incorporated herein by reference) and Dorothy et al. document (Dorothy S. Genghof, J. Bacteriology, August 1970, p. 475-478, the entire disclosure of which is incorporated herein by reference), such as filamentous fungi belonging to the genus *Aspergillus*, the genus *Neurospora*, the genus *Penicillium*, the genus *Fusarium*, the genus *Trichoderma*, and the genus *Mucor*. Examples of the filamentous fungi that have genes encoding the enzymes (1) and (2) on their genomic DNA include filamentous fungi belonging to the genus *Neosartorya*, the genus *Byssochlamys*, the genus *Talaromyces*, the genus *Ajellomyces*, the genus *Paracoccidioides*, the genus *Uncinocarpus*, the genus *Coccidioides*, the genus *Arthroderma*, the genus *Trichophyton*, the genus *Exophiala*, the genus *Capronia*, the genus *Cladophialophora*, the genus *Macrophomina*, the genus *Leptosphaeria*, the genus *Bipolaris*, the genus *Dothistroma*, the genus *Pyrenophora*, the genus *Neofusicoccum*, the genus *Setosphaeria*, the genus *Baudoinia*, the genus *Gaeumannomyces*, the genus *Marssonina*, the genus *Sphaerulina*, the genus *Sclerotinia*, the genus *Magnaporthe*, the genus *Verticillium*, the genus *Pseudocercospora*, the genus *Colletotrichum*, the genus *Ophiostoma*, the genus *Metarhizium*, the genus *Sporothrix*, and the genus *Sordaria*.

Of these filamentous fungi, in terms of the safety and easy culturing, the host filamentous fungus is preferably any of the microorganisms of the genus *Aspergillus* listed above as the organisms of origin from which the genes encoding the enzymes (1) and (2) are derived, including *Aspergillus sojae*, *Aspergillus oryzae*, *Aspergillus niger*, *Aspergillus tamarii*, *Aspergillus awamori*, *Aspergillus usamii*, *Aspergillus kawachii*, and *Aspergillus saitoi*.

(Specific Examples of Genes Encoding Enzymes (1) and (2))

Examples of the gene encoding the enzyme (1) derived from the *Aspergillus sojae* NBRC4239 strain include a gene AsEgtA, which will be described in Examples below. Examples of the gene encoding the enzyme (2) derived from the *Aspergillus sojae* NBRC4239 strain include genes AsEgtB and AsEgtC, which will be also described in Examples below. The base sequences of the genes AsEgtA, AsEgtB and AsEgtC are shown in SEQ ID NOs: 1 to 3 in the sequence listing, respectively. Further, the amino acid sequences of the AsEgtA, AsEgtB and AsEgtC proteins are shown in SEQ ID NOs: 4 to 6 in the sequence listing, respectively.

Examples of the gene encoding the enzyme (1) derived from the *Aspergillus oryzae* RIB40 strain include a gene AoEgtA, which will be described in Examples below. The base sequence of the gene AoEgtA is shown in SEQ ID NO: 23 in the sequence listing. Further, the amino acid sequence of the AoEgtA protein is shown in SEQ ID NO: 24 in the sequence listing.

Genes encoding the enzymes (1) and (2) may be obtained from microorganisms other than those of *Aspergillus sojae* and *Aspergillus oryzae* by any suitable method. For example, a homology search by BLAST may be conducted on the genomic DNA of microorganisms other than those of *Aspergillus sojae* and *Aspergillus oryzae* based on the base sequences of the genes AsEgtA, AsEgtB, AsEgtC and AoEgtA (SEQ ID NOs: 1 to 3 and 23) and the amino acid sequences of the AsEgtA, AsEgtB, AsEgtC and AoEgtA proteins (SEQ ID NOs: 4 to 6 and 24), to identify genes having a base sequence with a high sequence identity to the base sequences of the genes AsEgtA, AsEgtB, AsEgtC and AoEgtA. Alternatively, genes encoding the enzymes (1) and (2) may be obtained by identifying proteins having a high sequence identity to the AsEgtA, AsEgtB, AsEgtC and AoEgtA proteins from the total protein of microorganisms other than those of *Aspergillus sojae* and *Aspergillus oryzae* and identifying the genes encoding these proteins. Whether the resulting genes are equivalent to the genes encoding the enzymes (1) and (2) can be determined by transforming the organism of origin as the host organism with the obtained gene and determining if selenoneine is produced or determining if the production of selenoneine is enhanced compared to the host organisms.

Since *Aspergillus sojae*, *Aspergillus oryzae* and *Aspergillus niger* grow under similar conditions, it may be possible to insert the genes of the respective fungi into one another to mutually transform the respective fungi. For example, a gene(s) encoding the enzyme (1) or the enzymes (1) and (2) derived from *Aspergillus sojae* may be introduced into the host organism of *Aspergillus oryzae* or *Aspergillus niger* to transform them. In order to ensure that the enzyme (1) or the enzymes (1) and (2) have the desired enzymatic activity, it is preferred that the organism of origin from which the genes encoding the enzyme (1) or the enzymes (1) and (2) are derived and the host organism are identical. For example, a gene(s) encoding the enzyme (1) or the enzymes (1) and (2) derived from *Aspergillus sojae* may be introduced into the same *Aspergillus sojae*.

The genes encoding the enzymes (1) and (2) may be genes optimized for their codons, secondary structures, and GC contents based on the amino acid sequence of the genes encoding the enzymes (1) and (2) derived from *Aspergillus sojae*. Specific examples of such genes include EcEgtA (SEQ ID NO: 27) and EcEgtC (SEQ ID NO: 28) synthesized for expression in *E. coli*.

One Embodiment of Transformant

One embodiment of the transformant for use in one embodiment of the production method is an *Aspergillus sojae* transformant obtained by introducing a gene AsEgtA into *Aspergillus sojae* for overexpression of AsEgtA protein.

Another embodiment of the transformant is *Aspergillus oryzae* transformant obtained by introducing a gene AoEgtA into *Aspergillus oryzae* for overexpression of AoEgtA protein. Such *Aspergillus sojae* and *Aspergillus oryzae* transformants are designed to overexpress the AsEgtA and AoEgtA proteins and are capable of producing selenoneine at detectable or higher levels while the respective host organisms can produce little or no selenoneine. In addition, the *Aspergillus sojae* and *Aspergillus oryzae* transformants can produce selenoneine not only from organic selenium compounds such as selenocysteine and selenocystine, but also from inorganic selenium compounds such as selenous acid, as will be described later in Examples. Accordingly, one embodiment of the transformant is preferably a transformant in which the expression of the gene or genes encoding the enzyme (1) or the enzymes (1) and (2) is enhanced such that the amount of selenoneine is increased as compared to the host organism. Also, one embodiment of the transformant is more preferably a transformant in which the expression of the genes encoding the enzymes (1) and (2) is enhanced such that the amount of selenoneine is increased as compared to transformants in which the expression of the gene encoding the enzyme (1) is enhanced.

As will be described later in Examples, when the *Aspergillus sojae* transformant transformed to overexpress the AsEgtA protein was cultured in DPY medium suitable for the growth of the host *Aspergillus sojae* at 30° C. for 4 to 5 days, 15.8 μg of selenoneine was obtained per gram of wet cell mass when selenous acid was used and 207.9 μg of selenoneine was obtained per gram of wet cell mass when selenocystine was used. Accordingly, one embodiment of the transformant is a transformant in which the expression of the gene or genes encoding the enzyme (1) or the enzymes (1) and (2) is enhanced such that when the transformant is cultured at 30° C. for 5 days in a selenium compound-containing culture medium suitable for the growth of the host organism, the amount of selenoneine produced is for example 5 μg or more, preferably 10 μg or more, more preferably 20 μg or more, and still more preferably 40 μg or more per gram of wet cell mass. One embodiment of the transformant is a transformant in which the expression of the gene or genes encoding the enzyme (1) or the enzymes (1) and (2) is enhanced such that when the transformant is cultured at 30° C. for 5 days in a selenous acid-containing culture medium suitable for the growth of the host organism, the amount of selenoneine produced is for example 5 μg or more, preferably 6 μg or more, more preferably 10 μg or more, and still more preferably 15 μg or more per gram of wet cell mass. One embodiment of the transformant is a transformant in which the expression of the gene or genes encoding the enzyme (1) or the enzymes (1) and (2) is enhanced such that when the transformant is cultured at 30° C. for 5 days in a selenocystine-containing culture medium suitable for the growth of the host organism, the amount of selenoneine produced is for example 10 μg or more, preferably 20 μg or more, more preferably 40 μg or more, even more preferably 100 μg or more, and yet more preferably 200 μg or more per gram of wet cell mass.

The transformant for use in one embodiment of the production method may produce, along with the enzymes (1) and (2) expressed by the introduced gene encoding the enzymes (1) and (2), wild-type enzymes (1) and (2) that have the same or different structural properties from the enzymes (1) and (2) and that are expressed by the endogenous genes of the host organism encoding the enzymes (1) and (2). Consequently, the transformant for use in one embodiment of the production method can produce selenoneine even if the gene encoding the enzyme (2) is not introduced.

The transformant for use in one embodiment of the production method includes a transformed archaebacterium or a transformed bacterium that has the genes encoding the enzymes (1) and (2) introduced therein and that overexpresses the introduced genes. Non-limiting examples of the transformed bacteria include transformed *E. coli* transfected with a plasmid vector containing EcEgtA or EcEgtA and EcEgtC.

(Production Method)

One embodiment of the production method is a method for producing selenoneine comprising the step of applying histidine and a selenium compound to a transformant that has the gene or genes encoding the enzyme (1) or the enzymes (1) and (2) introduced therein and that can overexpress the introduced genes, to obtain selenoneine.

The method for applying histidine and a selenium compound to the transformant is not particularly limited and may be any method that can expose the transformant to histidine and the selenium compound to allow the enzymes of the transformant to produce selenoneine. For example, the transformant may be cultured in a culture medium containing histidine and selenium compound and optimized for the growth of the transformant under culture conditions suitable for the transformant so as to produce selenoneine. The culture method is not particularly limited; for example, the solid culture or liquid culture technique performed under aerated or non-aerated condition may be employed. The amount of the selenium compound added is not particularly limited as long as the growth of the transformant is not inhibited. For example, the selenium compound may be present at sufficiently low levels relative to the cell concentration at the initial stage of culturing. Specifically, it is added at a concentration of 1 mM or less, preferably 0.1 mM or less, and more preferably 0.05 mM or less. When it is desired to obtain large amounts of selenoneine, the amount of the selenium compound added may be increased during the course of culture or as the cell concentration increases. For example, additional amounts of the selenium compound at a concentration of 0.001 to 10 mM, preferably 0.005 to 5 mM, may be added to the culture medium 1 to 24 hours, preferably 3 to 22 hours after the start of culture.

The culture medium may be any standard culture medium designed for culturing host organism and may be either a synthetic or natural culture medium that contains a carbon source, a nitrogen source, inorganic materials, and other nutrients at an appropriate ratio. When the host organism is a microorganism of the genus *Aspergillus*, the DPY medium as described in Examples below may be used, although not particularly limited. It is preferred, however, that the medium contain, as a component, iron (II) required for the activation of the enzyme (1). While iron (II) may be added to the medium in the form of a compound, it may also be added as a mineral-containing material.

The selenium compound is not particularly limited as long as it contains selenium as a constituent element. For example, it may be an organic or inorganic selenium compound or a salt thereof. Examples of organic selenium compounds and salts thereof include selenocysteine, selenocystine, selenomethionine, Se-(methyl)seleno-L-cysteine, selenopeptides, selenoproteins and salts thereof and selenium yeast. Examples of inorganic selenium compounds and salts thereof include selenic acid, selenous acid, selenium chloride, selenium, selenides, selenium sulfide, dimethylselenium, selenophosphate, selenium dioxide and salts thereof.

Alternatively, the selenium compound may be an organic material containing an organic or inorganic selenium compound or a salt thereof. Examples of such organic materials include, but are not limited to, bonito fish (processed products and dried bonito), mustard (powdered mustard, grain mustard and mustard paste), pork (kidney, liver, and raw meat), beef (kidney, raw meat), anglerfish (liver, raw meat), codfish (cod roe, raw meat), bluefin tuna (red meat, raw meat), flatfish (raw meat), bonito fish (those caught in the fall season, raw meat), snow crabs (raw meat), sunflower seeds (fried, flavored), horse mackerel (grilled), tilefish (raw meat), granular seasoning, yellow fin tuna (raw meat), albacore (raw meat), oyster (boiled), and other food products known to be a rich source of selenium. The selenium compound may be one of or a combination of two or more of these materials.

More preferably, the selenium compound is selenocysteine or selenocystine. While selenocysteine and selenocystine may be obtained by any suitable manner, selenocysteine for example may be produced with reference to JP 2001-61489 A.

The transformant for use in one embodiment of the production method may be any of the above-described transformants. For example, when an organic selenium compound such as selenocysteine and selenocystine is used as the selenium compound, the transformant may be a transformant that has the genes encoding the enzymes (1) and (2) introduced therein and that can overexpress the introduced genes. When an inorganic selenium compound such as selenous acid is used as the selenium compound, the transformant may be a transformant that has the gene encoding the enzyme (1) introduced therein and that can overexpress the introduced gene.

The culture condition of the transformant may be any culture condition of the host organism commonly known to those skilled in the art; for example, when the host organism is a filamentous fungus, the initial pH of the culture medium may be conditioned to 5 to 10 and the culture temperature to 20 to 40° C., and the culture time may be properly selected and may vary from several hours to several days, preferably from 1 to 7 days, and more preferably from 2 to 4 days. The culture means is not particularly limited; for example, an aerated, agitated, submerged culture, a shake culture, a static culture or other suitable culture techniques may be employed with the culture condition preferably adjusted so that sufficient amounts of dissolved oxygen are present. One example of the culture medium and culture condition for culturing microorganisms of the genus *Aspergillus* includes a shake culture in which the fungus is cultured at 30° C. under shaking at 160 rpm over 3 to 5 days in a DPY medium as described in Examples below.

The method for extracting selenoneine from the culture after completion of the culture is not particularly limited. For extraction purposes, the fungal cells collected from the culture by filtration, centrifugation or other manipulation may be used without further processing, or alternatively, the fungal cells dried or, if desired, triturated after collection may be used. The method for drying fungal cells is not particularly limited; for example, lyophilization, drying in the sun, hot-air drying, vacuum drying, aeration drying, drying under reduced pressure or other suitable drying techniques may be used.

The solvent used for extraction may be any solvent that can dissolve selenoneine, including, for example, organic solvents, such as methanol, ethanol, isopropanol and acetone; water-containing organic solvents composed of these organic solvents and water mixed together; and water, warm water and hot water. After addition of the solvent, selenoneine is extracted while the cells are triturated as necessary. The temperature of the extraction solvent may be set to from room temperature to 100° C.

In one embodiment of the extraction method of selenoneine, the fungal cells collected from the culture are washed with water and added to water to prepare a suspension. The resulting suspension is then subjected to a heat treatment such as at 100° C. for 15 minutes and then centrifuged to collect the supernatant. Subsequently, the collected supernatant is filtered to remove impurities.

Alternatively, the heated suspension may be directly filtered without centrifugation.

Instead of the heat treatment described above, the cells may be subjected to cell destruction processes that break cells using cell destruction means such as an ultrasonicator, a French press, a DYNO-MILL, and a mortar; processes for lysing the fungal cell walls with Yatalase and other cell wall-lysing enzymes; or processes for lysing the fungal cells with a surfactant such as SDS and Triton X-100. These processes may be used either individually or in combination.

In order to purify selenoneine, the resulting extract can be subjected to various purification processes including centrifugation, filtration, ultrafiltration, gel filtration, separation by solubility difference, solvent extraction, chromatography (adsorption chromatography, hydrophobic interaction chromatography, cation exchange chromatography, anion exchange chromatography, and reversed-phase chromatography), crystallization, active carbon treatment, membrane treatment, and other purification processes.

The qualitative or quantitative analysis technique of selenoneine is not particularly limited; the analysis may be conducted by, for example, LC-MS or LC-ICP-MS. A person skilled in the art would properly select the conditions for the analysis; for example, the analysis may be performed using the conditions described in Examples below.

According to one embodiment of the production method, selenoneine can be obtained at high yields. For example, FIG. S6 and FIG. 3B of Non-Patent Document 2 indicates the amount of ergothioneine produced after culturing in a selenium-free culture medium and also indicates the peak ratio of ergothioneine and selenoneine as a result of culturing in a selenium-containing culture medium. Considering these results together, the amount of selenoneine produced is estimated to be about 0.047 µg/ml. In comparison, the amount of selenoneine produced in one embodiment of the production method is calculated to be 14.56 µg/ml from the determined value of 6.46 µg-Se/ml (amount of selenium alone), as will be later described in Examples. This suggests that according to one embodiment of the production method, the production of selenoneine can be increased more than 100-fold as compared to the production method described in Non-Patent Document 2, providing a significant advantage.

In one embodiment of the production method, various other steps or manipulations may be performed before, after, or during the above-described step as long as the objectives of the present invention can be achieved.

Another embodiment of the production method is a production method that uses, rather than the transformant, a microorganism that has a gene or genes encoding the enzyme (1) or the enzymes (1) and (2) on its genomic DNA. For example, another embodiment of the production method is a method for producing selenoneine, the method comprising the step of applying histidine and a selenium compound to a fungus, including those of genus *Aspergillus*, such as *Aspergillus oryzae*, having a gene or genes encoding the enzyme (1) or the enzymes (1) and (2) on its genome DNA, to obtain selenoneine.

In one embodiment of the production method, selenoneine, the intended product, can cause growth inhibition or production inhibition in the microorganism used. Such grow inhibition or production inhibition in the microorganism may be avoided by adding an oxidizing agent such as copper ions to the culture medium to cause the produced selenoneine to dimerize (by formation of Se—Se linkage). Thus, in one embodiment of the production method, it is preferred that oxidizing agents such as copper ions are present during application of histidine and selenium compound to the microorganism.

(Applications of Selenoneine)

Having advantageous characteristics of being a functional biological material with various physiological activities, as well as being a heat-resistant, water-soluble material, the selenoneine obtained by the production method or the transformant to serve as one embodiment of the present invention is useful as general food and beverage products, functional food and beverage products, food and beverage products with function claims, food and beverage products for specified health use, food and beverage products with nutrient function claims, food and beverage products with health function claims, food and beverage products for special uses, nutritional supplement food and beverage products, health-promoting food and beverage products, supplements, beauty food and beverage products, cosmetic products, pharmaceutical products, quasi-pharmaceutical products, animal feeds, and raw-materials for producing these products.

Specifically, selenoneine is known to have antioxidant activity that is 1,000 times as high as that of it's thio analog, ergothioneine. For this reason, selenoneine can be useful as a biological antioxidant that exhibits the ability to capture hydroxyl radicals, the ability to suppress autoxidation of the hem iron, and other antioxidant activities. Examples of specific products containing selenoneine include, but are not limited to, supplements that can substitute selenous acid and selenomethionine, prophylactic or therapeutic agents for cancers and lifestyle-related diseases such as ischemic heart diseases, and antidotes for methyl mercury.

The present invention will now be described in further detail with reference to the following Examples, which are not intended to limit the present invention. The present invention may take various forms to the extent that the objectives of the present invention are achieved.

EXAMPLES

Example 1: Preparation of DNA Constructs with an Inserted Gene AsEgtA, AsEgtB or AsEgtC (1) Searching of Genes of Interest NCU04343 and NCU11365 are among the enzymes known to be involved in the biosynthesis of ergothioneine in *Neurospora crassa* (See, Non-Patent Documents 3 and 4). Non-Patent Document 3 also suggests the possible involvement of NCU04636 in the biosynthesis of ergothioneine. Given that, using genes encoding the three enzymes of *Neurospora crassa* as query sequences, domains with a relatively high sequence identity to the genes encoding each of NCU04343, NCU04636 and NCU11365 were searched based on the genome sequence of the NBRC4239 strain of *Aspergillus sojae*. The search was conducted using a BLAST program (tblastn) and the genome sequence of the NBRC4239 strain of *Aspergillus sojae* (DDBJ/EMBL/Gen-Bank DNA databases, Accession numbers for the 65 scaffold sequences; DF093557-DF093585, DNA RESEARCH 18, 165-176, 2011).

As a result, a gene sho in SEQ ID NO: 1 was found as a sequence domain with a relatively high sequence identity to NCU04343. This gene was named as AsEgtA gene (SEQ ID NO: 1), indicating an egtA gene originating from *Aspergillus sojae*. Also, a gene shown in SEQ ID NO: 2 was found as a sequence domain with a relatively high sequence identity to NCU04636 and was named as AsEgtB gene (SEQ ID NO: 2). Further, a gene shown in SEQ ID NO: 3 was found as a sequence domain with a relatively high sequence identity to NCU11365 and was named as AsEgtC gene (SEQ ID NO: 3).

A comparison of the sequence identity on the amino acid level was performed using a gene information processing software Genetyx network model, version 12.0.1 (Genetyx) and indicated the sequence identities of the AsEgtA protein (SEQ ID NO: 4), the AsEgtB protein (SEQ ID NO: 5) and the AsEgtC protein (SEQ II) NO: 6) to NCU04343, NCU04636 and NCU11365 were 46%, 75% and 44%, respectively. Also, the sequence identity of AsEgtC protein, to SPBC660.12c, are ortholog of NCU11365 in *Schizosaccharomyces pombe*, was found to be 27%. These results suggest that the base sequences and the amino acid sequences of AsEgtA, AsEgtB and AsEgtC may be used to search for the egtA, egtB and egtC genes of other microorganisms of the genus *Aspergillus*.

(2) Extraction of Chromosomal DNA of *Aspergillus sojae* NBRC4239 Strain

In a 150 ml Erlenmeyer flask, 30 mL of a polypeptone-dextrin medium (1 (w/v) % polypeptone, 2 (w/v) % dextrin, 0.5 (w/v) % $KH_2PO_4$, 0.1 (w/v) % $NaNO_3$, 0.05 (w/v) % $MgSO_4 \cdot 7H_2O$, 0.1 (w/v) % casamino acid; pH 6.0) was prepared with distilled water. The medium was inoculated with the conidia of *Aspergillus sojae* NBRC4239 strain and was subjected to shake culture overnight at 30° C. The cells were collected from the resulting culture broth by filtration and were placed between sheets of paper towel to remove moisture. The cells were then triturated using a liquid nitrogen-chilled mortar and pestle while being chilled in liquid nitrogen. Using DNeasy Plant Mini Kit (Qiagen), the chromosomal DNA was extracted from the resulting triturated cells.

(3) Preparation of a Construct Plasmid

The following elements were integrated into plasmid pUC19 to make a plasmid for making a construct (construct plasmid): Ptef, a promoter sequence of translation elongation factor gene tef1 (a 748 bp upstream region of tef1 gene; SEQ ID NO: 7); Talp, a terminator sequence of alkaline protease gene alp (a 800 bp downstream region of alp gene; SEQ ID NO: 8); and pyrG, a transformation marker gene that compensates for the requirement for uridine (1838 bp including a 407 bp upstream region, a 896 bp coding region and a 535 bp downstream region; SEQ ID NO: 9). Specifically, the plasmid was prepared in the following manner.

Ptef, Talp and pyrG were amplified by PCR using chromosomal DNA of *Aspergillus sojae* NBRC4239 strain obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The PCR was performed according to the protocol provided with the enzyme. Printers used to amplify Ptef, Talp and pyrG and the PCR conditions are shown in Tables 1 to 3 below. Of the sequences shown in the tables, the sequences shown in lower case are added sequences that serve to connect the amplified fragments of Ptef, Talp and pyrG in this order and further connect them to pUC19. The amplified DNA fragments were separated in 1 (w/v) % agarose gel and purified using QIAquick Gel Extraction Kit (Qiagen).

TABLE 1

| Amplified target region | Pref |
|---|---|
| Forward primer SEQ ID NO: 10 | Ptef1_-748R_pUC cggtacccggggatcTGTGGACCAGACAGGCGCC ACTC |
| Reverse primer SEQ ID NO: 11 | Ptef1_-1R_Talp atgtactcctggtacTTTGAAGGTGGTGCGAACT TTGTAG |
| PCR condition | 2 min. at 94° C. (15 sec. at 94° C., 30 sec. at 62° C., 1 min. at 68° C.) × 25 cycles |

TABLE 2

| Amplified target region | Talp |
|---|---|
| Forward primer SEQ ID NO: 12 | Talp_1F GTACCAGGAGTACATTGGAGAGTTCTAC |
| Reverse primer SEQ ID NO: 13 | Talp_800R CCGATCCAACCACCCGGCTATCG |
| PCR condition | 2 min. at 94° C. (15 sec. at 94° C., 30 sec. at 62° C., 1 min. at 68° C.) × 25 cycles |

TABLE 3

| Amplified target region | pyrG |
|---|---|
| Forward primer SEQ ID NO: 14 | PyrG_-407_F_Talp gggtggttggatcggTTGGGCTTATTGCTATGT CCCTGAAAGG |
| Reverse primer SEQ ID NO: 15 | PyrG_1431R_pUC cgactctagaggatcCCGCACCTCAGAAGAAAA GGATGA |
| PCR condition | 2 min. at 94° C. (15 sec at 94° C., 30 sec. at 62° C., 2 min. at 68° C.) × 25 cycles | pUC19 used was pUC19 linearized Vector provided with In-Fusion HD Cloning Kit (Clontech). Using In-Fusion HD Cloning Kit described above, the amplified Ptef. Talp and pyrG were ligated into pUC19 at In-Fusion Cloning Site located in the multiple cloning site according to the protocols provided with the kit, to obtain a construct plasmid.

The resulting construct plasmid was used to transform competent cells ECOS Competent *E. coli* JM109 (Nippon Gene) in accordance with the manufacturer's instructions to obtain transformed *E. coli*.

The resulting transformed *E. coli* was then subjected to shake culture overnight at 37° C. in a LB liquid medium containing 50 μg/ml ampicillin. After the culture period, the culture solution was centrifuged to collect cells, Using FastGene Plasmid Mini Kit (Nippon Genetics), plasmid DNA was extracted from the collected cells according to the protocols provided with the kit.

(4) Preparation of a Construct for Inserting a Gene of Interest

A DNA construct consisting of genes of interest AsEgtA, AsEgtB or AsEgtC connected between Ptet and Talp of a construct plasmid was prepared as follows.

An inverse PCR was performed using the construct plasmid obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The inverse PCR was performed according to the protocol provided with the enzyme to obtain a vector fragment of the construct plasmid. Primers and the PCR conditions used are shown in Table 4 below. The amplified vector fragments were separated in 1 (w/v) % agarose gel and purified using QIAquick Gel Extractiom Kit (Qiagen).

TABLE 4

| Amplified target region | Construct plasmid |
|---|---|
| Forward primer SEQ ID NO: 16 | Ptef_-1R TTTGAAGGTGGTGCGAACTTTGTAG |
| Reverse primer SEQ ID NO: 12 | Talp_1F (above described) GTACCAGGAGTACATTGGAGAGTTCTAC |
| PCR condition | 2 min. at 94° C. (10 sec. at 98° C., 30 sec. at 65° C., 6 min. at 68° C.) × 20 cycles |

To amplify the genes AsEgtA (SEQ ID NO:1). AsEgtB (SEQ ID NO:2), and AsEgtC (SEQ ID NO: 3) derived from *Aspergillus sojae*, a PCR was performed using the chromosomal DNA of *Aspergillus sojae* NBRC4239 strain obtained above to serve as a template DNA, KOD-Plus-DNA Polymerase (Toyobo) to serve as PCR enzyme, the reagents provided with the enzyme to serve as reaction reagents, and Mastercycler gradient (Eppendolf) to serve as a PCR device. The PCR was performed according to the protocol provided with the enzyme. Primers used to amplify AsEgtA, AsEgtB and AsEgtC and the PCR conditions are shown in Tables 5 to 7 below. Of the sequences shown in the tables, the sequences shown in lower case are added sequences that serve to connect the amplified fragments to the construct plasmid (between Ptet and Talp). The amplified DNA fragments were separated in 1 (w/v) % agarose gel and purified using QIAquick Gel Extraction Kit (Qiagen).

TABLE 5

| Amplified target region | AsEgtA |
|---|---|
| Forward primer SEQ ID NO: 17 | EgtA_1F_Ptef cgcaccaccttcaaaATGTCACCTTTGGCTCTCTCTCC |
| Reverse primer SEQ ID NO: 18 | EgtA_2925R_Talp atgtactcctggtacCTAAAGATCCCGCACCAGGCGT |

TABLE 5-continued

| Amplified target region | AsEgtA |
|---|---|
| PCR condition | 2 min. at 94° C. (15 sec. at 94° C., 30 sec. at 62° C., 3 min. at 68° C.) × 25 cycles |

[Table 6]

TABLE 6

| Amplified target region | AsEgtB |
|---|---|
| Forward primer SEQ ID NO: 19 | EgtB_1F_Ptef cgcaccaccttcaaaATGTCTAATGTTACCCAATCAGCCTTGAG |
| Reverse primer SEQ ID NO: 20 | EgtB_1770R_Talp atgtactcctggtacTTAATGTTGACTCCATTGATCGTGTTCAG |
| PCR condition | 2 min. at 94° C. (15 sec. at 94° C., 30 sec. at 62° C., 2 min. at 68° C.) × 25 cycles |

TABLE 7

| Amplified target region | AsEgtC |
|---|---|
| Forward primer SEQ ID NO: 21 | EgtC_1F_Ptef cgcaccaccttcaaaATGACCACTCCCTTCGGAGCT |
| Reverse primer SEQ ID NO: 22 | EgtC_1529R_Talp atgtactcctggtacTCAAAGCTTCGCAGAAGAAACCCCAACC |
| PCR condition | 2 min. at 94° C. (15 sec. at 94° C., 30 sec. at 62° C., 2 min at 68° C.) × 25 cycles |

The vector fragments amplified as described above and AsEgtA, AsEgtB or AsEgtC were connected using In-Fusion HD Cloning Kit according to the protocol provided with the kit to obtain a DNA construct for inserting a gene of interest in which AsEgtA, AsEgtB or AsEgtC has been inserted. The so-obtained DNA construct consists of a DNA fragment derived from pUC19, DNA fragment of Ptef, a DNA fragment of AsEgtA, AsEgtB or AsEgtC, a DNA fragment of Talp, a DNA fragment of pyrG, and a DNA fragment derived from pUC19 that are connected in series in the direction from the 5' end to the 3' end. In other words, three different DNA constructs in which the sequence Ptef-AsEgtA, AsEgtB or AsEgtC-Talp-pyrG was connected sequentially into the MCS of pUC19 were obtained.

The resulting DNA constructs were used to transform competent cells EGOS Competent *E. coli* JM109 (Nippon Gene) in accordance with the manufacturer's instructions to obtain transformed *E. coli*.

The resulting transformed *E. coli* was then subjected to shake culture overnight at 37° C. in an LB liquid medium containing 50 μg/ml ampicillin. After the culture period, the culture solution was centrifuged to collect cells. Using FastGene Plasmid Mini Kit (Nippon Genetics), the plasmid DNA was extracted from the collected cells according to the protocols provided with the kit.

The base sequence of each DNA, inserted in the extracted plasmid DNA was determined to confirm that a DNA construct in which AsEgtA, AsEgtB or AsEgtC had been inserted was obtained.

Example 2: Preparation of Transformed *Aspergillus sojae* (1)

(1) pyrG-disrupted strain derived from *Aspergillus sojae* NBRC4239 strain.

Each DNA construct was precipitated with ethanol and dissolved in TE to form a DNA solution with a desired concentration. The DNA solution was then used to transform a pyrG-disrupted strain derived from the *Aspergillus sojae* NBRC4239 strain (i.e., the strain from which a 48 bp upstream region of the pyrG gene, a 896 by coding region, and a 240 hp downstream region of the pyrG gene have been deleted).

(2) Transformation of pyrG-Disrupted Strain Derived from the *Aspergillus sojae* NBRC4239 Strain In a 500 ml Erlenmeyer flask, conidia of the pyrG-disrupted strain derived from the *Aspergillus sojae* NBRC4239 strain were inoculated into 100 ml of a polypeptone dextrin liquid medium containing 20 mM uridine and the inoculated medium was subjected to drake culture at 30° C. for about 20 hours. Subsequently, the cells were collected. Protoplasts were prepared from the collected cells. The resulting protoplasts were then transformed with 20 μg of the DNA construct for inserting a gene of interest using the protoplast PEG technique and the protoplasts were incubated at 30° C. for 5 days or more in a Czapek-Dox minimal medium Difco; pH 6) containing 0.5 (w/v) % agar and 1.2 M sorbitol to obtain transformed *Aspergillus sojae* as the cells having the ability to form colonies.

Since pyrG, a gene that compensates for the requirement for uridine, had been introduced into the transformed *Aspergillus sojae*, the transformants were able to grow in the uridine-free medium and were selected as strains having the introduced target gene.

Example 3: Preparation of DNA Constructs with Inserted Gene AoEgtA (1) Search for Proteins of Interest Using the amino acid sequences of the AsEgtA protein of *Aspergillus sojae* as query sequences, proteins with high sequence identities were searched from the total protein of *Aspergillus oryzae* RIB40 strain. DOGAN (bio.nite.go.ip/dogan/project/view/AO) was used for the search.

As a result, AO090012000265 was identified as a protein with a relatively high sequence identity to the amino acid sequence of AsEgtA. AO090012000265 is described in Table 2 of Non-Patent Document No. 5 as a protein similar to Egt1 of *S. pombe*. AO090012000265 had a 97% sequence identity to the AsEgtA. The gene encoding AO090012000265 was designated as AoEgtA gene, indicating an egtA gene originating from *Aspergillus oryzae*. The amino acid sequence of AoEgtA protein is given in SEQ ID NO: 24.

(2) Extraction of Chromosomal DNA of *Aspergillus oryzae* RIB40 Strain

The same procedure was followed as in Example 1-(2), except that the conidia of *Aspergillus oryzae* RIB40 strain were used.

(3) Preparation of a Construct Plasmid

The vector fragments prepared in Example 1-(3) were used.

(4) Preparation of a Construct for Inserting a Gene of Interest

The same procedure was followed as in Example 1-(4) above, except that the gene of interest is the AoEgtA and the chromosomal DNA of *Aspergillus oryzae* RIB40 strain obtained above was used as a template DNA. Primers used to amplify AoEgtA and the PCR conditions are shown in Table 8 below.

TABLE 8

| Amplified target region | AoEgtA |
|---|---|
| Forward primer SEQ ID NO: 25 | AoEgtA_1F_Ptef cgcaccaccttcaaaATGTCACCGTTGGCTCT TTCTCC |
| Reverse primer SEQ ID NO: 26 | AoEgtA_2917R_Talp atgtactcctggtacCTAAAGATCCCGCACTA GGCGTG |
| PCR condition | 2 min. at 94° C. (15 sec. at 94° C., 30 sec. at 62° C., 3 min. at 68° C.) × 25 cycles |

Similar to Examples 1-(4) above, the base sequence of DNA inserted in the extracted plasmid DNA was determined to confirm that DNA constructs in which the AoEgtA had been inserted were obtained.

Example 4: Preparation of Transformed *Aspergillus oryzae*

The same procedure was followed as in Example 2-(1) and (2) above, except that a pyrG-disrupted strain derived from *Aspergillus oryzae* RIB40 strain as described in JP 2013-034416 A was transformed.

Example 5: Production of Selenoneine Using Transformed *Aspergillus sojae*

*Aspergillus sojae* NRBC4239 strain to serve as control and transformed *Aspergillus sojae* transformed with genes AsEgtA and AsEgtC were compared for their respective abilities to produce selenoneine in the following manner.

In a 200 mL Erlenmeyer flask, conidia of each of the fungal strains were inoculated into 40 ml of a selenocystine-supplemented DPY liquid medium (0.1 (w/v) % histidine, 1 mM selenocystine, 1 (w/v) % polypeptone, 2 (w/v) % dextrin, 0.5 (w/v) % yeast extract, 0.5 (w/v) % $KH_2PO_4$, 0.05 (w/v) % $MgSO_4·7H_2O$, 0.00017% $FeSO_4$; pH not adjusted) and the inoculated medium was subjected to shake culture at 160 rpm at 30° C. for 5 days. After the culture period, the cells were collected from the culture on Miracloth (Calbiochem). The collected cells were washed with 40 ml distilled water and were pressed between sheets of paper towel to remove moisture, thus giving wet cells, 8 ml water was then added and agitated to suspend the cells and form a cell suspension. The resulting cell suspension was subjected to a heat treatment at 100° C. for 15 min. Following the heat treatment, the suspension was centrifuged to collect the extracellular fluid as the supernatant, which in turn was filtered through a 0.45 μm filter to obtain a selenoneine extract.

The resulting selenoneine extract was subjected to LC-MS analysis under the following conditions.
[Conditions for LC-MS]
LC apparatus; Agilent 1100 series (Agilent)
Mass spectrometer; QSTAR Elite (AB Sciex)
Column; COSMOSIL HILIC (4.6×250 mm)
Eluent; acetonitrile+0.1% formic acid: water+0.1% formic acid=75: 25 (v/v)
Flow rate; 250 µl/ml
Detection; ESI positive
Injection; 10 µl
Temperature; room temperature The results of LC-MS analysis at m/z 278 corresponding to the protonated ions of selenoneine are shown in FIG. 1 for the *Aspergillus sojae* NBRC4239 strain and the transformed *Aspergillus sojae* transformed with AsEgtA and AsEgtC. As shown, the peak is very small for the *Aspergillus sojae* NBRC4239 strain, whereas it is clearly detected for the transformed *Aspergillus sojae* transformed with the genes AsEgtA and AsEgtC.

The results of LC-MS analysis at m/z 230 corresponding to the protonated ions of ergothioneine are shown in FIG. 2. As shown, the peak corresponding to ergothioneine is slightly detected for the *Aspergillus sojae* NBRC4239 strain, whereas the peak corresponding to ergothioneine is clearly detected for the transformed *Aspergillus sojae* transformed with the genes AsEgtA and AsEgtC.

Example 6: Confirmation of Selenoneine Production

FIG. 3 shows the enlarged MS spectrum of the peak at m/z 278 shown in FIG. 1 detected near 31-min retention time. The calculated values for the ion distribution of selenoneine estimated from the relative isotopic abundance are also shown in FIG. 4. That the measured values for the ion distributions showed a general match indicates that the peak is selenoneine, thus demonstrating production of selenoneine by the transformed *Aspergillus sojae* transformed with the genes AsEgtA and AsEgtC.

Example 7: Production of Selenoneine Using Transformed *Aspergillus sojae* (1)

In a 200 mL Erlenmeyer flask, conidia of the transformed *Aspergillus sojae* transformed with the genes AsEgtA and AsEgtC were inoculated into each of 40 ml of a DPY liquid medium; 40 ml of a selenous acid-supplemented DPY liquid medium (1 mM selenous acid, 0.1 (w/v) % histidine, 1 (w/v) % polypeptone, 2 (w/v) % dextrin, 0.5 (w/v) % yeast extract, 0.5 (w/v) % $KH_2PO_4$, 0.05 (w/v) % $MgSO_4·7H_2O$, 0.00017% $FeSO_4$; pH not adjusted); or 40 ml of a selenocystine-supplemented DPY liquid medium, and the inoculated medium was subjected to shake culture at 160 rpm at 30° C. for 5 days. After the culture period, the cells were collected from the culture on Miracloth (Calbiochem). The collected cells were washed with 40 ml distilled water and were pressed between sheets of paper towel to remove moisture, thus giving 2.28 g (selenocystine-supplemented DPY liquid medium) and 1.89 g (selenous acid-supplemented DPY liquid medium) of wet cells, 8 ml water was then added and agitated to suspend the cells and form a cell suspension. The resulting cell suspension was subjected to a heat treatment at 100° C. for 15 min. Following the heat treatment, the suspension was centrifuged to collect the extracellular fluid as the supernatant, which in turn was filtered through a 0.45 µm filter to obtain a selenoneine extract.

Each of the resulting selenoneine extracts was subjected to LC-MS analysis under the above-described conditions to determine the presence of selenoneine.

Selenoneine and total selenium were quantified by LC-ICP-MS according to the conditions described in the article by Yamashita et al. (THE JOURNAL OF BIOLOGICAL CHEMISTRY Vol. 285, No. 24, pp. 18134-18138, Jun. 11, 2010, "EXPERIMENTAL PROCEDURES", "Selenium Determination", the entire disclosure of which is incorporated herein by reference).

The results of LC-MS analysis at m/z 278 corresponding to selenoneine are shown in FIG. 5. Selenoneine was detected in the presence of selenocystine or selenous acid, but not in the DPY liquid medium alone. This confirms that selenoneine can be produced by using the transformed *Aspergillus sojae* in the presence of the selenium compound in the culture medium.

The selenoneine contents (selenium equivalents) of the selenoneine extracts were analyzed as described above and were determined to be 16.3 µg-Se/g of extract for the selenocystine-supplemented liquid medium and 4.6 µg-Se/g of extract for the selenous acid-supplemented liquid medium, respectively. The total selenium contents in the selenoneine extracts were measured by DAN fluorometry and were determined to be 20.8 µg/g of extract for the selenocystine-supplemented liquid medium and 8.1 µg/g of extract for the selenous acid-supplemented liquid medium, respectively. The amounts of selenoneine produced per gram of wet cell mass were determined to be 128.93 µg/g of wet cell mass for the selenocystine-supplemented liquid medium and 43.89 µg/g of wet cell mass for the selenous acid-supplemented liquid medium, respectively. These results indicate that considerable amounts of selenoneine can be obtained by using the transformed *Aspergillus sojae* in the presence selenocystine or selenous acid. DAN fluorometry is a technique involving wet heat digestion with a mixture of nitric acid/perchlorie acid, followed by reaction with 2,3-diaminonaphthalene (DAN). The fluorescence of the 4,5-Benzopiaselenol (Se-DAN) resulting from complexing with Se (IV) is then utilized to determine Se. The procedure was performed with reference to J. H. Watkinson, Anal. Chem, 38 (1) 92-97 (1966), the entire disclosure of which is incorporated herein by reference).

Example 8: Production of Selenoneine Using Transformed *Aspergillus sojae* (2)

The procedure was performed in the same manner as in Example 7 above, except that conidia of *Aspergillus sojae* NBRC4239 strain; transformed *Aspergillus sojae* transformed with the gene AsEgtA; transformed *Aspergillus sojae* transformed with the gene AsEgtA and AsEgtB; and transformed *Aspergillus sojae* transformed with the gene AsEgtA and AsEgtC were inoculated, and shake culture was conducted at 160 rpm at 30° C. for 4 days. The results were summarized in Tables 9 and 10.

TABLE 9

| Introduced gene | Selenium compound | Selenoneine concentration - Extract (Selenium equivalents) (mg-Se/L) | Wet cell weight (g) | Total extract volume (ml) | Selenoneine amount | |
|---|---|---|---|---|---|---|
| | | | | | Extract equivalents (μg/ml - extract) | Wet cell weight equivalents (μg/g - wet cell weight) |
| AsEgtA | selenocystine | 25 | 2.17 | 8 | 56.4 | 207.9 |
| AsEgtA + AsEgtB | selenocystine | 19.1 | 2.09 | 8 | 43.1 | 165 |
| AsEgtA + AsEgtC | selenocystine | 18.6 | 2.3 | 8 | 41.9 | 145.7 |
| AsEgtA | selenous acid | 2.1 | 2.37 | 8 | 4.7 | 15.8 |
| AsEgtA + AsEgtB | selenous acid | 1.3 | 2.58 | 8 | 2.9 | 9 |
| AsEgtA + AsEgtC | selenous acid | 1 | 2.78 | 8 | 2.3 | 6.6 |

TABLE 10

| Introduced gene | Selenium compound | Total Selenoneine concentration - Extract (mg/kg) | Wet cell weight (g) | Total extract volume (ml) |
|---|---|---|---|---|
| AsEgtA | selenocystine | 36.2 | 2.17 | 8 |
| AsEgtA + AsEgtB | selenocystine | 30.2 | 2.09 | 8 |
| AsEgtA + AsEgtC | selenocystine | 34.6 | 2.3 | 8 |
| AsEgtA | selenous acid | 5.7 | 2.37 | 8 |
| AsEgtA + AsEgtB | selenous acid | 4.1 | 2.58 | 8 |
| AsEgtA + AsEgtC | selenous acid | 4.1 | 2.78 | 8 |

These results indicate that considerable amounts of selenoneine can be obtained by using the transformed *Aspergillus sojae* in the presence selenocystine or selenous acid. Surprisingly, the transformed *Aspergillus sojae* transformed with the gene AsEgtA resulted in a greater amount of selenocysteine and a greater total selenium content than did either of the transformed *Aspergillus sojae* transformed with the gene AsEgtA and AsEgtB or the transformed *Aspergillus sojae* transformed with the gene AsEgtA and AsEgtC.

Example 9: Production of Selenoneine Using Transformed *Aspergillus oryzae*

*Aspergillus oryzae* RIB40 strain to serve as control and transformed *Aspergillus oryzae* transformed with genes AoEgtA were compared for their respective abilities to produce selenoneine in the following manner.

In a 200 mL Erlenmeyer flask, conidia of each fungal strain were inoculated into 40 ml of a selenocystine-supplemented DPY liquid medium, and the inoculated medium was subjected to shake culture at 160 rpm at 30° C. for 4 days. After the culture period, the cells were collected from the culture on Miracloth (Calbiochem). The collected cells were washed with 40 ml distilled water and were pressed between sheets of paper towel to remove moisture, thus giving 1.84 g of wet cell mass, 8 ml water was then added and agitated to suspend the cells and form a cell suspension. The resulting cell suspension was subjected to a heat treatment at 100° C. for 15 min. Following the heat treatment, the suspension was centrifuged to collect the extracellular fluid as the supernatant, which in turn was filtered through a 0.45 μm filter to obtain a selenoneine extract.

Each of the resulting selenoneine extracts was subjected to LC-MS analysis under the above-described conditions to determine the presence of selenoneine. Selenoneine was quantified by LC-ICP-MS according to the conditions described in the article by Yamashita et al.

The results of LC-MS analysis at m/z 278 corresponding to selenoneine are shown in FIG. 6. Selenoneine was detected as a slightly larger peak for the control strain of *Aspergillus oryzae* than for the *Aspergillus sojae* NBRC4239 strain. In comparison, the peak of selenoneine was clearly detected in the transformant transformed with the gene AoEgtA near 31.5-min retention time. These results indicate that considerable amounts of selenoneine can be obtained by using the transformed *Aspergillus oryzae*.

The selenoneine content (selenium equivalents) of the selenoneine extract was analyzed as described above and was determined to be 32.3 μg-Se/g of extract for the transformed *Aspergillus oryzae*. The amount of selenoneine produced per gram of wet cell mass was determined to be 316.58 μg/g of wet cell mass. The total selenium content in the selenoneine extract was measured by DAN fluorometry and was determined to be 39.1 μg-Se/g of extract.

Example 10: Toxicity of Selenium Compounds 0 mM, 0.1 mM, 0.3 mM or 1.0 mM selenocystine or selenous acid was added to a DPY liquid medium. To each of these media, conidia of *Aspergillus sojae* NBRC4239 strain to serve as control and transformed *Aspergillus sojae* transformed with the genes AsEgtA and AsEgtC were inoculated, and the inoculated media were subjected to shake culture at 160 rpm at 30° C. for 4 days. After the culture period, the cells were collected from the culture on Miracloth (Calbiochem). The collected cells were washed with 40 ml distilled water and were pressed between sheets of paper towel to remove moisture. The wet cells were weighed.

The relative wet cell weight of the transformant relative to the control is shown in FIGS. 7 and 8 for each concentration of the selenium compound. As can be seen from FIGS. 7 and 8, the transformant showed resistance to each of the selenium compounds.

Example 11: Confirmation of Transformed *Aspergillus sojae*

In a test tube, conidia of each of the *Aspergillus sojae* NBRC4239 strain to serve as control; the transformed *Aspergillus sojae* transformed with one of the genes AsEgtA, AsEgtB and AsEgtC; and the transformed *Aspergillus sojae* transformed with the gene AsEgtA and the gene AsEgtB or AsEgtC were inoculated to 10 ml of a DPY liquid medium and the inoculated medium was subjected to shake culture at 30° C. for 3 days. Subsequently, the cells were collected. The collected cells were triturated in a bead cell disrupter (MS-100R; Tomy Digital Biology) under a chilled condition to give triturated cell powder, which in turn was suspended in a 0.1 (w/v) % aqueous SDS solution to form a SDS suspension. To the resulting SDS suspension, a one-quarter volume of sample buffer (Lane Marker Reducing Sample Buffer, ImmunoPure (5×); Thermo Fisher Scientific) was added and the mixture was stirred. The mixture was then subjected to a heat treatment at 98° C. for 3 min. Following the heat treatment, the mixture was centrifuged and the supernatant was collected. The supernatant in an amount equivalent to 0.2 mg cell was then applied to an acrylamide gel and electrophoresed to perform an SDS-PAGE. The results are shown in FIG. 9.

As can be seen from FIG. 9, the AsEgtA protein appeared as two bands at approximately 90 kDa in SDS-PAGE while its expected molecular weight estimated from the amino acid sequence was 95.7 kDa. Similarly, the AsEgtB protein appeared as a band at little less than 50 kDa while its expected molecular weight estimated from the amino acid sequence was 56.4 kDa. Also, the AsEgtC protein appeared as a band at 50 kDa while its expected molecular weight estimated from the amino acid sequence was 51.2 kDa.

As can be seen from FIG. 9, the control strain expressed little amount of each of the AsEgtA protein, the AsEgtB protein and the AsEgtC protein whereas the (AsEgtA+AsEgtB) transformant and the (AsEgtA+AsEgtC) transformant expressed the AsEgtA protein and either the AsEgtB protein or the AsEgtC protein. Also, the AsEgtA transformant, the AsEgtB transformant and the AsEgtC transformant expressed the AsEgtA protein, the AsEgtB protein and the AsEgtC protein, respectively.

Example 12: Preparation of Transformed *E. coli*

The gene sequences of AsEgtA and AsEgtC genes were optimized for expression in *E. coli* based on the amino acid sequences of the AsEgtA and AsEgtC proteins in terms of the codon, secondary structure and GC content. The EcoRV recognition sequence (GATATC) and the SpeI recognition sequence (ACTAGT) were attached to the upstream and the downstream of the respective genes to obtain EcEgtA (SEQ ID NO:27) and EcEgtC(SEQ ID NO:28), respectively.

Meanwhile, pUTE120K' was constructed as an expression vector. Specifically, pUTE100K' described in JP 06-292584 A was digested with NheI and HpaI to remove the lac promoter. Next, the Tac promoter region of pKK223-3 (GE) with the NheI site attached to the 3' end and the EcoRV site attached to the 5' end was PCR amplified and purified. The amplified promoter was digested with NheI and inserted into the site where the lac promoter was originally located in pUTE100K' to construct pUTE120K'.

pUTE120K' was then digested with restriction enzymes EcoRV and SpeI. Subsequently, EcEgtA or EcEgtC was ligated to construct plasmids pUTE120K'-EcEgtA and pUTE120K'-EcEgtC having EcEgtA or EcEgtC inserted therein.

*E. coli* transformed with the construct plasmids were cultured and the plasmids pUTE120K'-EcEgtA and pUTE120K'-EcEgtC were purified. Next, pUTE120K'-EcEgtC was digested with restriction enzymes BamHI and SpeI to excise a fragment containing the gene EcEgtC. This fragment was purified. Meanwhile, pUTE120K'-EcEgtA was digested with restriction enzymes BamHI and NheI and the fragment containing the gene EcEgtC obtained above was inserted to construct a plasmid pUTE120K'-EcEgtA-EcEgtC. This plasmid was used to transform *E. coli* JM109 strain to create a transformed *E. coli*.

When the transformed *E. coli* is cultured at 25° C. for 16 hours in a TY medium (1 (w/v) % Bacto Tryptone, 0.5 (w/v) % Bacto Yeast Extract, 0.5 (w/v) % NaCl, pH7.0) containing 1 mM selenocystine or 1 mM selenous acid and 0.1 mM isopropyl-β-D-thiogalactopyranoside (IPTG), selenoneine is detected both in the entire culture and in the hot water extract of the collected cells.

Example 13: Preparation of DNA Constructs with Inserted Gene AnEgtA (1) Search for Proteins of Interest Using the amino acid sequence of the AsEgtA protein of *Aspergillus sojae* as a query sequence, proteins with a high sequence identity were searched from the data base Non-redundant protein sequences (nr). Blastp (blast.ncbi.nlm-.nih.gov/Blast.cgi?PROGRAM=blastp& PAGE TYPE=BlastSearch &LINK_LOC=blasthome) was used for the search.

Of the proteins found to have a high sequence identity to the amino acid sequence of the AsEgtA protein, XP_001397117.2 (SEQ ID NO: 30) was found to be a homologous protein of the *Aspergillus niger* CBS 513.88 strain. XP_001397117.2 had a 73% sequence identity to the AsEgtA protein. A gene encoding XP_001397117.2 was identified from the genomic DNA of *Aspergillus niger* and named as a gene AnEgtA (SEQ ID NO: 29), meaning egtA gene derived from *Aspergillus niger*.

(2) Extraction of chromosomal DNA of *Aspergillus niger* IAM2533 strain

The same procedure was followed as in Example 1-(2), except that the conidia of *Aspergillus niger* IAM2533 strain were used.

(3) Preparation of a Construct Plasmid

The vector fragments prepared in Example 1-(3) were used.

(4) Preparation of a Construct for Inserting a Gene of Interest

The same procedure was followed as in Example 1-(4) above, except that the gene of interest is the AnEgtA and the chromosomal DNA of *Aspergillus niger* IAM2533 strain obtained above was used as a template DNA. Primers used to amplify AnEgtA gene and the PCR conditions are shown in Table 11 below.

TABLE 11

| Amplified target region | AnEgtA |
|---|---|
| Forward primer SEQ ID NO: 31 | AnEgtA_1F_Ptef cgcaccaccttcaaaATGTCACCCTTATGTCCGGT CGTCAAG |
| Reverse primer SEQ ID NO: 32 | AnEgtA_2890R_Talp atgtactcctggtacTCAGACATCCCGCACCAGCC |
| PCR condition | 2 min. at 94° C. (15 sec. at 94° C., 30 sec. at 62° C., 3 min. at 68° C.) × 25 cycles |

Similar to Example 1-(4) above, the base sequence of DNA inserted in the extracted plasmid DNA was determined to confirm that DNA constructs in which the gene AnEgtA had been inserted were obtained.

The sequence of the cloned gene AnEgtA was confirmed and found to match with the sequence of a putative gene (ANI_1_792134) of the *A. niger* CBS 513.88 strain (the corresponding amino acid sequence is XP_001397117.2). The genome information of this gene is disclosed.

Example 14: Preparation of Transformed *Aspergillus sojae* (2)

The same procedure was followed as in Examples 2-(1) and (2), except that a DNA construct in which the gene AnEgtA had been inserted was used.

Example 15: Production of Selenoneine Using Transformed *Aspergillus sojae* (3)

The same procedure was followed as in Example 7 above, except that the conidia of *Aspergillus sojae* NBRC4239 strain to serve as control and transformed *Aspergillus sojae* transformed with the gene AnEgtA were inoculated. The resulting selenoneine extract and the culture supernatant obtained from the culture after the main culture (filtered through 0.45 μm filter) were analyzed by LC-ICP-MS using the conditions described in the article by Yamashita et al. to quantify selenoneine. The results of the comparison of selenoneine production between the control strain and the transformed *Aspergillus sojae* are shown in Table 12.

TABLE 12

| Strain | Selenium compound | Selenoneine (mg-Se/kg - Extract) | Selenoneine (mg/L - Extract) | Selenoneine (mg/L - Culture solution) |
| --- | --- | --- | --- | --- |
| AnEgtA transformant | selenocystine | 2.9 | 10.2 | 2.00 |
| Control strain | selenocystine | 0.1 | 0.35 | 0.07 |
| AnEgtA transformant | selenous acid | 0.2 | 0.70 | 0.14 |
| Control strain | selenous acid | 0.1 | 0.35 | 0.07 |

As can be seen from Table 12, similar to the transformed *Aspergillus sojae* transformed with the gene AsEgtA, the transformed *Aspergillus sojae* transformed with the gene AnEgtA showed increased selenoneine production as compared to the non-transformed control strain for each substrate both in the extract and in the culture solution. These results indicate that the transformed *Aspergillus sojae* transformed with a heterologous gene AnEgtA derived from a different organism of origin can also achieve efficient production of selenoneine.

Example 16: Production of Selenoneine Using Transformed *E. coli*

As shown in Table 13 below, the control *E. coli* in which the expression vector pUTE120K' had been introduced; the transformed *E. coli* transformed with the gene EcEgtA or EcEgtC; and the transformed *E. coli* transformed with the gene EcEgtA and the gene EcEgtC were compared for their ability to produce selenoneine in the following manner.

TABLE 13

| Introduced gene | Strain |
| --- | --- |
| pUTE120K' | Control strain |
| EcEgtA | EcEgtA Transformant |
| EcEgtC | EcEgtC Transformant |
| EcEgtA, EcEgtC | (EcEgtA + EcEgtC) Transformant |

In a 19 ml test tube, each of the bacterial strains shown in Table 13 was inoculated into 2.5 ml of a TY medium. The inoculated medium was then seed-cultured at 37° C. for 16 hours while agitated at 180 rpm. In a 19 ml test tube, 20 μl of the seed culture was inoculated into 2.5 ml of a TY medium containing ampicillin and 0.5 mM IPTG. The inoculated medium was then main-cultured at 25° C. for 20.5 hours while agitated at 180 rpm. Three different lines of TY medium were prepared for the main culture: a TY medium containing 0.1 mM selenocystine (TY++), a TY medium containing 0.01 mM selenocystine (TY+), and a TY medium to which selenocystine was added to 0.01 mM six hours after the start of culture (TY+○).

Meanwhile, in a 19 ml test tube, 20 μl of the seed culture was inoculated into 0.6 ml of a TY medium containing ampicillin and 0.5 mM IPTG. The inoculated medium was then main-cultured at 25° C. for 25 hours while agitated at 180 rpm. After the addition of selenocystine to 0.01 mM, 10 μl of 2.5 mM selenocystine was added 20.5 hours after the start of culture and the culturing was continued for additional 4.5 hours (TY+++).

After the culture period, the culture was centrifuged (12,000 rpm, 4° C., 10 min) and the cells were collected as precipitate. To cells obtained from 1 ml of the cultures of TY+++, TY+ and TY+○, and to cells obtained from 0.6 ml of the culture of TY+++, 0.2 ml water was added to form cell suspensions. The resulting cell suspensions were subjected to a heat treatment at 98° C. for 10 min. Following the heat treatment, each suspension was centrifuged to collect the extracellular fluid as the supernatant, which in turn was filtered through a 0.45 μm filter to obtain a selenoneine extract.

The amounts of selenoneine were determined in the resulting selenoneine extracts and culture supernatants obtained from the cultures after main culture (filtered through 0.45 μm filter) by LC-MS/MS using the conditions given below. The determined amounts of selenoneine are shown in Table 14.

LC apparatus; ACQUITY UPLC (Waters)
Mass spectrometer; Micromass Quattro micro API (Waters)
Column; COSMOSIL 2.5HILIC (3.0×100 mm)
Eluent; acetonitrile+0.1% formic acid: water+0.1% formic acid=80:20 (v/v)
Flow rate; 500 μl/ml
Detection; ESI positive
Injection; 2 μl
Temperature; 40° C.
Quantification method; Calibration curve method using selenoneine samples (products of *Aspergillus oryzae*)

TABLE 14

| Strain | Culture line | Concentration ratio | Selenoneine mg/L - Extract | Selenoneine mg/L - Culture solution |
| --- | --- | --- | --- | --- |
| EcEgtA transformant | TY++ | 5 | nd | nd |
| EcEgtC transformant | TY++ | 5 | nd | nd |
| (EcEgtA + EcEgtC) transformant | TY++ | 5 | 0.12 | 0.02 |

TABLE 14-continued

| Strain | Culture line | Concentration ratio | Selenoneine mg/L - Extract | Selenoneine mg/L - Culture solution |
|---|---|---|---|---|
| Control strain | TY++ | 5 | nd | nd |
| EcEgtA transformant | TY+ | 5 | 0.67 | 0.13 |
| EcEgtC transformant | TY+ | 5 | nd | nd |
| (EcEgtA + EcEgtC) transformant | TY+ | 5 | 0.92 | 0.18 |
| Control strain | TY+ | 5 | nd | nd |
| EcEgtA transformant | TY+o | 5 | 0.65 | 0.13 |
| EcEgtC transformant | TY+o | 5 | nd | nd |
| (EcEgtA + EcEgtC) transformant | TY+o | 5 | 0.96 | 0.19 |
| Control strain | TY+o | 5 | nd | nd |
| EcEgtA transformant | TY+++ | 3 | 0.86 | 0.29 |
| EcEgtC transformant | TY+++ | 3 | nd | nd |
| (EcEgtA + EcEgtC) transformant | TY+++ | 3 | 1.60 | 0.53 |
| Control strain | TY+++ | 3 | nd | nd |

As can be seen from FIG. 14, in any of the culture lines, selenoneine was not detected in the control strain and in the EcEgtC transformant, whether in the culture supernatant or in the selenoneine extract. This suggests that the control strain and the EcEgtC transformant each have little or no ability to produce selenoneine.

In comparison, the EcEgtA transformant and the (EcEgtA+EcEgtC) transformant both exhibited an ability to produce selenoneine. In addition, the amount of selenoneine produced by the (EcEgtA+EcEgtC) transformant was higher than that of the EcEgtA transformant and the difference between the two transformants was more significant in the culture supernatants. The comparison of effects of selenocystine addition to the culture medium indicates that both the EcEgtA transformant and the (EcEgtA+EcEgtC) transformant showed increased selemmeine production when selenocystine was added after sufficient time has elapsed after the start of culture. The TY++ lines resulted in low selenoneine levels since the high concentration of selenocystine present during the initial stage of culture caused growth inhibition. This suggests that during the initial stage of culture, selenocystine may preferably be added in sufficiently small amounts relative to the cell concentration and may preferably be increased over the course of culture or as the cell concentration increases.

These results indicate that the (EcEgtA+EcEgtC) transformant has an enhanced selenoneine production capability that is increased multiplicatively, rather than additively, from that of the EcEgtA transformant since the EcEgtA transformant showed high selenoneine production whereas the EcEgtC transformant showed no production of selenoneine.

Example 17: Production of Selenoneine Using Transformant *Aspergillus sojae* in Selenium Yeast Medium In a 200 mL Erlenmeyer flask, conidia of the transformed *Aspergillus sojae* transformed with the gene AsEgtA were inoculated into 40 ml of a selenium yeast liquid medium (1.5 (w/v) % selenium yeast, 2 (w/v) % dextrin, 0.5 (w/v) % $KH_2PO_4$, 0.05 (w/v) % $MgSO_4 \cdot 7H_2O$; pH not adjusted), and the inoculated medium was subjected to shake culture at 160 rpm at 30° C. for 5 days.

After the culture period, the cells were collected from the culture on Miracloth (Calbiochem). The collected cells were washed with 40 ml distilled water and 8 ml water was then added and agitated to suspend the cells and form a cell suspension. The resulting cell suspension was subjected to a heat treatment at 100° C. for 15 min. Following the heat treatment, each suspension was centrifuged to collect the extracellular fluid as the supernatant, which in turn was filtered through a 0.45 μm filter to obtain a selenoneine extract.

The amount of selenoneine was determined by LC-MS/MS in the resulting selenoneine extract and the medium not inoculated with the production strain. The determined amounts of selenoneine are shown in Table 15. It was confirmed that the transformed *Aspergillus sojae* can utilize selenium in selenium yeast to produce selenoneine.

TABLE 15

| | Selenoneine (ppm) |
|---|---|
| selenium yeast medium | n.d. |
| Extract | 3.39 ppm |

Example 18: Production of Selenoneine Using Transformant *Aspergillus sojae* in Tuna/Bonito Extract Medium (Bacterio-N-KN)

In a 200 mL Erlenmeyer flask, conidia of the transformed *Aspergillus sojae* transformed with the gene AsEgtA were inoculated into 40 ml of a tuna/bonito extract medium (2.0 (w/v) % Bacterio-N-KN (Maruha Nichiro), 2 (w/v) % dextrin, 0.5 (w/v) % $KH_2PO_4$, 0.05 (w/v) % $MgSO_4 \cdot 7H_2O$; pH not adjusted), and the inoculated medium was subjected to shake culture at 160 rpm at 30° C. for 5 days.

After the culture period, the cells were collected from the culture on Miracloth (Calbiochem). The collected cells were washed with 40 ml distilled water and 4 ml water was then added and agitated to suspend the cells and form a cell suspension. The resulting cell suspension was subjected to a heat treatment at 100° C. for 15 min. Following the heat treatment, each suspension was centrifuged to collect the extracellular fluid as the supernatant, which in turn was filtered through a 0.45 μm filter to obtain a selenoneine extract.

The amount of selenoneine was determined by LC-MS/MS in the resulting selenoneine extract and the medium not inoculated with the production strain. The determined amounts of selenoneine are shown in Table 16. It was confirmed that the transformed *Aspergillus sojae* can utilize selenium in a tuna/bonito extract to produce selenoneine.

TABLE 16

| | Selenoneine (ppm) |
|---|---|
| tuna/bonito liquid medium | n.d. |
| Extract | 0.345 ppm |

INDUSTRIAL APPLICABILITY

The production method and the transformant to serve as one embodiment of the present invention can be used to produce selenoneine, which is said to have antioxidative activity 1,000 times as high as that of ergothioneine. Accordingly, the present invention is useful in the industrial-scale production of raw materials used to produce cosmetics and supplements with antioxidative activity.

[Sequence Listing]

The invention claimed is:

1. A method for producing selenoneine, comprising the step of;

contacting histidine and selenous acid with a transformant by using as a host organism *Aspergillus* that has a gene encoding an enzyme of (1) introduced therein as foreign gene and that can overexpress the introduced gene to obtain selenoneine, wherein the enzyme of (1) catalyzes a reaction in which hercynylselenocysteine of formula is produced from histidine and selenocysteine in the presence of S-adenosylmethionine and iron (II), wherein the gene encoding the enzyme of (1) has the nucleotide sequence of SEQ ID NO: 1, or the enzyme of (1) has the amino acid sequence of SEQ ID NO: 4, and wherein formula [I] is:

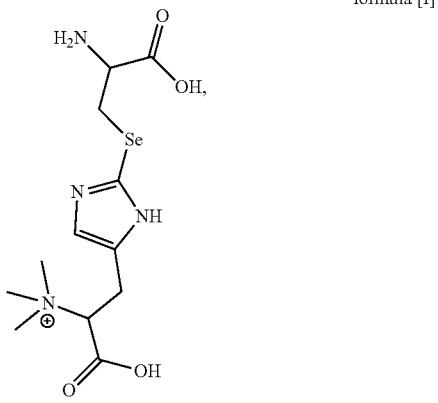

formula [I]

wherein the host organism further has a second ne encoding an enzyme of (2) expressed therein, wherein the enzyme of (2) catalyzes a reaction in which selenoneine is produced from hercynylselenocysteine of formula [I] using pyridoxal 5'-phosphate as a coenzyme, and wherein the second gene encoding the enzyme of (2) has the nucleotide sequence of SEQ ID NO: 2 or 3, or the enzyme of (2) has the amino acid sequence of SEO ID NO: 5 or 6.

2. The method according to claim 1, wherein the transformant further expresses at least one enzyme selected from the group consisting of selenic acid reductase, selenocysteine lyase, and serine dehydratase.

3. The method according to claim 1, wherein the transformant is produced by using as a host organism *Aspergillus* selected from the group consisting of *Aspergillus sojae, Aspergillus oryzae, Aspergillus niger, Aspergillus tamarii, Aspergillus awarmori, Aspergillus usamii, Aspergillus kawachii*, and *Aspergillus saitoi*.

4. The method according to claim 1, wherein the transformant is a transformant in which the expression of the gene encoding the enzyme of (1) is enhanced to increase the amount of selenoneine as compared to the host organism.

5. The method according to claim 1, wherein the transformant is a transformant in which the expression of the gene encoding the enzyme of (1) is enhanced so that the amount of selenoneine produced when the transformant is cultured in a selenocystine-containing medium suitable for the growth of the host organism at 30° C. for 5 days is not less than 10 μg per gram of wet cell mass.

6. The method according to claim 1, wherein the enzyme of (2) is AsEgtC.

7. The method according to claim 1, wherein the second gene encoding the enzyme of (2) has the nucleotide sequence of SEQ ID NO: 2, or the enzyme of (2) has the amino acid sequence of SEQ ID NO: 5.

8. The method according to claim 1, wherein the second gene encoding the enzyme of (2) has the nucleotide sequence of SEQ ID NO: 3, or the enzyme of (2) has the amino acid sequence of SEQ ID NO: 6.

9. The method according to claim 1, wherein the microorganism is *Aspergillus sojae*.

10. The method according to claim 6, wherein microorganism is *Aspergillus sojae*.

11. The method according to claim 7, wherein the gene is obtained from the microorganism *Aspergillus sojae*.

12. The method according to claim 8, wherein the microorganism is *Aspergillus sojae*.

* * * * *